United States Patent [19]

Katano et al.

[11] Patent Number: 5,594,004
[45] Date of Patent: Jan. 14, 1997

[54] COMPOUND WITH PLATELET AGGREGATION INHIBITOR ACTIVITY

[75] Inventors: Kiyoaki Katano; Shokichi Ohuchi; Eiki Shitara; Masaro Shimizu; Kazue Yaegashi; Tomoaki Miura; Yasuko Isomura; Hiroyuki Iida; Midori Ishikawa; Kenji Asai; Emiko Hatsushiba; Mami Kawaguchi; Takashi Tsuruoka, all of Kanagawa-ken, Japan

[73] Assignee: Meiji Seika Kabushiki Kaisha, Tokyo-to, Japan

[21] Appl. No.: 347,402

[22] PCT Filed: Mar. 17, 1994

[86] PCT No.: PCT/JP94/00437

§ 371 Date: Jan. 30, 1995

§ 102(e) Date: Jan. 30, 1995

[87] PCT Pub. No.: WO94/21599

PCT Pub. Date: Sep. 29, 1994

[30] Foreign Application Priority Data

| Mar. 17, 1993 | [JP] | Japan | 5-057463 |
| Apr. 8, 1993 | [JP] | Japan | 5-082145 |
| Oct. 22, 1993 | [JP] | Japan | 5-265273 |

[51] Int. Cl.⁶ .............. A61K 31/435; C07D 211/34; C07D 211/62; C07D 471/04

[52] U.S. Cl. .............. 514/301; 514/222.5; 514/233.8; 514/255; 514/256; 514/300; 514/302; 514/318; 514/330; 546/113; 546/114; 546/115; 546/193; 546/225

[58] Field of Search .............. 546/114, 113, 546/115, 193, 225; 514/301, 302, 300, 318, 330, 222.5, 233.8, 256, 255

[56] References Cited

FOREIGN PATENT DOCUMENTS

| 381033 | 8/1990 | European Pat. Off. |
| 62-155250 | 7/1987 | Japan |
| 2-503797 | 11/1990 | Japan |
| 3-505728 | 12/1991 | Japan |
| 5-505813 | 8/1993 | Japan |

OTHER PUBLICATIONS

Jain PC, Paul B, Anand N. Indian J. Chem. 10(5), 455–60 (abstract) 1972.
Merck Manual. Eleventh Edition (1966). p. 1574 Merck USA.

*Primary Examiner*—C. Warren Ivy
*Assistant Examiner*—Evelyn Huang
*Attorney, Agent, or Firm*—Wenderoth Lind & Ponack

[57] ABSTRACT

A compound represented by the general formula (I) and a pharmaceutically acceptable salt and solvate thereof having an effect for inhibiting the agglutination of platelets is disclosed:

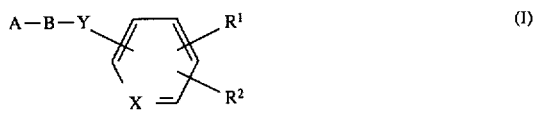

wherein $R^1$ represents a group $-W-(CH_2)_i-COOR^3$, $R^2$ represents a hydrogen atom or a group $-W-(CH_2)_i-COOR^3$ or $-OR^4$, X represents $-CH=$ or $-N=$, Y represents
  (i) a group $-(CO)_k-N(R^5)-Z-$, wherein Z represents a bond or a group $-(CH_2)_m-CO-$ or a group $-(CH_2)_m-CHR^6-$,
  (ii) a group $-(CH_2)_m-N(R^5)-(CO)_k-$, or
  (iii) a group $-(CO)_k$-Het, wherein Het represents a five- or six-membered heterocyclic ring comprising a nitrogen atom, A represents
  (i) the following groups (III) or (IV)

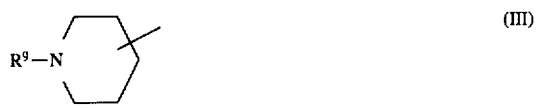

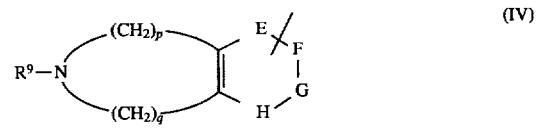

B represents a bond, $C_{1-6}$ alkylene or $C_{2-6}$ alkenylen.

21 Claims, No Drawings

COMPOUND WITH PLATELET AGGREGATION INHIBITOR ACTIVITY

This application is the National phase of PCT/JP94/00437 filed on Mar. 17, 1994 and published as WO94/21599 on Sep. 29, 1994.

FIELD OF THE INVENTION

The present invention relates to a cyclohexene and a nitrogen-containing heterocyclic derivative for inhibiting the aggregation of platelets, and a pharmaceutical composition for the treatment and prophylaxis of thrombotic diseases comprising as effective ingredient at least one of these derivatives.

BACKGROUND TECHNOLOGIES

Caldiovascular diseases are increased along with the change of dietary habits and the increase of advanced ages. Almost fifty percent of these diseases may be caused by thrombus.

Platelets in plasma are mainly associated with the formation of thrombus in organisms. For the purpose of the treatment and prophylaxis of thrombotic diseases in clinical practice, there have been used a medicine which suppresses the functions of platelet or inhibits the aggregation of platelets, for example, aspirin which inhibits cyclooxygenase and ticlopidine which activates adenylcyclase.

In recent years, glycoproteins on platelet membrane have been progressively analyzed. As the results, it has been elucidated that the glycoprotein called GPIIb/IIIa is a receptor of fibrinogen. This has therefore led to the expectation that a GPIIb/IIIa antagonists would become an inhibitor of platelet aggregation having a novel action mechanism effectively used for the treatment and prophylaxis of the thrombotic diseases (Trends in Pharmacological Science, 13, 413, 1992). The compounds as the GPIIb/IIIa antagonist include a monoclonal antibody (Ann. New York Acad. Sci., 614, 193, 1991), a tripeptide derivative comprising arginine-glycine-aspartic acid (J. Med. Chem., 35, 2040, 1992), amidinophenyl derivative (J. Med. Chem., 35, 4393, 1992; Japanese Patent Laid-Open Publication Nos. 264068/1992 and 334351/1992), and a tyrosine derivative (J. Med. Chem., 35, 4640, 1992).

It is also desired to be developed a medicine having no side effects such as hemorrhage and a highly selective function as a therapeutic or prophylactic agent of thrombotic diseases.

SUMMARY OF THE INVENTION

The present inventors have now found that a certain kind of a compound becomes a GPIIb/IIIa antagonist.

Thus, an object of the present invention is to provide a novel compound inhibiting the aggregation of platelets.

Another object of the present invention is to provide a pharmaceutical composition comprising a novel compound having the aforementioned effect.

Further object of the present invention is to provide a therapeutic or prophylactic method of thrombotic diseases which comprises administering a novel compound having the above activity.

Further object of the present invention is to provide the use of the novel compound having the above activity for preparing a pharmaceutical composition used for the therapy or prophylaxis of thrombotic disorders.

The compound according to the present invention is represented by the formula (I):

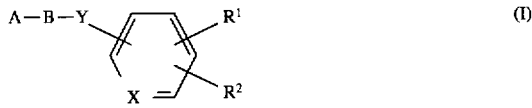

or a pharmaceutically acceptptable salt ans solvate thereof wherein $R^1$ represents a group —W—$(CH_2)_i$-COOR$_3$ where W represents O- or a bond, $R^3$ represents hydrogen lower alkyl, $C_{5-7}$ cycloalkyl or an ester moiety which may be removed under a physiological condition and i is an integer from 1 to 4, $R^2$ represents hydrogen or a group —W—$(CH_2)_i$—COOR$^3$ where W, $R^3$ and i have the same meanings as defined above, or a group $OR^4$, where $R^4$ represents hydrogen lower alkyl mono-lower alkylaminocarbonyl or phenyl-lower alkyl, X represents CH or N, Y represents (i) a group —$(CO)_k$—N($R^5$)—Z—, where k is 0 or 1, $R^5$ represents hydrogen; lower alkyl in which one or more hydrogen atoms may be substituted by hydroxyl, halogen, amino, carboxyl, lower alkoxy, lower alkylamino, or lower alkoxycarbonyl; phenyl-lower alkyl in which one or more hydrogen atoms in the phenyl moiety may be substituted by hydroxyl, halogen, amino, carboxyl, lower alkoxy, lower alkylamino, lower alkoxycarbonyl or halo-lower alkyl; or acyl, Z represents a bond, or a group —$(CH_2)_m$—CO— or a group —$(CH_2)_m$—CHR$^6$—, where m is an integer from 1 to 3 and $R^6$ represents hydrogen or hydroxyl, (ii) a group —CO—$(CH_2)_m$—N($R^5$)—$(CO)_k$—, where k, m and $R^5$ have the same meanings as defined above, or (iii) a group —$(CO)_k$-Het, where represents a five- or six-membered heterocyclic moiety which contains 1 to 4 nitrogen atoms, which may also optionally contain an oxygen atom or a sulfur atom when the heterocyclic moiety contains 1 or 2 nitrogen atoms, and k is 0 or 1, A represents (i) the following group (II):

wherein

D represents a group —$(CH_2)_s$—, where s is an integer from 1 to 4, or a group —C(=NH)—, and $R^7$ and $R^8$ represent independently hydrogen, lower alkyl, acyl, aromatic acyl which may be substituted, or amidino, (ii) the following group (III):

wherein $R^9$ represents hydrogen; lower alkyl in which one or more hydrogen atoms may be substituted by hydroxyl, halogen, amino or lower alkyl amino; or amidino, or (iii) the following group (IV):

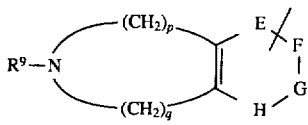

wherein

R$^9$ has the same meanings as defined above,

E, F, G and H independently represent a group —CR$^{10}$, —CR$^{10}$R$^{11}$—, —N=, —NR$^{10}$—, —O—, —S— or —(CO)— or a bond where R$^{10}$ and R$^{11}$, which may be the same or different represent hydrogen or lower alkyl or phenyl-lower alkyl, p and q independently represent an integer of from 1 to 3 provided that p+q is in the range of from 3 to 5, and B represents a bond, C$_{1-6}$ alkylene or C$_{2-6}$ alkenylene.

DETAILED DESCRIPTION OF THE INVENTION

Compound of the Formula (I)

The term "lower alkyl" as a group or a portion of a group herein means a straight or branched alkyl chain having 1 to 6, preferably 1 to 4 carbon atoms. The terms "alkylene" and "alkenylene", respectively, mean a bivalent group derived by removing hydrogen atoms from both terminals of a straight or branched alkane or alkene chain. The term halogen atom means fluorine, chlorine, bromine or iodine. Furthermore, the term "haloalkyl" means an alkyl group in which one or more hydrogen atoms are substituted by halogen atoms.

In the group —W—(CH$_2$)$_i$—COOR$^3$ as R$^1$, i represents preferably an integer of from 1 or 2. R$^3$ represents preferably a hydrogen atom or lower alkyl which is preferably C$_{1-6}$ alkyl, more preferably C$_{1-4}$ alkyl, and specifically includes methyl, ethyl, n-propyl, iso-propyl, or n-, iso-, sec- or t-butyl. Specific examples of an ester moiety as R$^3$ which may be removed under physiological conditions include pivaloyloxymethyl, 1-(cyclohexyloxy-carbonyloxy)ethyl or (5-methyl-2-oxo-1,3-dioxol-4-yl)methyl.

Preferred examples of R$^2$ include hydrogen and the group —W—(CH$_2$)$_i$—COOR$^3$. Preferred examples of the group —W—(CH$_2$)$_i$—COOR$^3$ as R$^2$ include those which are the same as in R$^1$. When R$^1$ and R$^2$ represent the group —W—(CH$_2$)$_i$—COOR$^3$, they may be the same or different.

In the group —OR$^4$ as R$^2$, lower alkyl as R$^4$ represents preferably C$_{1-6}$ alkyl, more preferably C$_{1-4}$ alkyl, and specifically include methyl, ethyl, n-propyl, iso-propyl, or n-, iso-, sec- or t-butyl. The mono-lower alkylaminocarbonyl group as R$^4$ represents preferably mono-C$_{1-6}$ alkylaminocarbonyl, more preferably mono-C$_{1-4}$ alkylaminocarbonyl. Preferred examples of phenyl-lower alkyl as R$^4$ include phenyl C$_{1-4}$ alkyl such as benzyl.

The substituted positions of R$^1$ and R$^2$ is not limited in particular, but it is preferably in the meta- and/or para-positions to the position that the group Y is attached to.

In the group —(CO)$_k$—N(R$^5$)—Z— as Y, R$^5$ represents hydrogen, lower alkyl, phenyl-lower alkyl or acyl, preferably hydrogen, C$_{1-6}$ alkyl (more preferably C$_{1-4}$ alkyl, more specifically methyl, ethyl, n-propyl, iso-propyl, or n-, iso, sec- or t-butyl), benzyl, 2-phenylethyl, 3-phenylpropyl or lower alkylcarbonyl (preferably C$_{1-6}$ alkylcarbonyl, more preferably C$_{1-4}$ alkylcarbonyl) group, and aromatic acyl such as benzoyl, α-naphthoyl and β-naphthoyl.

One or more hydrogen atoms in the lower alkyl may be substituted, and specific examples of the substituents include hydroxyl; halogen such as preferably chlorine, bromine and fluorine; amino; carboxyl; lower alkoxy such as preferably methoxy, ethoxy, n-propoxy and iso-propoxy; lower alkylamino such as preferably methylamino, ethylamino, propylamino, dimethylamino and diethylamino; and lower alkoxycarbonyl such as preferably methoxycarbonyl, ethoxycarbonyl, n-propoxycarbonyl and iso-propoxycarbonyl.

Furthermore, one or more hydrogen atoms of the phenyl moiety in the phenyl-lower alkyl group may be substituted. Specific examples of the substituent include hydroxyl; halogen; amino; carboxyl; lower alkoxy such as preferably methoxy, ethoxy and propoxy; lower-alkylamino such as preferably methylamino, ethylamino, propylamino, dimethylamino and diethylamino; lower alkoxycarbonyl such as preferably methoxycarbonyl, ethoxycarbonyl and propoxycarbonyl; and halo-lower alkyl such as preferably trifluoromethyl and trifluoroethyl.

In the group —(CO)$_k$—N(R$^5$)—Z—, k is 0 or 1; —(CO)$_k$— means a linkage when k is 0. In the group —(CH$_2$)$_m$—CO— or —(CH$_2$)$_m$—CHR$^6$ as Z, m preferably is 1 or 2. When k is 0, Z preferably represents the group —(CH$_2$)$_m$—CHR$^6$, wherein R$^6$ represents hydrogen.

In the group —CO—(CH$_2$)$_m$—N(R$^5$)—(CO)$_k$— as Y, preferred examples of R$^5$ include those described above.

In the group —(CO)$_k$—Het— as Y, Het represents a five- or six-membered heterocyclic moiety containing 1 to 4, preferably 1 or 2 nitrogen atoms. The heterocyclic ring may optionally contain further one oxygen or sulfur atom when the ring contains 1 or 2 nitrogen atoms. Preferred examples of the heterocyclic moiety include heterocyclic moieties formed by leaving two hydrogen atoms from pyrrole, imidazole, pyrazole, 1,2,3-triazole, 1,2,4-triazole, tetrazole, oxazole, isoxazole, thiazole, isothiazole, 1,2,4-oxadiazole, 1,3,4-oxadiazole, 1,2,3-thiadiazole, 1,3,4-thiadiazole, 1,2,4-thiadiazole, pyridine, pyridazine, pyrazine, oxazine or thiazine. According to the preferred embodiment of the present invention, preferred heterocyclic moieties include oxazole, isoxazole, thiazole and isothiazole moieties.

The position of the group Y to a benzene ring or a pyridine ring and to the group B is not limited particularly. Moreover, the bonding may be either a carbon-carbon bond or a carbon-nitrogen bond. According to the preferred embodiment of the present invention, the group Y is introduced into an ortho position to X.

Moreover, in the group (II) as A, preferred examples of the lower alkyl as R$^7$ and R$^8$ include methyl, ethyl, propyl, isopropyl, and n-, sec- and t-butyl. Preferred examples of the lower acyl as R$^7$ and R$^8$ include formyl and lower alkylcarbonyl such as acetyl, propionyl and butyryl. Preferred examples of the aromatic acyl as R$^7$ and R$^8$ include benzoyl, α-naphthoyl and β-naphthoyl. One or more hydrogen atoms in the aromatic acyl group may be substituted, and preferred examples of the substituent include amidino, amino, chlorine, fluorine or hydroxyl, particularly benzoyl group substituted by one of the above substituents at either one of the o-, m- or p-positions.

In —(CH$_2$)$_s$— as D in the group (II), s preferably represents an integer of 1 to 3, more preferably 1 or 2.

In the group (II), the groups D and B may be bonded to the cyclohexane ring in either configurations of cis- or trans-types depending on the formations of the bonds. Both of the isomers are included in the present invention. The trans-isomer is particularly preferred.

In the groups (III) and (IV) as A, R$^9$ represents hydrogen, lower alkyl or amidino group. One or more hydrogen atoms in the lower alkyl group may be substituted, and specific examples of the substituent include hydroxyl; halogen such as preferably chlorine, bromine or fluorine; amino; and lower alkylamino such as preferably methylamino, ethylamino, dimethylamino and diethylamino.

The bonding position of the group (III) and the group B is not limited particularly, but it is preferably at the 4-position to $R^9N$.

In the group (IV), p and q independently represent an integer of 1 to 3, and p+q is in the range of 3 to 5, preferably 3 or 4.

In the preferred example of the group (IV), p is 2, q is 2 or 3, either E or H represents —$NR^{10}$—, —O— or —S— and the other represents a bond, and both of F and G represent —$CR^{10}$=, or one of F or G represents —$CR^{10}$= and the other represents —$NR^{10}$—, —O— or —S—. Specific examples preferably include 4,5,6,7-tetrahydrothieno[3,2-c]pyridin-2-yl or -3-yl, 4,5,6,7-tetrahydrothieno[2,3-c]pyridin-2-yl or -3-yl, 1-methyl-4,5,6,7-tetrahydro-pyrrolo[3,2-c]pyridin-2-yl or -3-yl, 1-methyl-4,5,6,7-tetrahydropyrrolo[2,3-c]pyridin-2-yl or -3-yl, 4,5,6,7-tetrahydrofuro[3,2-c]pyridin-2-yl or -3-yl, 4,5,6,7-tetrahydrofuro[2,3-c]pyridin-2-yl or -3-yl, 5,6,7,8-tetrahydro-4H-thieno[3,2-c]azepin-2-yl or -3-yl, or 5,6,7,8-tetrahydro-4H-thieno[2,3-d]azepin-2-yl or -3-yl.

In the group (IV), $R^{10}$ and $R^{11}$ preferably represent hydrogen, $C_{1-4}$ alkyl or phenyl-$C_{1-4}$ alkyl such as benzyl.

The $C_{1-6}$ alkylene as B is preferably-$C_{1-4}$ alkylene, more preferably $C_{1-3}$ alkylene. The $C_{2-6}$ alkylene as B is more preferably $C_{2-4}$ alkylene.

The preferred group of the compounds of the present invention includes a group wherein Y represents a group —$(CO)_k$—$N(R^5)$—Z—, where k is 1, or a group —$(CO)_k$—Het—, and A represents the group (II). According to the more preferred embodiment, in the group, B represents a bond and X represents CH. According to the further preferred embodiment, in the group, Z represents a group —$(CH_2)_m$—CO— or a group —$(CH_2)_m$—$CHR^6$, where $R^6$ represents hydrogen.

According to another preferred embodiment of the present invention, there provides a group in which Y represents a group —$(CO)_k$—$N(R^5)$—Z—, where k is 1, or a group —$(CO)_k$—Het—, A represents the group (III), and B represents a bond or $C_{1-6}$ alkylene. In this group, a compound wherein Z represents a group $(CH_2)_m$—CO— or a group —$(CH_2)_m$, $CHR^6$, where $R^6$ represents hydrogen and B represents a bond or $C_{1-6}$ alkylene is more preferred.

According to further preferred embodiment of the present invention, there provides a group wherein Y represents a group —$(CO)_k$—$N(R^5)$—Z— where k is 1, or a group —NHCO— or a group —(CO)k —Het—, A represents the group (IV), and B represents a bond or $C_{1-6}$ alkylene. In this group, the compound in which A represents the group (IV) where either E or H represents —$NR^{10}$—, —O— or —S—, the other represents a bond, and F or G represents $CR^{10}$= is preferred Furthermore, in the group, the compound in which either p or q is 1 and the other is 2 or both of p and q is 2, is preferred. Moreover, in the group, the compound in which either F or G represents —$CR^{10}$= where $R^{10}$ represents hydrogen, the other represents —$CR^{10}$= where $R^{10}$ is not hydrogen, is more preferred. In the group, the compound in which A represents the group (IV), where either E or H represents —$NR^{10}$, —O— or —S—, the other represents a bond, and either F or G represents —$CR^{10}$= and the other represents —$NR^{10}$—, —O— or —S— is another preferred one. Moreover, the compound in which Y represents the group —$(CO)_k$—Het—, is another preferred one.

The compound according to the present invention can be in the form of a salt. Such a salt includes a pharmacologically acceptable non-toxic salt. Preferred examples of the salt include inorganic salts such as a sodium salt, a potassium salt, a magnesium salt and a calcium salt, acid addition salts such as a trifluoroacetate salt, a hydrochloride salt, an oxalate salt and a methanesulfonate salt a citrate salt, and amino acid salts such as a glutamate salt and an aspartate salt.

The compound according to the present invention can be in the form of a solvate. The solvate preferably includes a hydrate and an ethanolate.

Preparation of the Compound represented by the Formula (I)

The compound according to the present invention can be prepared by the following process:

(1) In the case of the compound in which Y represents the group —$(CO)_k$—$N(R^5)$—Z—, where Z represents a bond, a group$(CH_2)_m$—CO— or a group —$(CH_2)_m$, —$CHR^6$, where $R^6$ represents hydrogen, but $R^5$ does not represent lower acyl:

This compound can be prepared by reacting the compound represented by the formula (V):

$$A—B—(CO)_k—L \quad\quad (V)$$

wherein A, B and k have the same meanings as defined in the formula (I), and L represents halogen, alkylsulfonyloxy or arylsulfonyloxy, with the compound represented by the formula (VI):

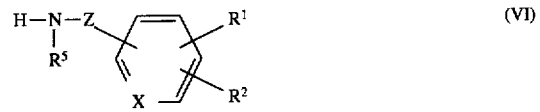

wherein $R^1$, $R^2$, $R^5$ and X have the same meanings as defined in the formula (I), provided that when $R^1$ and $R^2$ contain a carboxyl group or a hydroxyl group, the carboxyl group and the hydroxyl group may be protected, Z represents a bond, a group$(CH_2)_m$—CO— or a group —$(CH_2)_m$—$CHR^6$, where $R^6$ represents a hydrogen atom, in the presence or absence of a base in an inert solvent at a temperature of −30° to 100° C., preferably −20° to 80° C. for 30 minutes to 48 hours, preferably 1 to 10 hours, and removing the protective groups, if necessary.

The compound represented by the formula (V) can be prepared according to the known method, for example, described in Chem. Pharm. Bull., 34 (9), 3747 (1986), Ark. Kemi., 32, 217 (1970), and Japanese Patent Laid-Open Publication Nos. 150687/1982 and 2992/1988.

The compound represented by the formula (VI) wherein X represents —CH= can be also prepared according to the method described in Japanese Patent Laid-Open Publication Nos. 65240/1977 and 158922/1986.

Moreover, the compound represented by the formula (VI) wherein X represents N and represents a group —$(CH_2)_m$—CO— can be prepared by the process according to the following scheme:

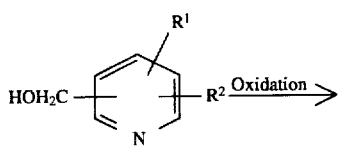

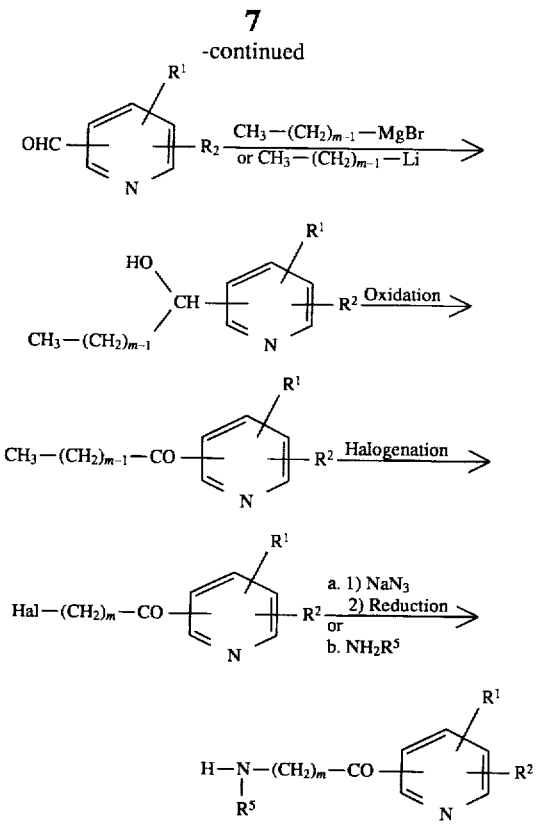

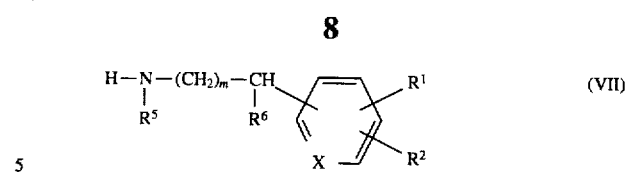

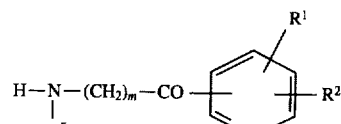

wherein $R^1$, $R^2$, $R^5$, X and n have the same meanings as defined in the formula (I), and $R^6$ represents hydroxyl, under substantially the same conditions as in the above process (1).

The compound of the formula (VII) can be prepared, for example, by reducing a compound represented by the formula:

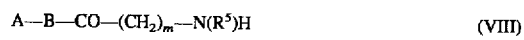

with a suitable reducing agent (e.g. catalytic reduction).

(3) In the case of the compound wherein Y represents the group $-(CO)_k-N(R^5)-Z-$, wherein $R^5$ represents lower acyl:

This compound can be prepared by reacting a compound represented by the formula A-B-CHO with the compound represented by the above formula (VI) wherein $R^5$ represents hydrogen or the compound represented by the formula (VII) wherein $R^5$ represents hydrogen in the presence of a reducing agent such as $NaCNBH_3$ or $H_2/Pd$-C to give the compound represented by the formula (I) wherein $R^5$ represents hydrogen, which is then reacted with an appropriate acylating agent such as acetic anhydride, acetyl chloride or benzoyl chloride.

(4) In the case of the compound wherein Y represents the group $-CO-(CH_2)_m-N(R^5)-(CO)_k-$:

This compound can be prepared by reacting the compound represented by the formula:

A—B—CO—(CH$_2$)$_m$—N(R$^5$)H    (VIII)

wherein $R^5$ and m have the same meanings as defined in the formula (I), with the compound represented by the formula (IX):

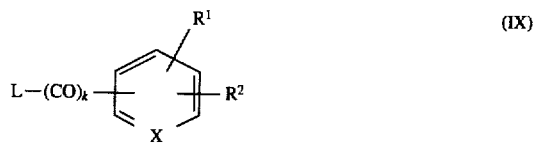

wherein $R^1$, $R^2$, X and k have the same meanings as defined in the formula (I), and L represents halogen, alkyl or allylsulfonyloxy, in the presence or absence of a base such as triethylamine, N-methylmorpholine, pyridine, N,N-dimethyl-aminopyridine in an inert solvent at $-30°$ C. to $100°$ C., preferably $-10°$ C. to $50°$ C. for 30 minutes to 48 hours, preferably 1 to 24 hours, and removing the protective group, if necessary.

The compound represented by the formula (VIII) can be prepared according to the following scheme:

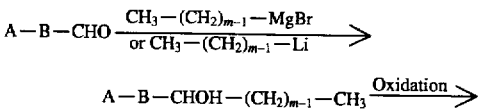

wherein $R^1$, $R^2$, $R^5$ and n have the same meanings as defined in the formula (I), provided that when $R^1$ and $R^2$ contain a carboxyl group and a hydroxyl group, the carboxyl group and the hydroxyl group may be protected, and Hal represents a halogen atom. The compound represented by the formula (VI) wherein X represents N and Z represents a group $-(CH_2)_m$, $CHR^6-$, where $R^6$ represents hydrogen, can be prepared by halogenating followed by reducing the hydroxyl group of the compound represented by the formula (I) wherein Z in Y represents $-(CH_2)_m-CHOH-$. The halogenation can be carried out by using a reagent such as thionyl chloride or phosphorus pentachloride in an inert solvent such as chloroform or dichloromethane at a temperature of $-30°$ C. to $100°$ C., preferably $-10°$ C. to $30°$ C. Reduction is carried out with a trialkyltin hydride such as tributyltin hydride or by catalytic reduction with use of a catalyst such as palladium on carbon or platinum oxide in an inert solvent as benzene, toluene or methanol at a temperature of $0°$ C. to $100°$ C., preferably $10°$ C. to $50°$ C.

(2) In the case of the compound in which Y represents the group $-(CO)_k-N(R^5)-Z-$, wherein Z represents a group $-(CH_2)_m-CHR^6$, where $R^6$ represents OH, but $R^5$ does not represent lower acyl:

This compound can be prepared by (a) reducing the ketone group of the compound represented by the formula (I) wherein Y represents a group $-(CO)_k-N(R^5)-(CH_2)_m-CO-$, wherein amino in $R^{10}$ and, when $R^1$ and $R^2$ contain a carboxyl group and a hydroxyl group, the carboxyl and hydroxyl group may be protected, with an appropriate reducing agent such as sodium borohydride, and removing the protective groups, if necessary, or (b) reacting the compound represented by the formula (V) with the compound represented by the following formula (VII):

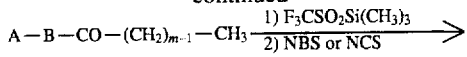

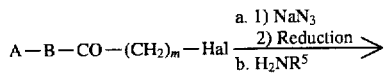

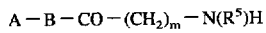

(5) In the case of the compound wherein Y represents the group —$(CO)_k$—Het—, wherein k denotes 0:

This compound can be prepared by intramolecular condensation of the Y in the compound represented by the general formula (I) wherein Y represents the group —$(CO)_k$—$N(R^5)$—$(CH_2)_m$— CO— to form a cyclic compound. Specifically, it can be prepared by reacting the corresponding compound represented by the formula (I) in the presence of an acid at a temperature of 0° to 100° C. for 1 minute to 6 hours. The suitable acid includes inorganic acids such as sulfuric acid, hydrochloric acid and hydrobromic acid, particularly sulfuric acid.

(6) In the case of the compound wherein Y represents —$(CO)_k$—Het—, wherein k=1:

This compound can be prepared according to the following scheme:

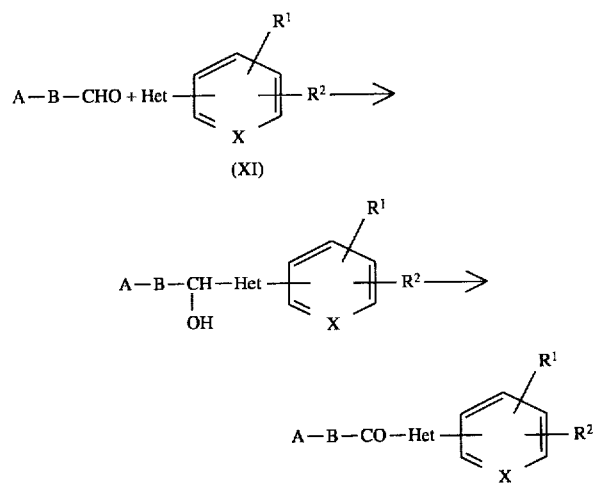

wherein $R^1$, $R^2$ and Het have the same meanings as defined in the general formula (I):

The reaction can be conducted by performing the reaction in the presence or absence of a base such as n-butyl lithium, lithium or diisopropylamide in a solvent which is not involved in a solvent at a temperature of −100° to 50° C., preferably −80° to 0° C. for 10 minutes to 12 hours, preferably 30 minutes to 6 hours, and removing the protective groups, if necessary.

The above compound of the formula (XI) can be prepared according to a well-known method, for example, described in Comprehensive Heterocyclic Chemistry, Vol. 6, 293.

(7) In the case of the compound wherein $R^7$, $R^8$ or $R^9$ represent an amidino group:

This compound can be prepared by reacting the compound represented by the formula (I), wherein $R^7$, $R^8$ and $R^9$ represent hydrogen, with the compound represented by the formula (XII):

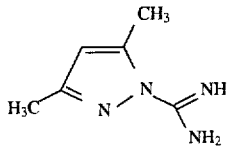

in the presence or absence of a base in an inert solvent at a temperature of −30° to 100° C., preferably −20° to 80° C. for 30 minutes to 48 hours, preferably 1 to 10 hours, and removing the protective groups, if necessary.

(8) In the case of the compound wherein Y represents the group —$(CO)_k$—$N(R^5)$—Z—, where Z represents the group —$(CH_2)_m$—CO—:

This compound can be prepared by oxidizing the hydroxyl group of the corresponding compound wherein Y represents the group —$(CO)_k$—$N(R^5)$—Z—, where Z represents the group —$(CH_2)_m$—$CHR^6$, where $R^6$ represents hydroxyl, with an appropriate oxidizing agent such as manganese dioxide, pyridinium chlorochromate or pyridinium dichromate.

In this context, it will be appreciated by one skilled in the art that in the above processes, the sequences of synthesis are determined so that no side reaction will occur in functional groups which are not involved in the reaction and that the functional groups may be protected with protective groups to avoid any undesirable reactions.

Use of the compound/pharmaceutical composition

The compound according to the present invention inhibits the aggregation of platelets by inhibiting the binding of platelet membrane protein GPIIb/IIIa and fibrinogen. Thus, the compound according to the present invention and a pharmacologically acceptable salt thereof are effective in the treatment and prophylaxis of thrombotic disorders caused by the aggregation of platelets, particularly cerebral infarction, myocardial infarction, angina pectoris or peripheral arteriocclusion.

A pharmaceutical composition comprising the compound according to the present invention or a pharmacologically acceptable salt thereof as effective ingredients can be administered human and non-human animal subjects through any one of routes such as oral or parenteral routes such as intravenous injection, intramuscular injection, subcutaneous administration, rectal administration or percutaneous administration.

Therefore, the pharmaceutical composition comprising the compound according to the present invention is processed into suitable dosage forms depending on dosage routes, and can be specifically formed into preparations mainly including injections such as intravenous injection or intramuscular injection, oral preparations such as capsule, tablet, granule, powder, pill, grains or troche, rectal preparations, oily suppositories or aqueous suppositories.

These preparations can be prepared in the usual manners with conventional additives such as an excipient, a filler, a binder, a humidifier, a disintegrating agent, a surface active agent, a lubricant, a dispersant, a buffer, a preservative, a dissolution aid, an antiseptic agent, a flavoring agent, an analgesic agent or a stabilizer. The aforementioned acceptable and non-toxic additives include, for example, lactose, fructose, glucose, starch, gelatin, magnesium carbonate, synthetic magnesium silicate, talc, magnesium stearate, methyl cellulose or a salt thereof, gum arabic, polyethylene glycol, syrup, vaseline, ethanol, propylene glycol, citric acid, sodium chloride, sodium sulfite and sodium phosphate.

The compound according to the present invention in a pharmaceutical composition is contained in amounts depending on its dosage forms, which generally range from about 1 to 70% by weight, preferably from about 5 to 50% by weight of the total composition.

The dose is appropriately determined in consideration of the use, and the age, sex and severity of a patient. The dose is generally in the range from about 0.1 to 1,000 mg, preferably from 1 to 200 mg per day to an adult patient for the purpose of the treatment of thrombotic disorders. The dose may be administered in one or more portions per day.

EXAMPLES

The present invention is now described in detail with reference to the following examples, but it should not be construed that the invention be limited thereto.

Example 1

[[4-[[[trans-4-(aminomethyl)cyclohexyl]carbonylamino]acetyl]-o-phenylene]dioxy]diacetic acid trifluoroacetate (a)     Trans-4-(t-butyloxycarbonylaminomethyl)cyclohexanecarboxylic acid To the solution of trans-4- (aminomethyl) cyclohexanecarboxylic acid (10 g, 63.6 mmole) in the mixture of 100 ml of water and 20 ml of dimethylformamide were added 9 ml of triethylamine and 22.6 ml of di-t-butyl dicarbonate, and the mixture was stirred at room temperature for 4 hours. To the reaction mixture was added 300 ml of ethyl acetate, and the resulting mixture was acidified with 1N hydrochloric acid. The organic layer was dried over anhydrous magnesium sulfate. The inorganic salt was removed by filtration, and the filtrate was concentrated under reduced pressure. Solids thus obtained were washed with n-hexane to give the title compound as colorless crystals (yield, 90%).

$^1$H-NMR (CDCl$_3$) δ:0.95–1.02 (m, 2H), 1.37–1.44 (m, 12H), 1.82 (d, 2H), 2.04 (d, 2H), 2.22–2.30 (m, 1H), 2.98 (d, 2H).

(b) Dimethyl [[4-(aminoacetyl)-o-phenylene]dioxy]diacetate trifluoroacetate b-1) To the solution of α-amino-3,4-dihydroxyacetophenone (3.0 g, 18 mmole) in 30 ml of dimethylformamide were added 4.3 ml of di-t-butyl dicarbonate and a catalytic amount of 4-dimethylaminopyridine, and the mixture was stirred at room temperature for 3 hours. After the reaction mixture was concentrated under reduced pressure, the resulting oily product was dissolved in ethyl acetate, washed with an aqueous sodium hydrogen carbonate solution and then with water, and dried over anhydrous magnesium sulfate. The inorganic salt was removed by filtration. The filtrate was concentrated under reduced pressure. The solid product thus obtained was purified by column chromatography on silica gel to give 1.3 g of α-(t-butyloxycarbonyl)amino-3,4-dihydroxyacetophenone as an orange solid (yield, 28%)

$^1$H-NMR (CDCl$_3$) δ: 1.47 (s, 9H), 4.54 (d, 2H), 6.90 (d, 1H), 7.41 (s, 1H), 7.45 (d, 1H).

b-2) To the solution of the compound obtained in b-1) (1.0 g, 3.7 mmole) in acetone were added 1.1 g of potassium carbonate and 10 ml of methyl bromoacetate, and the mixture was stirred at room temperature overnight. After the reaction mixture was concentrated under reduced pressure, the solid product thus obtained was dissolved in 200 ml of ethyl acetate, washed with water and dried over anhydrous magnesium sulfate. The inorganic salt was removed by filtration, and the filtrate was concentrated under reduced pressure. The resulting oily product was purified by column chromatography on silica gel to give 1.5 g of dimethyl [[4-[((t-butyl-oxycarbonylamino)acetyl]-o-pheylene]dioxy] diacetate as an orange oily product (yield, 100%).

$^1$H-NMR (CDCl$_3$) δ: 1.47 (s, 9H), 3.80 (s, 3H), 3.81 (s, 3H), 4.58 (d, 2H), 4.78 (s, 2H), 4.81 (s, 2H), 6.86 (d, 1H), 7.51 (s, 1H), 7.58 (d, 1H).

b-3) To the solution of the compound prepared in b-2) (1.5 g, 3.7 mmole) in 15 ml of dichloromethane were added 4 ml of anisole and 5.6 ml of trifluoroacetic acid, and the mixture was stirred at room temperature for 1 hour. After the reaction mixture was concentrated under reduced pressure, the resulting solids were washed with ether to give 1.2 g of the title compound as pale yellow powder (yield, 79%).

$^1$H-NMR (CD$_3$OD) δ: 3.78 (s, 3H), 3.79 (s, 2H), 4.52 (s, 2H), 4.85 (s, 2H), 4.91 (s, 2H), 7.07 (d, 2H), 7.60 (d, 1H), 7.70 (dd, 1H).

(c) To the solution of 877 mg (3.41 mmol) of the compound prepared in (a) (3.41 mmole) in the mixture of 6.8 ml of dimethylformamide and 1.4 ml of pyridine were added 874 mg of N,N'-disuccinimidyl carbonate and a catalytic amount of 4-dimethylaminopyridine, and the resulting mixture was stirred at room temperature for 3 hours, whereafter 1.45 g of the compound prepared in (b) and 0.59 ml of N,N-diisopropylethylamine were added. The mixture was further stirred at room temperature overnight. After the reaction mixture was concentrated under reduced pressure, the resulting solid product was purified by column chromatography on silica gel. The solid product thus obtained was washed with ether to give 1.1 g of dimethyl [[4-[[[trans-4-(t-butyloxycarbonylaminomethyl)cyclohexyl]carbonylamino]acetyl]-o-phenylene]dioxy]diacetate as pale yellow crystals (yield, 59%).

$^1$H-NMR (CDCl$_3$) δ: 0.90–1.10 (m, 2H), 1.44–1.56 (m, 12H), 1.86 (d, 2H), 1.98 (d, 2H), 2.14–2.22 (m, 1H), 3.05–3.10 (m, 2H), 3.81 (s, 6H), 4.76 (d, 2H), 4.78 (s, 2H), 4.81 (s, 2H), 6.55 (t, 1H), 6.87 (d, 1H), 7.51 (d, 1H), 7.61 (dd, 1H).

(d) To the suspension of 300 mg (0.55 mmole) of the compound prepared in (c) in 3 ml of methanol was added 3 ml of 1N potassium hydroxide, and the mixture was stirred under ice-cooling for 15 minutes. After methanol was evaporated under reduced pressure, ethyl acetate and water were added to the residue, and the mixture was acidified with 1N hydrochloric acid. After the organic layer was dried over magnesium sulfate, the inorganic salt was removed by filtration. The filtrate was concentrated under reduced pressure. Solids thus obtained were washed with ether to give 243 mg of [[4-[[[trans-4-(t-butyloxycarbonylaminomethyl)cyclohexyl]carbonylamino]acetyl]-o-phenylene]dioxy]diacetic acid as pale yellow powder.

$^1$H-NMR (CDCl$_3$) δ: 0.98–1.04 (m, 2H), 1.44–1.54 (m, 12H), 1.84–1.98 (m, 4H), 2.17–2.20 (m, 1H), 2.97 (d, 2H), 4.65 (s, 2H), 4.75 (s, 2H), 4.77 (s, 2H), 6.91 (d, 1H), 7.51 (d, 1H), 7.61 (dd, 1H).

(e) To the solution of 193 mg (0.37 mmole) of the compound prepared in (d) in 2 ml of dichloromethane were added 0.6 ml of trifluoroacetic acid and 0.4 ml of anisole, and the mixture was stirred at room temperature for 1.5 hours. After the reaction mixture was concentrated under reduced pressure, the solid product thus obtained was washed with ether to give 190 mg of the title compound as yellow powder (yield, 96%).

$^1$H-NMR (CD$_3$OD) δ: 1.09–1.20 (m, 2H), 1.49–1.70 (m, 3H), 1.89 –2.05 (m, 4H), 2.30–2.38 (m, 1H), 2.79 (d, 2H), 4.63 (s, 2H), 4.78 (s, 2H), 4.83 (s, 2H), 7.05 (d, 1H), 7.58 (d, 1H), 7.70 (dd, 1H). FDMS (m/z): 423 (M$^+$+1).

Example 2

[[4-[[[trans-4-(methylaminomethyl)cyclohexyl]carbonylamino]acetyl]-o-phenylene]dioxy]diacetic acid trifluoroacetate (a) To the solution of 516 mg (2 mmole) of the compound prepared in Example 1(a) in 10 ml of dimethylformamide were added 1 ml of methyl iodide and 1.85 g of silver oxide, and the mixture was stirred at 45° C. for 7 hours and then at room temperature overnight. After insolubles were removed by filtration, chloroform was added. The mixture was washed thrice with water and dried over anhydrous magnesium sulfate. The inorganic salt was removed by filtration, and the filtrate was concentrated under reduced pressure. The oily product thus obtained was purified by column chromatography on silica gel to give 114 mg of methyl trans-4-(N-t-butyloxycarbonyl-N-methyl)aminomethylcyclohexanecarboxylate as a colorless oil (yield, 20%).

$^1$H-NMR (CDCl$_3$) δ: 0.95–1.03 (m, 2H), 1.40–1.50 (m, 12H), 1.75 (d, 2H), 2.01 (d, 2H), 2.25 (m, 1H), 2.85 (s, 2H), 3.06 (s, 3H), 3.67 (s, 3H).

(b) To the solution of 352 mg (1.23 mmole) of the compound prepared in (a) in 6 ml of methanol was added 6 ml of 1N sodium hydroxide, and the mixture was stirred at room temperature for 1.5 hours. After the solution was concentrated under reduced pressure, chloroform and water were added to the residue. After the mixture was acidified with 1N hydrochloric acid, the organic layer was dried over anhydrous magnesium sulfate. The inorganic salt was removed by filtration. The filtrate was then concentrated under reduced pressure. The oily product thus obtained was purified by column chromatography on silica gel to give 300 mg of trans-4-(N-t-butyloxycarbonyl-N-methyl)aminomethylcyclohexanecarboxylic acid as a colorless oily material (yield, 90%).

$^1$H-NMR (CDCl$_3$) δ: 0.95–1.03 (m, 2H), 1.40–1.48 (m, 12H), 1.77 (d, 2H), 2.04 (d, 2H), 2.27 (m, 1H), 2.85 (s, 2H), 3.06 (s, 3H). (c) According to the method of Example 1(c), 211 mg of dimethyl [[4-[[[trans-4-[(N-methyl-N-t-butyloxycarbonyl)aminomethyl]cyclohexyl]carbonylamino]acetyl]-o-phenylene]dioxy]diacetate was obtained from 135 mg of the compound prepared in Example 1(b) (0.5 mmole) and 210 mg of the compound prepared in Example 1(b) (yield, 75%).

$^1$H-NMR (CDCl$_3$) δ: 1.00 (m, 2H), 1.45–1.52 (m, 12H), 1.78 (d, 2H), 1.98 (d, 2H), 2.19 (m, 1H), 2.85 (s, 2H), 3.07 (bs, 3H), 3.81 (s, 6H), 4.68 (d, 2H), 4.79 (s, 2H), 4.82 (s, 2H), 6.54 (bs, 1H), 6.87 (d, 1H), 7.51 (d, 1H), 7.61 (dd, 1H).

(d) According to the method of Example 1(d), 123 mg of [[4-[[[trans-4-[(N-methyl-N-t-butyloxycarbonyl)aminomethyl]cyclohexyl]carbonylamino]acetyl]-o-phenylene]dioxy]diacetic acid was obtained from 210 mg (0.37 mmole) of the compound prepared in (c) (yield, 62%).

$^1$H-NMR (CDCl$_3$) δ: 1.02 (m, 2H), 1.45–1.65 (m, 12H), 1.78 (m, 2H), 1.97 (m, 2H), 2.22 (m, 2H), 2.84 (s, 2H), 3.07 (bs, 3H), 4.65 (s, 2H), 4.74 (d, 2H), 4.77 (d, 2H), 6.91 (d, 1H), 7.52 (d, 1H), 7.63 (dd, 1H).

(e) According to the method of Example 1(e), 89 mg of the title compound was obtained from 100 mg (0.2 mmole) of the compound prepared in (d) (yield, 87%).

$^1$H-NMR (CD$_3$OD) δ: 1.12 (m, 2H), 1.50–1.70 (m, 3H), 1.90–2.00 (m, 4H), 2.33 (m, 1H), 2.70 (s, 3H), 2.86 (d, 2H), 4.63 (s, 2H), 4.78 (s, 2H), 4.83 (s, 2H), 7.03 (d, 1H), 7.58 (d, 1H), 7.68 (dd, 1H).

Example 3

[[4-[[[trans-4-(guanidinomethyl)cyclohexyl]carbonylamino]acetyl]-o-phenylene]dioxy]diacetic acid To the solution of 70 mg (0.13 mmole) of the compound in Example 1 in 0.1 ml of concentrated aqueous ammonia was added 20 mg of methyl isothiourea sulfate, and the mixture was stirred at room temperature overnight. After methanol was added to the reaction mixture, crystals were collected by filtration and dried to give 39 mg of the title compound (yield, 64%).

$^1$H-NMR (D$_2$O) δ: 1.05–1.20 (m, 2H), 1.42–1.65 (m, 3H), 1.88–2.00 (m, 4H), 2.35–2.42 (m, 1H), 3.08 (d, 2H), 4.67 (s, 2H), 4.71 (s, 2H), 4.73 (s, 2H), 7.02 (d, 1H), 7.45 (s, 1H), 7.73 (d, 1H). FDMS (m/z): 465 (M$^+$+1).

Example 4

2-(4-aminomethylcyclohexyl)-5-(3,4-dicarboxymethoxy)phenyloxazole

To 150 mg (0.28 mmole) of the compound of Example 1 was added 0.3 ml of concentrated sulfuric acid, and the mixture was stirred at room temperature for 5 minutes. After a small amount of water was added to the reaction mixture, the resulting mixture was purified on HP-20 and then lyophilized to give 33 mg of the title compound as colorless powder (yield, 29%). FDMS (m/z): 405 (M$^+$+1).

Example 5

[[4-[[[trans-4-(acetylaminomethyl)cyclohexyl]carbonylamino]acetyl]-o-phenylene]dioxy]diacetic acid disodium salt (a) To the solution of 550 mg (1 mmole) of the compound prepared in Example 1(c) in 5.5 ml of dichloromethane were added 1.1 ml of anisole and 2 ml of trifluoroacetic acid, and the mixture was stirred at room temperature. The reaction mixture was concentrated under reduced pressure and then dried thoroughly to give a quantitative amount of dimethyl [[4-[[[trans-4-(aminomethyl)cyclohexyl]carbonylamino]acetyl]-o-phenylene]dioxy]diacetate trifluoroacetic acid salt. The oily product unpurified was used directly for the following reaction.

(b) To 205 mg (0.36 mmole) of the compound prepared in (a) were added 2 ml of pyridine and 1 ml of acetic anhydride, and the mixture was stirred at room temperature overnight. After ethyl acetate was added to the reaction mixture, the mixture was washed with water and then dried over anhydrous magnesium sulfate. The inorganic salt was removed by filtration. The filtrate was concentrated under reduced pressure. The oily product thus obtained was purified by column chromatography on silica gel to give 92 mg of dimethyl [[4-[[[trans-4-(acetylaminomethyl)cyclohexyl]carbonylamino]acetyl]-o-phenylene]dioxy]diacetate as pale yellow crystals (yield, 51%).

$^1$H-NMR (CDCl$_3$) δ: 1.00–1.10 (m, 2H), 1.47–1.55 (m, 3H), 1.86 (m, 2H), 1.97–2.03 (m, 5H), 3.13 (t, 2H), 3.81 (s, 6H), 4.68 (d, 2H), 4.79 (s, 2H), 4.81 (s, 2H), 5.51 (bs, 1H), 6.56 (bs, 1H), 6.87 (d, 1H), 7.51 (d, 1H), 7.62 (dd, 1H).

(c) To the suspension of 92 mg (0.19 mmole) of the compound prepared in (b) in 2 ml of methanol was added 1 ml of 1N sodium hydroxide, and the mixture was stirred at a temperature from under ice-cooling to room temperature for 1 hour. After the reaction mixture was concentrated under reduced pressure, the residue thus obtained was purified on HP-20 and then lyophilized to give 44 mg of the title compound (yield, 46%).

$^1$H-NMR (D$_2$O) δ: 1.00–1.10 (m, 2H), 1.38–1.50 (m, 3H), 1.80–1.85 (m, 2H), 1.90–1.95 (m, 2H), 2.00 (s, 3H), 2.30–2.45 (m, 1H), 3.06 (d, 2H), 4.62 (s, 2H), 4.70 (s, 2H), 6.97 (d, 1H), 7.41 (s, 1H), 7.70 (d, 1H).

Example 6

[[4-[[[trans-4-[(p-amidinobenzoyl)aminomethyl]-cyclohexyl]carbonylamino]acetyl]-o-phenylene]dioxy]diacetic acid disodium salt (a) To the solution of 470 mg (0.83 mmole) of the compound prepared in Example 5 (a) in 5 ml of dimethylformamide were added 0.23 ml of triethylamine and 138 mg of 4-cyanobenzoyl chloride, and the mixture was stirred at room temperature for 1 hour. After the reaction mixture was concentrated under reduced pressure, the residue thus obtained was dissolved in chloroform, washed with water and dried over anhydrous magnesium sulfate. After the inorganic salt was removed by filtration, the filtrate was concentrated under reduced pressure. The solid product thus obtained was washed with ether to give 300 mg of dimethyl [[4-[[[trans-4-[(p-cyanobenzoyl)aminomethyl]cyclohexyl]carbonylamino]acetyl]-o-phenylene]dioxy]diacetate (yield, 62%).

$^1$H-NMR (CDCl$_3$) δ: 1.05–1.15 (m, 2H), 1.50–1.62 (m, 3H), 1.88–2.05 (m, 4H), 2.15–2.22 (m, 1H), 3.34–3.37 (m, 2H), 3.81 (s, 6H), 4.67 (d, 2H), 4.78 (s, 2H), 4.81 (s, 2H), 6.24 (bs, 1H), 6.55 (bs, 1H), 6.87 (d, 1H), 7.51 (s, 1H), 7.60 (d, 1H), 7.74 (d, 2H), 7.87 (d, 2H).

(b) To the solution of 350 mg (0.6 mmole) of the compound prepared in (a) in the mixture of 15 ml of pyridine and 1 ml of triethylamine, and hydrogen sulfide gas was streamed into the mixture under ice-cooling for 30 minutes before the resulting mixture was stirred at room temperature overnight. The reaction mixture was diluted with ethyl acetate, washed with a 5% sodium hydrogen carbonate solution followed by a 1M potassium hydrogen sulfate solution, and dried over anhydrous magnesium sulfate. After the inorganic salt was removed by filtration, the filtrate was concentrated under reduced pressure. The residue thus obtained was purified by column chromatography on silica gel to give 288 mg of dimethyl [[4-[[[trans-4-[(p-thiocarbamoylbenzoyl) aminomethyl]cyclohexyl]carbonylamino] acetyl]-o-phenylene]dioxy]diacetate as a yellow foam product (yield, 78%).

$^1$H-NMR (CDCl$_3$) δ: 1.05–1.15 (m, 2H), 1.48–1.70 (m, 3H), 1.86–2.01 (m, 4H), 2.18–2.25 (m, 1H), 3.34 (t, 2H), 3.81 (s, 6H), 4.66 (d, 2H), 4.79 (s, 2H), 6.54 (m, 1H), 6.64 (m, 1H), 6.87 (d, 1H), 7.52 (d, 1H), 7.61 (dd, 1H), 7.77 (d, 2H), 7.90 (d, 2H).

(c) To the solution of 288 mg (0.47 mmole) of the compound prepared in (b) in 15 ml of acetone was added 3 ml of methyl iodide, and the mixture was refluxed for 1 hour. After the reaction mixture was concentrated under reduced pressure, the residue thus obtained was purified by column chromatography on silica gel to give 201 mg of dimethyl [[4-[[[trans-4-[[p-(1-methylthio-1-imino)methyl]benzoyl] aminomethyl]cyclohexyl]carbonylamino]acetyl]-o-phenylene]dioxy]diacetate as pale yellow crystals (yield, 68%).

$^1$-NMR (CDCl$_3$) δ: 1.09–1.20 (m, 2H), 1.50–1.60 (m, 3H), 1.92–2.03 (m, 4H), 2.45 (s, 3H), 3.35 (t, 2H), 3.81 (s, 6H), 4.67 (d, 2H), 4.79 (s, 2H), 4.82(s, 2H), 6.35 (m, 1H), 6.60 (m, 1H), 6.87 (d, 1H), 7.51 (s, 1H), 7.61 (d, 1H), 7.82 (m, 4H).

(d) To the solution of 150 mg (0.24 mmole) of the compound prepared in (c) in 3 ml of methanol was added 3t mg of ammonium acetate, and the mixture was refluxed for 5.5 hours. Deposited solids were collected by filtration to give 44 mg of dimethyl [[4-[[[trans-4-[(p-amidinobenzoyl)aminomethyl]cyclohexyl]carbonylamino]acetyl]-o-phenylene]dioxy]diacetate (yield, 31%).

$^1$-NMR (CDCl$_3$) δ: 1.05–1.14 (m, 2H), 1.49–1.68 (m, 3H), 1.91–2.01 (m, 4H), 2.20–2.38 (m, 1H), 3.32 (d, 2H), 3.82 (s, 6H), 4.66 (s, 2H), 4.79 (s, 2H), 4.82(s, 2H), 6.87 (d, 1H), 7.52 (d, 1H), 7.63 (dd, 2H), 7.75 (d, 2H), 7.91 (d, 2H).

(e) To the solution of 40 mg (0.07 mmole) of the compound prepared in (d) in 2 ml of methanol was added 1 ml of 1N sodium hydroxide, and the mixture was stirred at a temperature from ice-cooling to room temperature for 6 hours. After the reaction mixture was concentrated under reduced pressure, the residue thus obtained was purified on HP-20 and then lyophilized to give 22 mg of the title compound.

$^1$-NMR (D$_2$O) δ: 1.10–1.20 (m, 2H), 1.47–1.52 (m, 2H), 1.69 (m, 1H), 1.92–2.00 (m, 4H), 2.40 (m, 1H), 3.32 (d, 2H), 4.64 (s, 2H), 4.68 (s, 2H), 4.72 (s, 2H), 7.00 (d, 1H), 7.43 (s, 1H), 7.72 (d, 1H), 7.88–7.94 (d, 4H).

Example 7

[[4-[[2-[trans-4-(aminomethyl)cyclohexyl]carbonylamino]ethyl]-o-phenylene]dioxy]diacetic acid trifluoroacetate The title compound as a colorless crystal was prepared from 130 mg of the compound obtained in Example 1 (a) and 220 mg of diethyl [[4-(2-aminoethyl)-o-phenylene]dioxy]diacetate according to the process described in Example 1 (c)–(e).

$^1$H-NMR (CD$_3$OD) δ: 1.00–1.08 (m, 2H), 1.42–1.65 (m, 3H), 1.80–1.88 (m, 4H), 2.07–2.15 (m, 1H), 2.71 (t, 2H), 2.77 (d, 2H), 3.31 (m, 2H), 3.36 (t, 2H), 4.68 (s, 2H), 4.71 (s, 2H), 6.78 (dd, 1H), 6.85 (d, 1H), 6.90 (d, 1H).

Example 8

[[4-[[[trans-4-(aminomethyl)cyclohexyl]carbonyl](N-methyl)amino]acetyl]-o-phenylene]dioxy]diacetic acid trifluoroacetate $^1$H-NMR (CD$_3$OD) δ: 1.12 (m, 3H), 1.45–1.70 (m, 3H), 1.81 (d, 1H), 1.96 (t, 3H), 2.72, 2.78 (2d, 2H), 2.94, 3.16 (2s, 3H), 4.77, 4.79 (2s, 2H), 4.82, 5.01 (2s, 2H), 4.83, 4.84 (2s, 2H), 7.02, 7.04 (t, 1H), 7.56, 7.60 (2d 1H), 7.68, 7.72 (2dd, 1H). SIMS (m/z ): 437 (M$^+$+1).

Example 9

[[4-[[N-[3-(piperidin-4-yl)propionyl]-N-methylamino]-acetyl]-o-phenylene]dioxy]diacetic acid trifluoroacetate (a) Di-t-butyl [[4-[[N-[3-(1-t-butyloxycarbonylpiperidin-4-yl)propionyl]-N-methylamino]acetyl]-o-phenylene]dioxy]diacetate 3-(1-t-butyloxycarbonylpiperidin-4-yl)propionic acid (257 mg), di-t-butyl [[4-[(N-methylamino)acetyl]-o-phenylene]dioxy]diacetate hydrochloride (446 mg), N-methylmorpholine (101 mg), benzotriazol-1-yloxytris(dimethylamino)phosphonium hexafluorophosphate (BOP reagent, 442 mg), and a catalytic amount of 4-dimethylaminopyridine were dissolved in 5 ml of dimethylformamide, and the mixture was stirred at room temperature for 3 hours. After ethyl acetate (100 ml) was added to the reaction mixture, the resulting mixture was washed with water. The solvents were removed under reduced pressure. The residual mixture was purified by column chromatography on silica gel to give 285 mg of the title compound from the fraction eluted with n-hexan:ethyl acetate=3:1.

$^1$H-NMR (CDCl$_3$) δ: 1.04–1.15 (m, 2H), 1.38–1.54 (m, 28H), 1.54–1.75 (m, 4H), 2.35–2.48 (m, 2H), 2.58–2.75 (m, 2H), 3.08 (s, 3H), 3.98–4.29 (m, 2H), 4.62 (s, 2H), 4.66 (s, 2H), 4.77 (s, 2H), 6.82 (d, J=8 Hz, 1H), 7.47 (s, 1H), 7.60 (d, J=8 Hz, 1H). SIMS (m/z): 649 (M$^+$+1).

(b) The solution of 250 mg of the compound prepared in (a) in 2 ml of trifluoroacetic acid was stirred at room temperature for 3 hours. After the solvent was evaporated under reduced pressure, ether was added and deposited crystals were collected by filtration to give 168 mg of the title compound.

$^1$H-NMR (D$_2$O) δ: 1.22–1.45 (m, 2H), 1.48–1.68 (m, 3H), 1.77–2.02 (m, 2H), 2.40–2.60 (m, 2H), 2.85–3.02 (m, 2H), 2.96, 3.13 (s, 3H), 3.29–3.45 (m, 2H), 4.82–5.06 (m, 6H), 7.02–7.08 (m, 1H), 7.45–7.48 (m, 1H), 7.66–7.75 (m, 1H). SIMS (m/z): 437 (M$^+$+1).

Example 10

[[4-[[N-[3-(piperidin-4-yl)propionyl]amino]acetyl]-o-phenylene]dioxy]diacetic acid trifluoroaceetate (a) Di-t-butyl[[4-[[N-[3-(1-t-butyloxycarbonylpiperidin-4-yl)propionyl]amino]acetyl]-o-phenylene]dioxy]diacetate 3-(1-t-butyloxycarbonylpiperidin-4-yl)propionic acid (423 mg), di-t-buty [[4-(aminoacetyl)-o-phenylene]dioxy] diacetate (650 mg), N-methylmorpholine (167 mg), benzotriazol-1-yloxytris(dimethylamino)phosphonium hexafluorophosphate (BOP reagent, 730 mg) and a catalytic amount of 4-dimethylaminopyridine were dissolved in 10 ml of dimethylformamide and treated in the same manner as described in Example 9 (a) to give the title compound (485 mg) from the fraction eluted with n-hexane:ethyl acetate= 2:1.

$^1$H-NMR (CDCl$_3$) δ: 1.05–1.18 (m, 2H), 1.45 (s, 9H), 1.48 (s, 9H), 1.50 (s, 9H), 1.58–1.70 (m, 5H), 2.30–2.37 (m, 2H), 2.62–2.72 (m, 2H), 4.02–4.17 (m, 2H), 4.66 (s, 2H), 4.69 (s, 4H), 6.53 (brs, 1H), 6.83 (d, J=9 Hz, 1H), 7.48 (s, 1H), 7.60 (d, J=9 Hz, 1H). FDMS (m/z): 634 (M+).

(b) The compound prepared in (a) (480 mg) was dissolved in 5 ml of trifluoroacetic acid and treated in the same manner as described in Example 9 (b) to give the title compound (380 mg).

$^1$H-NMR (D$_2$O) δ: 1.32–1.44 (m, 2H), 1.53–1.67 (m, 3H), 1.88–1.98 (m, 2H), 2.34–2.45 (m, 2H), 2.90–3.02 (m, 2H), 3.34–3.47 (m, 2H), 4.65 (s, 2H), 4.84 (s, 2H), 4.88 (s, 2H), 7.04 (d, J=9 Hz, 1H), 7.45 (s, 1H), 7.66 (d, J=9 Hz, 1H). SIMS (m/z): 423 (M$^+$+1).

Example 11

[[4-[[(piperidin-4-yl) acetylamino]acetyl]-o-phenylene]dioxy]diacetic acid trifluoroacetate The title compound was prepared in the same manner as in Example 9.
(a) Di-t-butyl [[4-[[(1-t-butyloxycarbonylpiperidin-4-yl)acetylamino]acetyl-o-phenylene]dioxy]diacetate $^1$H-NMR (CDCl$_3$) δ: 1.25 (m, 2H), 1.45 (s, 9H), 1.48 (s, 9H), 1.50 (s, 9H), 1.70 (m, 2H), 2.00 (m, 1H), 2.25 (m, 2H), 2.72 (m, 2H), 4.09 (brs, 2H), 4.66 (s, 2H), 4.69 (s, 2H), 4.70 (s, 2H), 6.56 (brs, 1H), 6.83 (d, 1H), 7.47 (d, 1H), 7.59 (dd, 1H). FDMS (m/z): 620 (M$^+$).

(b) [[4-[[(piperidin-4-yl)acetylamino]acetyl]-o-phenylene] dioxy]diacetic acid trifluoroacetate $^1$H-NMR (D$_2$O) δ: 1.50 (m, 2H), 1.95–2.15 (m, 3H), 2.39 (m, 2H), 3.05 (m, 2H), 3.45 (d, 2H), 4.70 (s, 2H), 4.83 (s, 2H), 4.86 (s, 2H), 7.06 (d, 1H), 7.48 (s, 1H), 7.70 (d, 1H).

Example 12

[[4-[[[4-(piperidin-4-yl)butyryl]amino]acetyl]-o-phenylene]dioxy]diacetic acid trifluoroacetate The title compound was prepared in the same manner as in Example 9.
(a) Di-t-butyl [[4-[[[4-(1-t-butyloxycarbonylpiperidin-4-yl)butyryl]amino]acetyl-o-phenylene]dioxy]diacetate $^1$H-NMR (CDCl$_3$) δ: 1.04 (m, 2H), 1.28 (s, 2H), 1.45 (s, 9H), 1.48 (s, 9H), 1.50 (s, 2H), 1.60–1.72 (m, 5H), 2.30 (m, 2H), 2.67 (m, 2H), 4.07 (brs, 1H), 4.66 (s, 2H), 4.69 (s, 2H), 4.70 (s, 2H), 6.54 (brs, 1H), 6.83 (d, 1H), 7.58 (d, 1H), 7.60 (d, 1H). FDMS (m/z): 649 (M$^+$+1).
(b) [[4-[[[4-(piperidin-4-yl)butyryl]amino]acetyl]-o-phenylene]dioxy]diacetic acid trifluoroacetate $^1$H-NMR (D$_2$O) δ: 1.25–1.40 (m, 4H), 1.52–1.68 (m, 3H), 1.93 (d, 2H), 2.38 (m, 2H), 2.96 (t, 2H), 3.40 (d, 2H), 4.66 (s, 2H), 4.85 (s, 2H), 4.89 (s, 2H), 7.06 (d, 1H), 7.48 (d, 1H), 7.70 (dd, 1H).

Example 13

[[4-[[[(4,5,6,7-tetrahydrothieno[3,2-c]pyridin-2-yl)-carbonyl]amino]acetyl]-o-phenylene]dioxy]diacetic acid trifluoroacetate The title compound was prepared in the same manner as in Example 9.
(a) Di-t-butyl [[4-[[[(5-t-butyloxycarbonyl-4,5,6,7-tetrahydrothieno[3,2-c]pyridin-2-yl)carbonyl]amino]acetyl-o-phenylene]dioxy]diacetate $^1$H-NMR (CDCl$_3$) δ: 1.48–1.58 (m, 27H), 2.87 (brs, 2H), 3.73 (brs, 2H), 4.49 (s, 2H), 4.67 (s, 2H), 4.70 (s, 2H), 4.84 (d, 2H), 6.85 (d, 1H), 7.08 (brs, 1H), 7.33 (s, 1H), 7.50 (d, 1H), 7.63 (q, 1H).
(b) [[4-[[[(4,5,6,7-tetrahydrothieno [3,2-c]pyridin-2-yl)carbonyl]amino]acetyl]-o-phenylene]dioxy]diacetic acid trifluoroacetate $^1$H-NMR (DMSO-d$_6$) δ: 3.08 (m, 2H), 3.37–3.61 (m, 2H), 4.24 (s, 2H), 4.70 (m, 2H), 4.79 (s, 2H), 4.85 (s, 2H), 7.02 (d, 1H), 7.42 (d, 1H), 7.60 (s, 1H), 7.70 (q, 1H), 8.82 (brs, 1H), 9.09 (brs, 1H).

Example 14

[[4-[[(piperidin-4-yl)carbonyl]amino]acetyl]-o-phenylene]dioxy]diacetic acid trifluoroacetate The title compound was prepared in the same manner as in Example 9.
(a) Di-t-butyl [[4-[[(1-t-butyloxycarbonylpiperidin-4-yl)carbonylamino]acetyl-o-phenylene]dioxy]diacetate $^1$H-NMR (CDCl$_3$) δ: 1.48 (m, 27H), 1.72 (m, 2H), 1.87 (d, 2H), 2.38 (m, 1H), 2.77 (m, 2H), 4.18 (m, 2H), 4.66 (s, 2H), 4.67 (s, 2H), 4.69 (s, 2H), 6.60 (brs, 1H), 6.83 (d, 1H), 7.47 (d, 1H), 7.58 (dd, 1H). FDMS (m/z): 606 (M$^+$).

(b) [[4-[[(piperidin-4-yl)carbonyl]amino]acetyl]-o-phenylene]dioxy]diacetic acid trifluoroacetate $^1$H-NMR (D$_2$O) δ: 1.91 (m, 2H), 2.15 (m, 2H), 2.80 (m, 1H), 3.14 (m, 2H), 3.53 (m, 2H), 4.70 (s, 2H), 4.86 (s, 2H), 4.90 (s, 2H), 7.06 (d, 1H), 7.48 (s, 1H), 7.69 (d, 1H). FDMS (m/z): 395 (M$^+$+1).

Example 15

[[4-[2-[3-(piperidin-4-yl)propionyl]aminoethyl]-o-phenylene]dioxy]diacetic acid trifluoroacetate The title compound was prepared in the same manner as in Example 9 except that the following process (b) was further carried out.

(a) Diethyl [[4-[2-[3-(1-t-butyloxycarbonylpiperidin-4-yl)propionyl]aminoethyl]-o-phenylene]dioxy]diacetate $^1$H-NMR (CDCl$_3$) δ: 1.15 (m, 2H), 1.28 (m, 6H), 1.45 (s, 9H), 1.56–1.70 (m, 3H), 2.15 (m, 2H), 2.60–2.78 (m, 4H), 3.46 (m, 2H), 4.07 (brs, 2H), 4.25 (m, 4H), 4.69 (s, 2H), 4.71 (s, 2H), 5.45 (brs, 1H), 6.74–6.83 (m, 3H).

(b) [[4-[2-[3-(1-t-butyloxycarbonylpiperidin-4-yl)propionyl]aminoethyl]-o-phenylene]dioxy]diacetic acid $^1$H-NMR (CDCl$_3$) δ: 1.05 (m, 2H), 1.44 (s, 9H), 1.58 (m, 3H), 2.15 (m, 2H), 2.60–2.70 (m, 4H), 3.42 (m, 4H), 3.96–4.30 (m, 4H), 4.67 (s, 2H), 4.68 (s, 2H), 6.68–6.80 (m, 3H).

The compound obtained in the above process (a) (150 mg) was hydrolyzed with 1.3 ml of 1N sodium hydroxide to give 121 mg of the title compound.

(c) [[4-[2-[3-(piperidin-4-yl)propionyl]aminoethyl]-o-phenylene]dioxy]diacetic acid trifluoroacetate $^1$H-NMR (CDCl$_3$) δ: 1.25–1.40 (m, 3H), 1.49 (m, 2H), 1.82 (m, 2H), 2.17 (m, 2H), 2.74 (m, 2H), 2.88 (m, 2H), 3.42 (m, 2H), 4.69 (s, 2H), 4.72 (s, 2H), 6.83–6.90 (m, 3H).

Example 16

[[4-[2-[(4,5,6,7-tetrahydrothieno[3,2-c]pyridin-2-yl)carbonyl]aminoethyl]-o-phenylene]dioxy]diacetic acid trifluoroacetate The title compound was prepared in the same manner as in Example 15.

(a) Diethyl [[4-[2-[(5-t-butyloxycarbonyl-4,5,6,7-tetrahydrothieno[3,2-c]pyridin-2-yl)carbonyl]aminoethyl]-o-phenylene]dioxy]diacetate H-NMR (CDCl$_3$) δ: 1.25–1.30 (m, 6H), 1.48 (s, 9H), 2.79–2.82 (m, 4H), 3.58 (q, 2H), 3.70 (m, 2H), 4.18–4.27 (m, 4H), 4.42 (s, 2H), 4.68 (d, 4H), 6.75–6.83 (m, 3H), 7.17 (s, 1H).

(b) [[4-[2-[(4,5,6,7-tetrahydrothieno[3,2-c]pyridin-2-yl)carbonyl]aminoethyl]-o-phenylene]dioxy]diacetic acid trifluoroacetate $^1$H-NMR (DMSO-d$_6$) δ: 2.73 (m, 2H), 3.04 (brs, 2H), 3.36–3.39 (m, 4H), 4.14 (brs, 2H), 4.40 (brs, 2H), 4.47 (brs, 2H), 6.75–6.83 (m, 3H), 7.54 (s, 1H), 8.59 (brs, 1H).

Example 17

[[4-[[(1-amidinopiperidin-4-yl)carbonylamino]acetyl]-o-phenylene]dioxy]diacetic acid The compound prepared in Example 14 (50 mg) was dissolved in concentrated aqueous ammonia, methyl isothiourea sulfate (16 mg) was added to the solution. The mixture was stirred at room temperature overnight. After methanol was added to the reaction mixture, the resulting mixture was stirred at room temperature for a while, filtered under reduced pressure to give 24 mg of the title compound as pale yellow powder (yield, 55%).

$^1$H-NMR (D$_2$O) δ: 1.68 (m, 2H), 1.96 (m, 2H), 2.75 (m, 1H), 3.19 (m, 2H), 3.87 (m, 2H), 4.61 (s, 2H), 4.65 (s, 2H), 4.68 (s, 2H), 6.95 (d, 1H), 7.37 (s, 1H), 7.67 (d, 1H). FDMS (m/z): 437 (M$^+$+1).

Referenctial Example 1

5-t-butoxycarbonyl-4,5,6,7-tetrahydrothieno[3,2-c]-pyridin-2-carboxylic acid

To the solution of 4,5,6,7-tetrahydrothieno[3,2-c]pyridin-2-carboxylic acid (7.6 g) in DMF (75 ml) was added di-t-butyl dicarbonate (9.6 ml), and triethylamine (5.8 ml) was titrated to the mixture. After stirring at room temperature for 3 hours and the addition of water, the reaction mixture was acidified with 1N hydrochloric acid and extracted with ethyl acetate. After the organic layer was washed with water, dried over anhydrous magnesium sulfate, the solvent was evaporated. After n-hexan and a small amount of ether were added to the residue, crystals deposited were collected by filtration to give 9.36 g of the title compound (yield, 80%).

$^1$H-NMR (CDCl$_3$) δ: 1.49 (s, 9H), 2.90 (brs, 2H), 3.74 (brs, 2H), 4.51 (brs, 2H), 7.56 (s, 1H). SIMS (m/z): 284 (M$^+$+1).

Referential Example 2

5-t-butoxycarbonyl-3-methyl-4,5,6,7-tetrahydrothieno[3,2-c]pyridin-2-carboxylic acid The compound prepared in Referential Example 1 (300 mg) was dissolved in THF (5 ml), and the mixture was cooled to −78° C. After n-butyl lithium (15% hexane solution, 1.5 ml) was added, the mixture was stirred at −78° C. for 1 hour. Methyl iodide (0.16 ml) was added to the mixture that was then further stirred with heating to room temperature for 1.5 hours. After ethyl acetate and water were added to the reaction mixture, the resulting mixture was acidified with 1N hydrochloric acid. The organic layer was washed with water and dried over anhydrous magnesium sulfate. The solvent was removed by distillation. The residue was purified by column chromatography on silica gel to give 153 mg of the title compound from the fraction eluted with chloroform:methanol=20:1.

$^1$H-NMR (CDCl$_3$) δ: 1.50 (s, 9H), 2.43 (s, 3H), 2.85 (brs, 2H), 3.72 (brs, 2H), 4.38 (brs, 2H). SIMS (m/z): 298 (M$^+$+1).

Referential Example 3

5-t-butoxycarbonyl-3-benzyl-4,5,6,7-tetrahydrothieno[3,2-c]pyridin-2-carboxylic acid The title compound was prepared in the same manner as in Referential Example 2 except that methyl iodide was replaced by benzyl bromide.

$^1$H-NMR (CDCl$_3$) δ: 1.46 (s, 9H), 2.84 (brs, 2H), 3.66 (brs, 2H), 4.23 (brs, 2H), 4.35 (s, 2H), 7.15–7.25 (m, 5H). FDMS (m/z): 374 (M$^+$+1).

Referential Example 4

5-t-butoxycarbonyl-4,5,6,7-tetrahydrothieno[2,3-c]-pyridin-2-carboxylic acid (a) To the solution of 4,5,6,7-tetrahydrothieno[2,3-c]pyridine hydrochloride (5.2 g) in DMF (60 ml) were added di-t-butyl dicarbonate (7.11 g), triethylamine (6.58 g) and a catalytic amount of 4-dimethylaminopyridine, and the mixture was stirred at room temperature for 1 hour. After the addition of ethyl acetate (300 ml) and washed with saturated saline, the mixture was dried over anhydrous magnesium sulfate. The solvent was removed by distillation. The residue was purified by column chromatography on silica gel to give 4.67 g of 5-t-butoxycarbonyl-4,5,6,7-tetrahydrothieno[2,3-c]pyridine from the fraction eluted with n-hexane:ethyl acetate=2:1 (yield, 88%).

$^1$H-NMR (CDCl$_3$) δ:1.48 (s, 9H), 2.70 (brs, 2H), 3.68 (brs, 2H), 4.62 (brs, 2H), 6.79 (d, J=5 Hz, 1H), 7.13 (d, J=5 Hz, 1H). FDMS (m/z): 239 (M$^+$).

(b) The solution of the compound prepared in (a) (358 mg) in THF (5 ml) was cooled to −78° C., n-butyl lithium (2.5M hexane solution, 0.96 ml) was added. The mixture was then stirred for 20 minutes. Carbon dioxide was blown into the reaction mixture for 30 minutes. Water was then added to the resulting mixture. After heating up to room temperature and the additiion of ethyl acetate (500 ml), the mixture was extracted with 5N sodium hydroxide. The aqueous layer was washed with ethyl acetate, and acidified to pH 4 with concentrated hydrochloric acid. After extraction with ethyl acetate, washing with water and drying over anhydrous magnesium sulfate, the solvent was removed by distillation to give 335 mg the title compound (yield, 75%).

$^1$H-NMR (CDCl$_3$) δ: 1.49 (s, 9H), 2.72 (brs, 2H), 3.68 (brs, 2H), 4.66 (brs, 2H), 7.56 (s, 1H). FDMS (m/z): 283 (M$^+$).

Referential Example 5

5-t-butoxycarbonyl-5,6,7,8-tetrahydro-4H-thieno-[3,2-c]azepin-2-carboxylic acid The title compound was prepared in the same manner as in Referential Example 1. EIMS (m/z): 297 (M$^+$).

Referential Example 6

6-t-butoxycarbonyl-5,6,7,8-tetrahydro-4H-thieno-[2,3-d]azepin-2-carboxylic acid The title compound was prepared in the same manner as in Referential Example 1.

Referential Example 7

5-t-butoxycarbonyl-2-formyl-4,5,6,7-tetrahydrothieno[3,2-c]pyridine (a) To the solution of the compound prepared in Referential Example 1 (3.0 g) in THF (20 ml) was added a borane-methyl sulfide complex (1.1 ml), and the mixture was stirred at room temperature for 16 hours. After methanol was added to the reaction mixture, the solvent was removed by distillation. The residue was purified by column chromatography on silica gel to give 1.85 g of 5-t-butoxycarbonyl-2-hydroxymethyl-4,5,6,7-tetrahydrothieno[3,2-c]pyridine from the fraction eluted with ethyl acetate:n-hexane=1:3 (yield, 64.9%).

$^1$H-NMR (CDCl$_3$) δ: 1.48 (s, 9H), 1.82 (t, J=6.1 Hz, 1H), 2.81 (brs, 2H), 3.71 (brs, 2H), 4.43 (brs, 2H), 4.75 (d, J=6.1 Hz, 2H), 6.70 (s, 1H).

(b) The solution of the compound prepared in (a) (1.2 g) in dichloromethane (20 ml) was added pyridinium chlorochromate (1.1 g), and the mixture was stirred at room temperature for 4 hours. After the reaction mixture was filtered through FLORISIL, the filtrate was concentrated and purified by column chromatography on silica gel to give 1.07 g of the title compound from the fraction eluted with ethyl acetate:n-hexane=1:3 (yield, 89.8%).

$^1$H-NMR (CDCl$_3$) δ: 1.50 (s, 9H), 2.92 (brs, 2H), 3.74 (brs, 2H), 4.53 (s, 2H), 7.48 (s, 1H), 9.83 (s, 1H).

Referential Example 8

2-aminoacetyl-5-t-butoxycarbonyl-4,5,6,7-tetrahydrothieno-[3,2-c]pyridine (a) The solution of the compound prepared in Referential Example 7 (255 mg) in THF (10 ml) was cooled to −78° C., and methyl magnesium bromide (1.02M THF solution, 1.0 ml) was added to the solution. The reaction was carried out at −78° C. for 30 minutes and at −40° C. for 10 minutes. After water was added, the mixture was extracted with ethyl acetate, washed with brine and dried over anhydrous magnesium sulfate. After the solvent was removed by distillation, the residue was purified by column chromatography on silica gel with an eluent system of ethyl acetate:n-hexane=1:4 to give 203 mg of 5-t-butoxycarbonyl-2-(1-hydroxy-)ethyl-4,5,6,7-tetrahydrothieno[3,2-c]pyridine (yield, 75%).

$^1$H-NMR (CDCl$_3$) δ: 1.48 (s, 9H), 1.57 (d, J=6.4 Hz, 3H), 1.98 (brs, 1H), 2.80 (brs, 2H), 3.71 (brs, 2H), 4.43 (s, 2H), 5.04 (q, J=6.4 Hz, 1H), 6.67 (s, 1H). FDMS (m/z): 283 (M$^+$).

(b) To the solution of the compound prepared in (a) (847 mg) in dichloromethane (30 ml) was added Molecular Sieves 4A (3 g), followed by pyridinium chlorochromate (966 mg) under ice-cooling. The mixture was stirred for 40 minutes. After the reaction mixture was filtered through FLORISIL, the filtrate was concentrated to give 772 mg of 2-acetyl-5-t-butoxycarbonyl-4,5,6,7-tetrahydrothieno[3,2-c]pyridine (yield, 92%).

$^1$H-NMR (CDCl$_3$) δ: 1.49 (s, 9H), 2.51 (s, 3H), 2.88 (brs, 2H), 3.73 (brs, 2H), 4.50 (s, 2H), 7.39 (s, 1H).

(c) To the solution of the compound prepared in (b) (342 mg) in dichloromethane (6 ml) was added triethylamine (0.42 ml), and the mixture was cooled to −35° C. After trimethylsilyl trifluoromethanesulfonate (0.31 ml) was further added, the resulting mixture was stirred for 25 minutes. After N-bromosuccinimide (227 mg) was then added, the mixture was further stirred at −35° C. for 10 minutes. The mixture was diluted with ether, washed with water, saturated aqueous sodium hydrogen carbonate and brine, and dried over anhydrous magnesium sulfate. After the solvent was removed by distillation, the residue was dissolved in DMF (12 ml). Sodium azide (87 mg) was added to the solution, and the mixture was stirred at room temperature for 1 hour. The reaction mixture was diluted with ethyl acetate, washed with water and brine, and dried over anhydrous magnesium sulfate. After the solvent was removed by distillation, the residue was purified by column chromatography on silica gel with an eluent system of ethyl acetate:n-hexane=1:10 to give 188 mg of 2-azidoacetyl- 5-t-butoxycarbonyl-4,5,6,7-tetrahydrothieno [3,2-c]pyridine (yield, 48% ).

$^1$H-NMR (CDCl$_3$) δ: 1.49 (s, 9H), 2.90 (brs, 2H), 3.73 (brs, 2H), 4.39 (s, 2H), 4.51 (s, 2H), 7.39 (s, 1H). FDMS (m/z): 322 (M$^+$).

(d) To the solution of the compound prepared in (c) (188 mg) in ethanol (10 ml) was added 1N hydrochloric acid (0.7 ml) and 10% palladium-carbon (62 mg), and catalytic hydrogenation was performed at an ordinary temperature under atmospheric pressure for 70 minutes. After the catalyst was removed by filtration through celite, the filtrate was concentrated to give the title compound in the form of a hydrochloride.

$^1$H-NMR (D$_2$O) δ: 1.49 (s, 9H), 2.98 (t, J=5.1 Hz, 2H), 3.76 (brs, 2H), 4.58 (brs, 2H), 4.60 (s, 2H), 7.75 (s, 1H).

Referential Example 9

Di-t-butyl [[4-(aminoacetyl)-o-phenylene]dioxy]diacetate (a) To the suspension of t-butyl bromoacetate (41.4 ml) and potassium carbonate (39 g) in acetone (500 ml) was added 4-chloroacetylcatechol (25 g), and the mixture was stirred at room temperature for 16 hours. The reaction mixture was diluted with ethyl acetate, washed with water and dried over anhydrous magnesium sulfate. After the solvent was removed by distillation, the residue was purified by column chromatography on silica gel with an eluent system of ethyl acetate:n-hexane=1:1 to give 29.1 g of a mixture of di-t-butyl [[4-(chloroacetyl)-o-phenylene]dioxy]diacetate and di-t-butyl [[4-(bromoacetyl)-o-phenylene]dioxy]diacetate.

To the solution of the mixture (15.25 g) in DMF (300 ml) was added sodium azide (2.4 g), and the mixture was stirred at room temperature for 3 hours. The reaction mixture was diluted with ethyl acetate, washed with water and dried over anhydrous magnesium sulfate. After the solvent was removed by distillation, the residue was purified by column chromatography on silica gel with an eluent system of ethyl acetate:n-hexane=1:2 to give 11.2 g of di-t-butyl [[4-(azidoacetyl)-o-phenylene]dioxy]diacetate (yield, 38%).

$^1$H-NMR (CDCl$_3$) δ: 1.48 (s, 9H), 1.49 (s, 9H), 4.49 (s, 2H), 4.66 (s, 2H), 4.68 (s, 2H), 6.82 (d, J=9.2 Hz, 1H), 7.26–7.49 (m, 2H).

EIMS (m/z): 421 (M$^+$).

(b) To the solution of the compound prepared in (a) (10 g) in methanol (200 ml) were added 1N hydrochloric acid (30 ml) and 10% palladium-carbon (500 mg), and catalytic hydrogenation was carried out at room temperature under atmospheric pressure for 4 hours. After the reaction mixture was filtered, the filtrate was concentrated, dissolved in water and lyophilized to give 10.2 g of the title compound in the form of a hydrochloride (yield, 99.6%).

$^1$H-NMR (D$_2$O) δ: 1.47 (s, 18H), 4.63 (s, 2H), 4.85 (s, 2H), 4.87 (s, 2H), 7.07 (d, J=9.2 Hz, 2H), 7.53–7.72 (m, 2H).

Referential Example 10

3,4-(di-t-butoxycarbonylmethyloxy)benzoic acid (a) To the solution of 3,4-dihydroxybenzoic acid (1.13 g) in benzene (50 ml) were added benzyl alcohol (3.8 ml) and p-toluenesulfonic acid (139 mg), and the mixture was heated at reflux in the presence of Molecular Sieves 4A for 2 days. Further amount of benzyl alcohol (1.5 ml) was added. The mixture was then heated at reflux overnight. After cooling by standing, saturated aqueous sodium hydrogen carbonate was added. The mixture was extracted with ethyl acetate, washed with brine and dried over anhydrous magnesium sulfate. After the solvent was removed by distillation, the residue was dissolved in ethyl acetate and extracted with 1N sodium hydroxide. The aqueous layer was acidified with hydrochloric acid and extracted with ethyl acetate. After the organic layer was washed with brine, dried over anhydrous magnesium sulfate, the solvent was removed by distillation. The residue was purified by column chromatography on silica gel with an eluent system of chloroform:methanol=30:1 to give 953 mg of benzyl 3,4-dihydroxybenzoate (yield, 53%).

$^1$H-NMR (DMSO-D$_6$) δ: 5.26 (s, 2H), 6.81 (d, J=8.2 Hz, 1H), 7.36–7.60 (m, 7H), 9.38 (s, 1H), 9.81 (s, 1H). EIMS (m/z): 378 (M$^+$).

(b) To the solution of the compound prepared in (a) (860 mg) in DMF (12 ml) were added under ice-cooling potassium carbonate (1.02 g) and t-butyl bromoacetate (1.14 ml), and the mixture was stirred at room temperature for 2.5 hours. After dilution with ethyl acetate, the mixture was washed with water and saturated saline and dried over anhydrous magnesium sulfate. After the solvent was removed by distillation, the residue was purified by column chromatography on silica gel with an eluent system of ethyl acetate:n-hexane=1:10 to give 1.56 g of benzyl 3,4-(di-t-butoxycarbonylmethyloxy)benzoate (yield, 94%).

$^1$H-NMR (CDCl$_3$) δ: 1.45 (s, 9H), 1.47 (s, 9H), 4.63 (s, 2H), 4.65 (s, 2H), 6.80 (d, J=8.4 Hz, 1H), 7.30–7.45 (m, 5H), 7.52 (d, J=2.3 Hz, 1H), 7.71 (dd, J=2.3, 8.4 Hz, 1H). EIMS (m/z): 472 (M$^+$).

(c) To the solution of the compound prepared in (b) (562 mg) in ethanol (20 ml) was added 10% palladium-carbon (119 mg), and catalytic hydrogenation was carried out at room temperature under atmospheric pressure for 40 minutes. After the catalyst was removed by filtration with celite, the filtrate was concentrated to give 472 mg of the title compound (yield, 100%).

$^1$H-NMR (CDCl$_3$) δ: 1.48 (s, 9H), 1.49 (s, 9H), 4.65 (s, 2H), 4.68 (s, 2H), 6.83 (d, J=8.6 Hz, 1H), 7.55 (d, J=2.0 Hz, 1H), 7.74 (dd, J=2.0, 8.6 Hz, 1H). EIMS (m/z): 382 (M$^+$).

Referential Example 11

Di-t-butyl [[4-[(N-methylamino)acetyl]-o-phenylene]dioxy]-diacetate (a) To the solution of adrenalone hydrochloride (21.8 g) in DMF (200 ml) were added under ice-cooling benzyl chloroformate (20 ml) and pyridine (22 ml), and the mixture was stirred at room temperature for 1 hour. After benzyl chloroformate (10 ml) and pyridine (11 ml) were further added to the mixture, reaction was further continued for 2 days. The reaction mixture was then concentrated under reduced pressure. The residue was dissolved in methanol (200 ml). After 1N sodium hydroxide (300 ml) and 5N sodium hydroxide (20 ml) were added to the solution, the mixture was stirred at room temperature for 1 hour. Methanol was removed by distillation, and the residue was washed with ether. After water was added to the ethereal solution, the mixture was acidified with 5N hydrochloric acid under ice-cooling to pH 2.5. The precipitates were collected by filtration, washed with water and ether and dried to give 17.9 g of N-benzyloxy carbonyladrenalone (yield, 56.8%).

$^1$H-NMR (DMSO-D$_6$) δ: 3.90 and 3.96 (double sets of s, 3H), 4.65 and 4.69 (double sets of s, 2H), 5.02 and 5.10 (double sets of s), 6.81 (brs, 1H), 7.16–7.45 (m, 7H). EIMS (m/z): 315 (M$^+$).

(b) To the solution of the compound prepared in (a) (1.23 g) in DMF (15 ml) were added t-butyl bromoacetate (1.3 ml) and potassium carbonate (2.2 g), and the mixture was stirred at 60° C. for 3 hours. The reaction mixture was diluted with ethyl acetate, washed with water and dried over anhydrous magnesium sulfate. After the solvents were removed by distillation, the residue was purified by column chromatography on silica gel with an eluent system of chloroform:ethyl acetate=7:1 to give 2.08 g of di-t-butyl [[4-[(N-benzyloxycarbonyl-N-methylamino)acetyl]-o-phenylene]dioxy]diacetate (yield, 98%).

$^1$H-NMR (CDCl$_3$) δ: 1.47 (s, 9H), 1.48 (s, 9H), 3.00 and 3.01 (double sets of s, 3H), 4.64 (s, 2H), 4.68 (s, 2H), 5.10 and 5.18 (double sets of s, 2H), 6.78 and 6.81 (double sets of d, J=8.6 Hz, 1H), 7.23–7.41 (m, 5H), 7.44 and 7.48 (double sets of d, J=1.9 Hz, 1H), 7.49 and 7.57 (double sets of dd, J=1.9, 8.6 Hz, 1H).

(c) To the solution of the compound prepared in (b) (4 g) in methanol (50 ml) were added 1N hydrochloric acid (7.5 ml) and 5% palladium-carbon (400 mg), and catalytic hydrogenation was carried out at an ordinary temperature under atmospheric pressure for 3 hours. After the reaction mixture was filtered, the filtrate was concentrated. Water was then added to the residue. The mixture was lyophilized to give 3.3 g of the title compound in the form of a hydrochloride (yield, 100%).

$^1$H-NMR (CD$_3$OD) δ: 1.49 (18H), 2.80 (s, 3H), 4.65 (m, 2H), 4.75 (s, 2H), 4.86 (s, 2H), 7.04 (d, J=8.5 Hz, 1H), 7.58 (d, J=2.1 Hz, 1H), 7.69 (dd, J=2.1, 8.5 Hz, 1H).

Referential Example 12

Diphenylmethyl 3-(4-aminoacetyl)phenylpropionate (a) To the solution of 3-(4-chloroacetyl) phenylpropionate (3 g) in methanol was added diphenyldiazomethane (2.57 g), and the mixture was stirred at room temperature for 16 hours. After the reaction solution was filtered, the filtrate was concentrated and purified by column chromatography on silica gel with an eluent system of ethyl acetate:n-hexane=1:2 to give 4 g of diphenylmethyl 3-(4-chloroacetyl)phenylpropionate (yield, 76.9%).

$^1$H-NMR (CDCl$_3$) δ: 2.77 (t, J=7.7 Hz, 2H), 3.04 (t, J=7.7 Hz, 2H), 4.65 (s, 2H), 6.87 (s, 1H), 7.24–7.35 (m, 12H), 7.81 (d, J=8.2 Hz, 2H).

(b) To the solution of the compound prepared in (a) (3.55 g) in DMF (10 ml) was added sodium azide (1.17 g), and the mixture was stirred at room temperature for 3 hours. The reaction mixture was diluted with ethyl acetate, washed with water and dried over anhydrous magnesium sulfate. After the solvents were removed by distillation, the residue was purified by column chromatography on silica gel with an eluent system of ethyl acetate:n-hexane =1:3 to give 3.3 g of diphenylmethyl 3-(4-azidoacetyl)phenylpropionate (yield, 83.9%).

$^1$H-NMR (CDCl$_3$) δ: 2.28 (t, J=7.4 Hz, 2H), 3.05 (t, J=7.4 Hz, H), 4.51 (s, 2H), 6.87 (s, 1H), 7.25–7.31 (m, 12H), 7.77 (d, J=8.5 Hz, 2H).

(c) To the solution of the compound prepared in (b) (1 g) in methanol (20 ml) were added 1N hydrochloric acid and 10% palladium-carbon (50 mg), and catalytic hydrogenation was carried out at room temperature under atmospheric pressure for 3 hours. After the reaction mixture was filtered, the filtrate was concentrated, dissolved in water and then lyophilized to give 1 g of the title compound in the form of a hydrochloride (yield, 7.4%).

$^1$H-NMR (CD$_3$OD) δ: 2.84 (t, J=7.4 Hz, 2H), 3.06 (t, J=7.4 Hz, 2H), 4.53 (s, 2H), 6.80 (s, 1H), 7.24–7.31 (m, 10H), 7.38 (d, J=8.5 Hz, 2H), 7.88 (d, J=8.5 Hz, 2H).

Referential Example 13

2-(2-amino-1-hydroxy)ethyl-5-(t-butoxycarbonylmethyl)oxypyridine (a) The solution of 5-hydroxy-2-hydroxymethylpyridine (5.0 g) in DMF (10 ml) was titrated under ice-cooling in the suspension of sodium hydride (60% purity, 1.6 g) in DMF (10 ml). After 10 minutes, the mixture was heated to room temperature and stirred for 15 minutes. After t-butyl bromoacetate (6 ml) was added to the mixture under ice-cooling, the resulting mixture was stirred under ice-cooling for 10 minutes and at room temperature for 45 minutes. The reaction mixture was diluted with ethyl acetate, washed with water and brine and dried over anhydrous magnesium sulfate. After the solvents were removed by distillation, the residue was purified by column chromatography on silica gel with an eluent system of chloroform→chloroform: methanol=50:1 to give 8.16 g of 5-(t-butoxycarbonylmethyl)oxy-2-hydroxymethylpyridine (yield, 85%).

$^1$H-NMR (CDCl$_3$) δ: 1.50 (s, 9H), 3.35–3.45 (brs, 1H), 4.56 (s, 2H), 4.70 (s, 2H), 7.19 (d, J=8.5 Hz, 1H), 7.23 (dd, J=2.8, 8.5 Hz, 1H), 8.25 (d, J=2.8 Hz, 1H). EIMS (m/z): 239 (M$^+$).

(b) To the solution of the compound prepared in (a) (10.5 g) in dichloromethane (250 ml) was added manganese dioxide (19 g) under ice-cooling. The mixture was stirred at room temperature for 5 hours, during which 10 g of manganese dioxide was added every 1 to 1.5 hours. After the reaction mixture was filtered through celite, the filtrate was concentrated to give 8.95 g of 5-(t-butoxycarbonylmethyl)oxy-2-formylpyridine (yield, 86%).

$^1$H-NMR (CDCl$_3$) δ: 1.50 (s, 9H), 4.66 (s, 2H), 4.70 (s, 2H), 7.28 (dd, J=2.7, 8.6 Hz, 1H), 7.97 (d, J=8.6 Hz, 1H), 8.45 (d, J =2.7 Hz, 1H), 10.0 (s, 1H). EIMS (m/z): 237 (M$^+$).

(c) The solution of the compound prepared in (b) (6.2 g) in THF (200 ml) was cooled to −40° C., and methyl magnesium bromide (1.02M THF solution, 27 ml) was titrated. After 30 minutes, water was added to the mixture. The mixture was extracted with ethyl acetate, washed with brine and dried over anhydrous magnesium sulfate. After the solvents were removed by distillation, the residue was purified by column chromatography on silica gel with an eluent system of ethyl acetate:n-hexane =1:1 to give 5.2 g of 5-(t-butoxycarbonylmethyl)oxy-2-(1-hydroxy)ethylpyridine (yield, 79%).

$^1$H-NMR (CDCl$_3$) δ: 1.48 (d, J=6.5 Hz, 3H), 1.50 (s, 9H), 3.91 (d, J=4.6 Hz, 1H), 4.56 (s, 2H), 4.86 (dq, J=4.6, 6.5 Hz, 1H), 7.22–7.23 (m, 2H), 8.22 (t, J=1.5 Hz, 1H). EIMS (m/z): 253 (M$^+$).

(d) The compound prepared in (c) (3.31 g) was treated in the same manner as in (b) to give 3.33 g of 2-acetyl-5-(t-butoxycarbonylmethyl)oxypiridine (yield, 100%).

$^1$H-NMR (CDCl$_3$) δ: 1.50 (s, 9H), 2.68 (s, 3H), 4.63 (s, 2H), 7.23 (dd, J=3.1, 8.6 Hz, 1H), 8.04 (d, J=8.6 Hz, 1H), 8.34 (d, J =3.1 Hz, 1H). EIMS (m/z): 251 (M$^+$).

(e) To the solution of the compound prepared in (d) (468 mg) in dichloroethane (10 ml) was added triethylamine (0.65 ml), and trimethylsilyl trifluoromethanesulfonate (0.4 ml) was titrated under ice-cooling. The mixture was stirred for 30 minutes. The solvent was then evaporated under reduced pressure. The residue was extracted with ether.

After ether was evaporated, the residue was dissolved in THF (10 ml), N-bromosuccinimide (353 mg) was added under ice-cooling. After the mixture was stirred for 30 minutes, the mixture was diluted with ether, washed with water, saturated sodium hydrogen carbonate and brine, and dried over anhydrous magnesium sulfate. After the solvents were removed by distillation, hexane was added to the residue thus obtained. Crystals were collected by filtration to give 451 mg of 2-bromoacetyl-5-(t-butoxycarbonylmethyl)oxypyridine (yield, 73%).

$^1$H-NMR (CDCl$_3$) δ: 1.50 (s, 9H), 4.56 (s, 2H), 4.64 (s, 2H), 4.81 (s, 2H), 7.25 (dd, J=2.8, 8.6 Hz, 1H), 8.10 (d, J=8.6 Hz, 1H), 8.34 (d, J=2.8 Hz, 1H). EIMS (m/z): 329, 331 (M$^+$).

(f) To the solution of the compound prepared in (e) (427 mg) in DMF (10 ml) was added sodium azide (95 mg), and the mixture was stirred for 1 hour. The reaction mixture was diluted with ethyl acetate, washed with water and brine and dried over anhydrous magnesium sulfate. After the solvents was removed by distillatio, the residue was purified by column chromatography on silica gel with an eluent system of toluene:ethyl acetate =30:1 to give 297 mg of 2-azidoacetyl-5-(t-butoxycarbonylmethyl)oxypyridine (yield, 79% ).

$^1$H-NMR (CDCl$_3$) δ: 1.50 (s, 9H), 4.64 (s, 2H), 4.81 (s, 2H), 7.26 (dd, J=2.8, 8.6 Hz, 1H), 8.08 (d, J=8.6 Hz, 1H), 8.31 (d, J =2.8 Hz, 1H). SIMS (m/z): 293 (M$^+$+1).

(g) To the solution of the compound prepared in (f) in ethanol (4 ml) were added 1N hydrochloric acid (0.52 ml) and 10% palladium-carbon (22 mg), and catalytic hydrogenation was carried out at room temperature under atmospheric pressure for 1 hour. After the reaction mixture was filtered through celite, the filtrate was concentrated to give 72 mg of the title compound in the form of a hydrochloride (yield, 100%).

$^1$H-NMR (D$_2$O) δ: 1.52 (s, 9H), 3.31 (dd, J=9.0, 13.1 Hz, 1H), 3.55 (dd, J=3.3, 13.1 Hz, 1H), 4.94 (s, 2H), 5.40 (dd, J=3.3, 9.0 Hz, 1H), 7.97 (d, J=9.0 Hz, 1H), 8.11 (dd, J=2.8, 9.0 Hz, 1H), 8.50 (d, J=2.8 Hz, 1H). SIMS (m/z): 269 (M$^+$+1).

Referential Example 14

Ethyl 4-(2-aminoethyl)phenoxyacetate (a) To the solution of tyramine (5 g) in DMF (50 ml) were added triethylamine (5 ml) and di-t-butyl dicarbonate (8.4 ml), and the mixture was stirred at a temperature of ice-cooling to room temperature. After the reaction mixture was concentrated under reduced pressure, the residue was diluted with ethyl acetate, washed with water and dried over anhydrous magnesium sulfate. The solvents were then removed by distillation. The residue was purified by column chromatography on silica gel with an eluent system of chloroform:emthanol=30:1 to give 8.5 g of N-t-butoxycarbonyl-tyramine (yield, 99%).

$^1$H-NMR (CDCl$_3$) δ: 1.44 (s, 9H), 2.70 (brs, 2H), 3.32 (brs, 2H), 6.79 (d, J=8.5 Hz, 2H), 7.00 (d, J=8.5 Hz, 2H). FDMS (m/z): 237 (M$^+$).

(b) To the solution of the compound prepared in (a) (2 g) in DMF (20 ml) were added ethyl bromoacetate (0.98 ml) and potassium carbonate (1.4 g), and the mixture was stirred at room temperature overnight. The reaction mixture was diluted with ethyl acetate, washed with water and dried over anhydrous magnesium sulfate. After the solvents were evaporated, the residue was purified by column chromatography on silica gel with an eluent system of chloroform:emthanol=50:1 to give 2.5 g of ethyl [4-(2-t-butoxycarbonylamino)ethyl]phenoxyacetate (yield, 90%).

$^1$H-NMR (CDCl$_3$) δ: 1.30 (t, J=6.9 Hz, 3H), 1.43 (s, 9H), 2.73 (t, J=6.9 Hz, 2H), 3.33 (t, J=6.9 Hz, 2H), 4.28 (q, J=6.9 Hz, 2H), 6.85 (d, J=8.6 Hz, 2H), 7.11 (d, J=8.6 Hz, 2H). EIMS (m/z): 323 (M$^+$).

(c) To the solution of the compound prepared in (b) (2 g) in anisole (3.3 ml) was added trifluoroacetic acid (3 ml), and the mixture was stirred at room temperature for 3 hours. The reaction mixture was concentrated under reduced pressure. The residue was washed with n-hexane, dissolved in water and lyophilized to give the title compound in the form of a trifluoroacetate.

$^1$H-NMR (CDCl$_3$) δ: 1.30 (t, J=7.2 Hz, 3H), 2.69 (t, J=6.9 Hz, 2H), 2.93 (t, J=6.9 Hz, 2H), 4.28 (q, J=7.2 Hz, 2H), 4.60 (s, 2H), 6.85 (d, J=8.6 Hz, 2H), 7.11 (d, J=8.6 Hz, 2H).

Referential Example 15 t-butyl 4-(aminoacetyl)phenoxyacetate (a) To the solution of p-acetylphenol (10 g) in DMF (50 ml) were added potassium carbonate (12.2 g) and t-butyl bromoacetate (16.2 ml), and the mixture was stirred at room temperature for 2 hours. After the reaction mixture was concentrated under reduced pressure, the residue was diluted with ethyl acetate, washed with water and dried over anhydrous magnesium sulfate. After the solvents were removed by distillation, crystals thus obtained were washed with n-hexane to give 17.7 g of t-butyl 4-acetylphenoxyacetate (yield, 96%).

$^1$H-NMR (CDCl$_3$) δ: 1.49 (s, 9H), 2.56 (s, 3H), 4.58 (s, 2H), 6.93 (d, J=9.2 Hz, 2H), 7.94 (d, J=9.2 Hz, 2H). EIMS (m/z): 250 (M$^+$).

(b) To the solution of the compound prepared in (a) (500 mg) in 1,2-dichloroethane (5 ml) were added triethylamine (0.68 ml) followed by trimethylsilyl trifluoromethanesulfonate (0.44 ml), and the mixture was stirred at room temperature for 1 hour. After trimethylsilyl trifluoromethanesulfonate (0.1 ml) was added, the mixture was further stirred for 30 minutes. The reaction mixture was concentrated, and the residue was extracted with ether by decantation. After the ether was evaporated, the residue thus obtained was dissolved in THF (5 ml), N-bromosuccinimide (374 mg) was added under ice-cooling. The mixture was then stirred at room temperature for 1.5 hours. The reaction mixture was diluted with ether, washed with water, saturated aqueous sodium hydrogen carbonate and water in this sequence, and dried over anhydrous magnesium sulfate. The solvents were evaporated to give 650 mg of t-butyl 4-bromoacetylphenoxyacetate (yield, 95%).

$^1$H-NMR (CDCl$_3$) δ: 1.49 (s, 9H), 4.40 (s, 2H), 4.60 (s, 2H), 6.95 (d, J=9.0 Hz, 2H), 7.97 (d, J=9.0 Hz, 2H). EIMS (m/z): 330 (M$^+$).

(c) To the solution of the compound prepared in (b) (660 mg) in DMF (6 ml) was added sodium azide (156 mg), and the mixture was stirred at room temperature for 1 hour. The reaction mixture was diluted with ethyl acetate, washed with water and dried over anhydrous magnesium sulfate. After the solvents were evaporated, the residue was purified by column chromatography on silica gel with an eluent system of n-hexane:ethyl acetate=5:1 to give 37 mg of t-butyl 4-azidoacetylphenoxyacetate (yield, 92%).

$^1$H-NMR (CDCl$_3$) δ: 1.49 (s, 9H), 4.51 (s, 2H), 4.59 (s, 2H), 6.95 (d, J=8.9 Hz, 2H), 7.89 (d, J=8.9 Hz, 2H).

(d) To the solution of the compound prepared in (c) (537 mg) in ethanol (8 ml) were added 1N hydrochloric acid (2.2 ml) and 10% palladium-carbon (50 mg), and catalytic hydrogenation was performed at room temperature under atmospheric pressure for 1.5 hours. The reaction mixture was filtered through celite. After the filtrate was concentrated, the residue was dissolved in water, washed with ether and lyophilized to give the title compound in the form of a hydrochloride.

$^1$H-NMR (CD$_3$OD) δ: 1.48 (s, 9H), 4.52 (s, 2H), 4.72 (s, 2H), 7.05 (d, J=8.9 Hz, 2H), 8.01 (d, J=8.9 Hz, 2H). FDMS (m/z): 265 (M$^+$).

Referential Example 16

Di-t-butyl [[5-(aminoacetyl)-m-phenylene]dioxy]diacetate

The title compound was prepared from 3',5'-dihydroxyacetophenone according to the same manner as in Referential Example 15.

$^1$H-NMR (CD$_3$OD) δ: 1.51 (s, 18H), 4.56 (s, 2H), 4.59 (s, 2H), 4.68 (s, 2H), 6.62 (s, 1H), 6.84 (s, 2H). EIMS (m/z): 395 (M$^+$).

Referential Example 17 t-butyl 3-(aminoacetyl)phenoxyacetate

The title compound was prepared from m-acetylphenol according to the same manner as in Referential Example 15.

$^1$H-NMR (CD$_3$OD) δ: 1.49 (s, 9H), 4.57 (s, 2H), 4.68 (s, 2H), 7.27 (m, 1H), 7.48–7.54 (m, 2H), 7.65 (m, 1H).

Referential Example 17 t-Butyl 3-(aminoacetyl)phenoxyacetate

The title compound was prepared from m-acetylphenol according to the same manner as in Referential Example 15.

$^1$H-NMR (CD$_3$OD) δ: 1.49 (s, 9H), 4.57 (s, 2H), 4.68 (s, 2H), 7.27 (m, 1H), 7.48–7.54 (m, 2H), 7.65 (m, 1H).

Referential Example 18

Di-t-butyl [[4-(aminoacetyl)-m-phenylene]dioxy]diacetate

The title compound was prepared from 2',4'-dihydroxyacetophenone according to the same manner as in Referential Example 15.

$^1$H-NMR (CD$_3$OD) δ: 1.57 (s, 9H), 1.59 (s, 9H), 4.63 (s, 2H), 4.78 (s, 2H), 4.88 (s, 2H), 6.69 (s, 1H), 6.75 (d, J=8.8 Hz, 1H), 8.08 (d, J=8.8 Hz, 1H).

Referential Example 19 t-Butyl [4-(aminoacetyl)-2-methoxy]phenoxyacetate (a) To the solution of 4-chloroacetylcatechol (25 g) in DMF (200 ml) was added sodium azide (10.5 g), and the mixture was stirred at room temperature for 1 hour. The reaction mixture was diluted with ethyl acetate, washed with water and dried over anhydrous magnesium sulfate. After the solvent was evaporated, the solids thus obtained was washed with a solution of n-hexane:ether=5:1 to give 23.2 g of 4-azidoacetylcatechol (yield, 90%).

$^1$H-NMR (CD$_3$OD) δ: 4.59 (s, 2H), 6.84 (d, J=8.3 Hz, 1H), 7.39 (m, 2H). EIMS (m/z): 193 (M$^+$).

(b) To the solution of the compound prepared in (a) (1 g) in acetone (10 ml) were added t-butyl bromoacetate (0.76 ml) and potassium carbonate (716 mg), and the mixture was stirred at room temperature for 1.5 hours. The reaction mixture was diluted with ethyl acetate, washed with water and dried over anhydrous magnesium sulfate. After the solvents were evaporated, the residue was purified by column chromatography on silica gel with an eluent system of chloroform:methanol=50:1 to give 318 mg of t-butyl 4-azidoacetyl-3-hydroxyphenoxyacetate (yield, 20%).

$^1$H-NMR (CDCl$_3$) δ: 1.50 (s, 9H), 4.49 (s, 2H), 4.61 (s, 2H), 6.89 (d, J=8.2 Hz, 1H), 7.45 (dd, J=2.1, 8.2 Hz, 1H), 7.49 (d, J=2.1 Hz, 1H).

(c) To the solution of the compound prepared in (b) (500 mg) in acetone (5 ml) was added potassium carbonate (340 mg) and methyl iodide (0.5 ml), and the mixture was stirred at room temperature for 1 hour. After additional amount of methyl iodide (0.5 ml) was added, the mixture was further stirred at 50° C. for 1 hour. The reaction mixture was diluted with ethyl acetate, washed with water and dried over anhydrous magnesium sulfate. After the solvents were evaporated, the residue was purified by column chromatography on silica gel with an eluent system of chloroform:ethyl acetate=50:1 to give 400 mg of t-butyl 4-azidoacetyl-3-methoxyphenoxyacetate (yield, 76%).

$^1$H-NMR (CDCl$_3$) δ: 1.47 (s, 9H), 3.95 (s, 3H), 4.51 (s, 2H), 4.67 (s, 2H), 6.77 (d, J=8.5 Hz, 1H), 7.42 (1H, dd, J=2.0, 8.5 Hz), 7.54(1H, d, J=2.0 Hz). EIMS (m/z): 321 (M$^+$).

(d) The title compound in the form of a hydrochloride was obtained according to the method described in Referential Example 15 (d).

$^1$H-NMR (CD$_3$OD) δ: 1.48 (s, 9H), 3.93 (s, 3H), 4.54 (s, 2H), 4.74 (s, 2H), 6.97 (d, J=8.6 Hz, 1H), 7.60 (d, J=1.0 Hz, 1H), 7.64 (dd, J=1.9, 8.6 Hz, 1H). EIMS (m/z): 295 (M$^+$).

Referential Example 20

Diethyl [[4-(2-aminoethyl)-o-phenylene]dioxy]diacetate

The title compound was prepared as the trifluoroacetate according to the same manner as in Referential Example 14.

$^1$H-NMR (CDCl$_3$) δ: 1.29 (m, 6H), 2.90 (m, 2H), 3.21 (m, 2H), 4.25 (m, 4H), 4.63 (s, 2H), 4.64 (s, 2H), 6.79 (m, 3H), 7.95 (brs, 2H).

Referential Example 21

Diethyl [[4-(aminoacetyl)-o-phenylene]dioxy]diacetate (a) The solution of the compound prepared in Referential Example 19 (a) (13 g) in acetone (100 ml) was added to the solution of ethyl bromoacetate (15.7 ml) and potassium carbonate (19.5 g) in acetone (100 ml), and the mixture was stirred at room temperature for 12 hours. After insolubles were removed by filtration, the solvents were evaporated. Crystals obtained were collected by filtration, washed with ether and dried to give 11.1 g of diethyl [[4-(azidoacetyl)-o,phenylene]dioxy]diacetate ¹H-NMR (CDCl₃) δ: 1.29 (t, J=7 Hz, 3H), 1.31 (t, J=7 Hz, 3H), 4.27 (d, J=7 Hz, 2H), 4.28 (q, J=7 Hz, 2H), 4.49 (s, 2H), 4.77 (s, 2H), 4.80 (s, 2H), 6.86 (d, J=8 Hz, 1H), 7.49 (d, J =8 Hz, 1H), 7.51 (s, 1H).

(b) To the solution of the compound prepared in (a) (1 g) in ethanol (45 ml) were added 1N hydrochloric acid (4.9 ml) and 5% palladium-carbon (90 mg), and catalytic hydrogenation was performed at room temperature under atmospheric pressure for 1 hour. After the catalyst was removed by filtration through celite, the solvent was evaporated. Crystals deposited were collected by filtration, washed with ether and dried to give the title compound as the hydrochloride.

¹H-NMR (CDCl₃+CD₃OD) δ: 1.31 (t, J=7 Hz, 6H), 4.27 (q, J=7 Hz, 2H), 4.28 (q, J=7 Hz, 2H), 4.47 (brs, 2H), 4.79 (s, 2H), 4.82 (s, 2H), 6.90 (d, J=8 Hz, 1H), 7.55 (s, 1H), 7.63 (d, J =8 Hz, 1H).

Example 18

[[4-[[[(4,5,6,7-tetrahydrothieno [3,2-c]pyridin-2-yl]carbonyl]amino]acetyl]-o-phenylene]dioxy]diacetic acid trifluoroacetate (a) To the solution of the compound prepared in Referential Example 1 (3.0 g) in DMF (20 ml) were added benzotriazole-1-yloxytris(dimethylamino)phosphonium hexafluorophosphate (7.0 g) and N-methylmorpholine (2.3 ml), and the mixture was stirred at room temperature for 1 hour. After the compound prepared in Referential Example 9 (4.6 g) was added, the mixture was stirred at room temperature for 1 hour. The solvent was evaporated under reduced pressure. The residue was then taken into ethyl acetate. The mixture was washed with water and dried over anhydrous magnesium sulfate. After the solvent was evaporated, the residue was purified by column chromatography on silica gel to give 3.56 g of di-t-butyl [[4-[[[(5-t-butyloxycarbonyl-4,5,6,7-tetrahydrothieno[3,2-c]pyridin-2-yl)carbonyl]amino]acetyl]-o-phenylene]dioxy]diacetate from the fraction eluted with ethyl acetate:n-hexane=1:1 (yield, 50.9%).

¹H-NMR (CDCl₃) δ: 1.48–1.58(27H), 2.87 (brs, 2H), 3.73 (brs, 2H), 4.49 (s, 2H), 4.67 (s, 2H), 4.70 (s, 2H), (s, 4.84 (d, J=4.1 Hz, 1H), 6.85 (d, 8.7 Hz, 1H), 7.08 (brs, 7.33 (s, 1H), 7.50 (d, J=1.9 Hz, 1H), 7.63 (dd, J=1.9, 8.3 Hz, 1H).

(b) To the aforementioned compound (3.56 g) were added anisole (5 ml) and trifluoroacetic acid (20 ml), and the mixture was stirred at room temperature for 3 hours. After isopropyl ether was added to the reaction mixture, crystals deposited were collected by filtration to give 2.95 g of the title compound (97.3%).

¹H-NMR (DMSO-d₆) δ: 3.08 (m, 2H), 3.37–3.61 (m, 2H), 4.24 (s, 2H), 4.70 (s, 2H), 4.79 (s, 2H), 4.85 (s, 2H), 7.02 (d, J=8.8 Hz, 1H), 7.42 (d, J=1.8 Hz, 1H), 7.60 (s, 1H), 7.70 (dd J=1.8, 8.8 Hz, 1H), 8.82 (brs, 1H), 9.09 (brs, 1H).

The compounds of Example 19–38 were prepared in the same manner as in Example 18.

Example 19

[[4-[[[(4,5,6,7-tetrahydrothieno[3,2-c]pyridin-2-yl)-carbonyl]-N-methylamino]acetyl]-o-phenylene]-dioxy]diacetic acid trifluoroacetate The title compound was prepared from the compounds of Referential Examples 1 and 11.
(a) Di-t-butyl [[4-[[[(5-t-butyloxycarbonyl-4,5,6,7-tetrahydrothieno[3,2-c]pyridin-2-yl)carbonyl]-N-methylamino]acetyl]-o-phenylene]dioxy]diacetate ¹H-NMR (CDCl₃) δ: 1.48 (27H), 2.83 (brs, 2H), 3.31 (brs, 3H), 3.71 (brs, 2H), 4.46 (brs, 2H), 4.68 (s, 2H), 4.82 (brs, 2H), 4.90 (s, 2H), 6.82–7.50 (m, 4H).
(b) Title compound ¹H-NMR (DMSO-d₆) δ: 3.07 (brs, 2H), 3.33 (brs, 3H), 3.45 (brs, (s, 2H), 4.22 (brs, 2H), 4.78 (s, 2H), 4.85 (brs, 2H), 4.95 (brs, 2H), 7.01–7.66 (m, 4H).

Example 20

3-[4-[[(4,5,6,7-tetrahydrothieno[3,2-c]pyridin-2-yl)-carbonyl]aminoacetyl]phenyl]propionic acid trifluoroacetate The title compound was prepared from the compounds of Referential Examples 1 and 12.
(a) Diphenylmethyl 3-[4-[[[(5-t-butyloxycarbonyl-4,5,6,7-tetrahydrothieno [3,2-c]pyridin-2-yl) carbonyl]aminoacetyl] phenyl]propionate ¹H-NMR (CDCl₃) δ: 1.50 (s, 9H), 2.79 (t, J=7.5 Hz, 2H), 2.88 (s, 2H), 3.06 (t, J=7.5 Hz, 2H), 3.74 (brs, 2H), 4.51 (brs, 2H), 4.87 (d, J=4.2 Hz, 2H), 6.87 (s, 1H), 7.03 (brs, 1H), 7.28–7.34 (m, 10H), 7.87 (d, J=8.3 Hz, 1H). FDMS (m/z): 638 (M⁺).
(b) Title compound ¹H-NMR (CD₃OD) δ: 2.65 (t, J=7.4 Hz, 2H), 3.00 (t,. J=7.4 Hz, 2H), 3.20 (t, J=6.2 Hz, 2H), 3.57 (t, J=6.2 Hz, 2H), 4.32 (s, 2H), 4.87 (s, 2H), 7.41 (d, J=8.5 Hz, 2H), 7.97 (d, J=8.5 Hz, 2H). FDMS (m/z): 372 (M⁺).

Example 21

2-[1-hydroxy-2-[(4,5,6,7-tetrahydrothieno[3,2-c]-pyridin-2-yl) carbonylamino]ethyl]pyridin-5-yloxyacetic acid trifluoroacetate The title compound was prepared from the compounds of Referential Examples 1 and 13.
(a) t-Butyl 2-[2-[(5-t-butoxycarbonyl-4,5,6,7-tetrahydrothieno[3,2-c]pyridin-2-yl)-carbonylamino]-1-hydroxy-ethyl]pyridin-5-yloxyacetate ¹H-NMR (CDCl₃ ) δ: 1.48 (s, 9H), 1.49 (s, 9H), 2.84 (brs, 2H), 3.57 (m, 1H), 3.60 (ddd, J=2.8, 6.4, 13.8 Hz, 1H), 3.71 (brs, 2H), 4.46 (s, 2H), 4.56 (s, 2H), 4.60–4.80 (brs, 1H), 4.90 (dd, J=2.8, 6.4 Hz, 1H), 6.51 (brt, 1H), 7.18 (s, 1H), 7.23 (dd, J =2.8, 8.3 Hz, 1H), 7.37 (d, J=8.6 Hz, 1H), 8.24 (d, J=2.8 Hz, 1H). EIMS (m/z ): 533 (M⁺).
(b) Title compound ¹H-NMR (D₂O) δ: 3.20 (t, J=6.2 Hz, 2H), 3.59 (t, J=6.2 Hz, 2H), 3.82 (ABbq, J=5.1, 1.14, 4 Hz, 1H), 4.32 (s, 2H), 4.97 (s, 2H), 5.34 (t, J=5.1 Hz, 1H), 7.42 (s, 1H), 8.01 (d, J=9.0 Hz, 1H), 8.16 (dd, J=2.8, 9.0 Hz, 1H), 8.44 (d, J=2.8 Hz, 1H). SIMS (m/z): 378 (M⁺+1).

Example 22

4-[[(4,5,6,7-tetrahydrothieno[3,2-c]pyridin-2-yl)-carbonyl]aminoacetyl]phenoxyacetic acid trifluoroacetate The title compound was prepared from the compounds of Referential Examples 1 and 15.

(a) t-butyl 4-[[(5-t-butoxycarbonyl-4,5,6,7-tetrahydrothieno[3,2-c]pyridin-2-yl)carbonyl]aminoacetyl]phenoxyacetate ¹H-NMR (CDCl₃) δ: 1.49 (s, 9H), 2.87 (brs, 2H), 3.73 (brs, 2H), 4.50 (s, 2H), 4.61 (s, 2H), 4.85 (d, J=3.9 Hz, 2H), 6.98 (d, J=8.2 Hz, 2H), 7.05 (brs, 1H), 7.33 (s, 1H), 8.00 (d, J=8.2 Hz, 2H). EIMS (m/z): 530 (M⁺).

(b) Title compound

¹H-NMR (CD₃OD) δ: 3.21 (t, J=6.2 Hz, 2H), 3.57 (t, J=6.2 Hz, 2H), 4.32 (s, 2H), 4.78 (s, 2H), 4.81 (s, 2H), 7.06 (d, J=9.0 Hz, 2H), 7.5 (s, 1H), 8.03 (d, J=9.0 Hz, 1H). FDMS (m/z): 375 (M⁺+1).

Example 23

[[5-[[[(4,5,6,7-tetrahydrothieno[3,2-c]pyridin-2-yl)carbonyl]amino]acetyl]-m-phenylene]dioxy]diacetic acid trifluoroacetate The title compound was prepared from the compounds of Referential Examples 1 and 16.

(a) Di-t-butyl [[5-[[[(5-t-butoxycarbonyl-4,5,6,7-tetrahydrothieno[3,2-c]pyridin-2-yl)carbonyl]amino]acetyl]-m-phenylene]dioxy]diacetate ¹H-NMR (CDCl₃) δ: 1.50 (s, 9H), 1.51 (18H), 2.87 (brs, 2H), 3.74 (brs, 2H), 4.50 (brs, 2H), 4.55 (s, 4H), 4.84 (d, J=4.4 Hz, 2H), 6.76 (t, J=2.2 Hz, 1H), 6.94 (brs, 1H), 7.14 (d, J=2.2 Hz, 1H), 7.33 (s, 1H).

(b) Title compound

¹H-NMR (CD₃OD) δ: 3.20 (t, J=6.4 Hz, 2H), 3.57 (t, J=6.4 Hz, 2H), 4.32 (s, 2H), 4.74 (s, 4H), 4.80 (s, 2H), 6.84 (t, J=2.2 Hz, 1H), 7.2 (d, J=2.2 Hz, 2H), 7.54 (s, 1H). FDMS (m/z): 449 (M⁺+1).

Example 24

3-[[4,5,6,7-tetrahydrothieno[3.2-c]pyridin-2-yl)carbonyl]aminoacetyl]phenoxyacetic acid trifluoroacetate The title compound was prepared from the compounds of Referential Examples 1 and 17.

(a) t-Butyl 3-[[(5-t-butoxycarbonyl-4,5,6,7-tetrahydrothieno[3,2-c]pyridin-2-yl)carbonyl]aminoacetyl]phenoxyacetate ¹H-NMR (CDCl₃) δ: 1.50 (s, 9H), 1.51 (s, 9H), 2.88 (s, 2H), 3.74 (s, 2H), 4.50 (s, 2H), 4.59 (s, 2H), 4.89 (d, J=4.4 Hz, 2H), 6.99 (brs, 1H), 7.20 (dd, J=2.6, 8.1 Hz, 1H), 7.44 (t, J=8.1 Hz, 1H), 7.50 (m, 1H), 7.63 (d, J=7.5 Hz, 1H).

(b) Title compound

¹H-NMR (CD₃OD) δ: 3.22 (brs, 2H), 3.58 (brs, 2H), 4.32 (brs, 2H), 4.75 (s, 2H), 4.84 (s, 2H), 7.25 (d, J=8.0 Hz, 1H), 7.48 (t, J=8.0 Hz, 1H), 7.56 (m, 2H), 7.68 (d, J=7.4 Hz, 1H). FDMS (m/z ): 375 (M⁺+1).

Example 25

[[4-[[[(4,5,6,7-tetrahydrothieno[3.2-c]pyridin-2-yl)carbonyl]amino]acetyl]-m-phenylene]dioxy]diacetic acid trifluoroacetate The title compound was prepared from the compounds of Referential Examples 1 and 18.

(a) Di-t-butyl [[4-[[[(5-t-butoxycarbonyl-4,5,6,7-tetrahydrothieno[3,2-c]pyridin-2-yl)carbonyl]amino]acetyl]-m-phenylene]dioxy]diacetate ¹H-NMR (CDCl₃) δ: 1.49 (s, 9H), 1.50 (s, 9H), 2.85 (brs, 2H), 3.72 (brs, 2H), 4.48 (brs, 2H), 4.55 (s, 2H), 4.67 (s, 2H), 4.87 (d, J=4.6 Hz, 2H), 6.40 (d, J=2.1 Hz, 1H), 6.52 (dd, J=2.1, 8.9 Hz, 1H), 7.30 (s, 1H), 7.99 (d, J=8.9 Hz, 1H).

(b) Title compound

¹H-NMR (CD₃OD) δ: 3.19 (brs, 2H), 3.57 (brs, 2H), 4.31 (brs, 2H), 4.76 (s, 2H), 4.83 (s, 2H), 6.64 (m, 2H), 7.52 (s, 1H), 7.88 (d, J=8.6 Hz, 1H). FDMS (m/z): 449 (M⁺+1).

Example 26

4-[[4,5,6,7-tetrahydrothieno[3.2-c]pyridin-2-yl)carbonyl]aminoacetyl]-2-methoxyphenoxyacetic acid trifluoroacetate The title compound was prepared from the compounds of Referential Examples 1 and 19.

(a) t-Butyl [[(5-t-butoxycarbonyl-4,5,6,7-tetrahydrothieno[3,2-c]pyridin-2-yl)carbonyl]aminoacetyl]-3-methoxyphenoxyacetate ¹H-NMR (CDCl₃) δ: 1.48 (s, 9H), 1.50 (s, 9H), 2.89 (brs, 2H), 3.74 (brs, 2H), 3.97 (s, 3H), 4.50 (brs, 2H), 4.68 (s, 2H), 4.86 (d, J=4.2 Hz, 2H), 6.81 (d, J=8.3 Hz, 1H), 7.04 (brs, 1H), 7.34 (s, 1H), 7.56 (d, J=2.0 Hz, 1H), 7.61 (dd, J=2.0, 8.3 Hz, 1H).

(b) Title compound

¹H-NMR (CD₃OD) δ: 3.20 (t, J=5.9 Hz, 2H), 3.57 (t, J=5.9 Hz, 2H), 3.92 (s, 3H), 4.31 (brs, 2H), 4.80 (s, 2H), 4.82 (s, 2H), 6.99 (d, J=8.5 Hz, 1H), 7.54 (s, 1H), 7.60 (d, J=1.8 Hz, 1H), 7.68 (dd, J=1.8, 8.5 Hz, 1H). FDMS (m/z): 405 (M⁺+1).

Example 27

[[4-[[[(3-methyl-4,5,6,7-tetrahydrothieno[3.2-c]-pyridin-2-yl)carbonyl]amino]acetyl]-o-phenylene]-dioxy]diacetic acid trifluoroacetate The title compound was prepared from the compounds of Referential Examples 2 and 9.

(a) Di-t-butyl [[4-[[[(5-t-butoxycarbonyl-3-methyl-4,5,6,7-tetrahydrothieno[3,2-c]pyridin-2-yl)carbonyl]amino]acetyl]-o-phenylene]dioxy]diacetate ¹H-NMR (CDCl₃) δ: 1.48 (s, 9H), 1.50 (s, 9H), 2.42 (s, 3H), 2.84 (brs, 2H), 3.72 (brs, 2H), 4.38 (brs, 2H), 4.66 (s, 3H), 4.70 (s, 2H), 4.84 (d, J=4.2 Hz, 2H), 6.85 (d, J=8.3 Hz, 1H), 6.90 (brs, 1H), 7.51 (d, J=2.0 Hz, 1H), 7.63 (dd, J=2.0, 8.3 Hz, 1H). SIMS (m/z): 675 (M⁺+1).

(b) Title compound

¹H-NMR (DMSO-hd6) δ: 2.32 (s, 3H), 3.04 (brs, 2H), 3.43 (brs, 2H), 4.14 (s, 2H), 4.67 (d, J=3.9 Hz, 2H), 4.80 (s, 2H), 4.85 (s, 2H), 7.01 (d, J=8.5 Hz, 1H), 7.43 (d, J=1.8 Hz, 1H), 7.70 (dd, J=1.8, 8.5 Hz, 1H). SIMS (m/z): 463 (M⁺+1).

Example 28

[[4-[[[(3-benzyl-4,5,6,7-tetrahydrothieno[3.2-c]-pyridin-2-yl)carbonyl]amino]acetyl]-o-phenylene]-dioxy]diacetic acid trifluoroacetate The title compound was prepared from the compounds of Referential Examples 3 and 9.

(a) Di-t-butyl [[4-[[[(3-benzyl-5-t-butoxycarbonyl-4,5,6,7-tetrahydrothieno[3,2-c]pyridin-2-yl)carbonyl]amino]acetyl]-o-phenylene]dioxy]diacetate ¹H-NMR (CDCl₃) δ: 1.48 (s, 9H), 1.50 (s, 9H), 2.84 (brs, 2H), 3.83 (brs, 2H), 4.23 (s, 2H), 4.31 (s, 2H), 4.65 (s, 2H), 4.82 (d, J=4.4 Hz, 2H), 6.84 (d, J=8.5 Hz, 1H), 6.88 (brs, 1H), 7.17–7.26 (m, 5H), 7.49 (d, J=1.8 Hz, 1H), 7.60 (dd, J=1.8, 8.5 Hz, 1H). SIMS (m/z): 751 (M⁺+1).

(b) Title compound

¹H-NMR (DMSO-d₆) δ: 3.01 (brs, 2H), 3.88 (brs, 2H), 4.25 (brs, 2H), 4.68 (d, J=5.4 Hz, 2H), 4.73 (s, 2H), 4.76 (s, 2H), 4.80 (s, 2H), 7.00 (d, J=8.5 Hz, 1H), 7.17–7.29 (m, 5H), 7.43 (s, 1H), 7.68 (d, J=8.5 Hz, 1H). SIMS (m/z): 539 (M⁺+1).

Example 29

[[4-[[[(4,5,6,7-tetrahydrothieno[3.2-c]pyridin-2-yl)-carbonyl]amino]acetyl]-o-phenylene]dioxy]diacetic acid trifluoroacetate The title compound was prepared from the compounds of Referential Examples 4 and 9. This compound is identical with the compound of Example 13.

(a) Di-t-butyl [[4-[[[(5-t-butoxycarbonyl-4,5,6,7-tetrahydrothieno[3,2-c]pyridin-2-yl)carbonyl]amino]acetyl]-o-phenylene]dioxy]diacetate ¹H-NMR (CDCl₃) δ: 1.48 (s, 9H), 1.49 (s, 9H), 1.50 (s, 9H), 2.72 (brs, 2H), 3.69 (brs, 2H), 4.64 (brs, 2H), 4.67 (s, 2H), 4.70 (s, 2H), 4.84 (d, J=4 Hz, 2H), 6.85 (d, J=9 Hz, 1H), 6.97–7.02 (m, 1H), 7.33 (s, 1H), 7.51 (d, J=9 Hz, 1H), 7.63 (dd, J=2.9 Hz, 1H). SIMS (m/z): 660 (M⁺).

(b) Title compound

¹H-NMR (DMSO-d₆) δ: 2.81 (brs, 2H), 3.23 (brs, 2H), 4.25 (m, 2H), 6.91 (d, J=8 Hz, 1H), 7.40 (s, 1H), 7.58 (s, 1H), 7.62 (d, J=8 Hz, 1H), 8.83 (brs, 1H); peaks corresponding to 6H overlap with the solvent peak. FDMS (m/z): 449 (M⁺+1).

Example 30

[[4-[[[(5,6,7,8-tetrahydro-4H-thieno[3.2-c]azepin-2-yl)-carbonyl]amino]acetyl]-o-phenylene]dioxy]diacetic acid trifluoroacetate The title compound was prepared from the compounds of Referential Examples 5 and 9.

(a) Di-t-butyl [[4-[[[(5-t-butoxycarbonyl-5,6,7,8-tetrahydro-4H-thieno[3,2-c]azepin-2-yl)carbonyl]amino]acetyl]-o-phenylene]dioxy]diacetate ¹H-NMR (CDCl₃+CD₃OD) δ: 1.37–1.55 (27H), 1.88 (s, 2H), 2.75–3.10 (m, 3H), 3.64–3.79 (m, 2H), 4.32–4.43 (m, 2H), 4.67 (s, 2H), 4.69 (s, 2H), 4.78–4.87 (m, 2H), 6.89 (d, J=8.3 Hz, 1H), 7.40–7.50 (m, 1H), 7.53 (d, J=1.9 Hz, 1H), 7.65–7.74 (m, 1H), 7.86 (d, J=8.3 Hz, 1H). EIMS (m/z): 674 (M⁺−1).

(b) Title compound

¹H-NMR (DMSO-d₆) δ: 1.87–2.02 (m, 2H), 2.95–3.13 (m, 2H), 3.70–3.76 (m, 2H), 4.24 (s, 2H), 4.51–4.86 (m, 6H), 6.98 (s, 1H), 7.42 (s, 1H), 7.51–7.76 (m, 2H), 8.75 (brs, 1H). FDMS (m/z ): 463 (M⁺+1).

Example 31

[[4-[[[(5,6,7,8-tetrahydro-4H-thieno[2,3-d]azepin-2-yl)-carbonyl]amino]acetyl]-o-phenylene]dioxy]diacetic acid trifluoroacetate The title compound was prepared from the compounds of Referential Examples 6 and 9.

(a) Di-t-butyl [[4-[[[(5-t-butoxycarbonyl-5,6,7,8-tetrahydro-4H-thieno[2,3-d]azepin-2-yl)carbonyl]amino]acetyl]-o-phenylene]dioxy]diacetate ¹H-NMR (CDCl₃) δ: 1.47–1.54 (27H), 2.79–3.06 (m, 4H), 3.49–3.70 (m, 4H), 4.67 (s, 2H), 4.70 (s, 6H), 4.84 (d, J=10.3 Hz, 2H), 6.85 (d, J=8.4 Hz, 1H), 7.30 (s, 1H), 7.50 (d, J=1.9 Hz, 1H), 7.63 (dd, J=1.9, 8.4 Hz, 1H). EIMS (m/z): 463 (M⁺−1).

(b) Title compound

¹H-NMR (DMSO-d₆) δ: 2.85–2.39 (8H), 4.57–4.86 (m, 6H), 6.99 (d, J=8.4 Hz, 1H), 7.42 (s, 1H), 7.58 (s, 1H), 7.67 (d, J=8.4 Hz, 1H), 8.69 (brs, 1H). FDMS (m/z): 463 (M⁺+1).

Example 32

[[4-[N-[(4,5,6,7-tetrahydrothieno[3,2-c]pyridin-2-yl)-carbonyl]methyl]carbamoyl]-o-phenylene]dioxy]diacetic acid trifluoroacetate The title compound was prepared from the compounds of Referential Examples 8 and 10.

(a) Di-t-butyl [[4-[N-(5-t-butyl-4,5,6,7-tetrahydrothieno[3,2-c]pyridin-2-yl)]carbonyl]methyl]carbonyl-o-phenylene]dioxy]diacetate ¹H-NMR (CDCl₃) δ: 1.48 (s, 9H), 1.49 (s, 9H), 1.50 (s, 9H), 2.92 (brt, 2H), 3.75 (brt, 2H), 4.53 (s, 2H), 4.66 (s, 4H), 4.80 (d, J=3.9 Hz, 2H), 6.85 (d, J=7.8 Hz, 1H), 7.06 (t, J=3.9 Hz, 1H), 7.43 (s, 1H), 7.56 (s, 1H), 7.42 (dd, J=2.0, 7.8 Hz, 1H). FDMS (m/z): 661 (M⁺+1).

Title compound

¹H-NMR (DMSO-d₆) δ: 3.10 (t, J=5.3 Hz, 2H), 3.43 (t, J=5.3 Hz, 2H), 4.23 (s, 2H), 4.60 (d, J=5.3 Hz, 2H), 4.73 (s, 2H), 4.77 (s, 2H), 6.97 (d, J=8.4 Hz, 1H), 7.40 (d, J=1.9 Hz, 1H), 7.92 (s, 1H), 8.82 (t, J=5.3 Hz, 1H).

Example 33

Diethyl [[4-[[2-[(4,5,6,7-tetrahydrothieno[3,2-c]pyridin-2-yl)-carbonyl]amino]ethyl]-o-phenylene]dioxy]diacetate trifluoroacetate The title compound was prepared from the compounds of Referential Examples 1 and 20.

(a) Diethyl [[4-[[2-[(5-t-butoxycarbonyl-4,5,6,7-tetrahydrothieno[3,2-c]pyridin-2 -yl)carbonyl]amino]ethyl]-o-phenylene]dioxy]diacetate ¹H-NMR (CDCl₃) δ: 1.28 (m, 6H), 1.48 (s, 9H), 2.81 (m, 4H), 3.58 (m, 2H), 3.70 (m, 2H), 4.22 (m, 4H), 4.42 (s, 2H), 4.67 (s, 2H), 4.68 (s, 2H), 6.75–7.17 (m, 4H).

(b) Title compound

¹H-NMR (CD₃OD) δ: 1.27 (t, J=7.0 Hz, 3H), 1.28 (t, J=7.0 Hz, 3H), 2.81 (m, 2H), 3.17 (m, 2H), 3.54 (m, 4H), 4.22 (m, 4H), 4.28 (s, 4H), 4.70 (s, 2H), 4.71 (s, 2H), 6.82 (dd, J=3.6, 8.3 Hz, 1H), 6.86 (d, J=3.6 Hz, 1H), 6.88 (d, J=8.3 Hz, 1H), 7.38 (s, 1H).

Example 34

Diethyl [[4-[[[(4,5,6,7-tetrahydrothieno[3,2-c]pyridin2-yl)-carbonyl]amino]acetyl]-o-phenylene]dioxy]diacetate trifluoroacetate The title compound was prepared from the compounds of Referential Examples 1 and 21.

(a) Diethyl [[4-[[2-[(5-t-butoxycarbonyl-4,5,6,7-tetrahydrothieno[3,2-c]pyridin-2-yl)carbonyl]amino]acetyl]-o-phenylene]dioxy]diacetate ¹H-NMR (CDCl₃) δ: 1.28–1.32 (m, 6H), 1.49 (s, 9H), 2.87 (brs, 2H), 3.73 (brs, 2H), 4.25–4.31 (m, 4H), 4.49 (brs, 2H), 4.78 (s, 2H), 4.81 (s, 2H), 4.84 (d, J=4 Hz, 2H), 6.89 (d, J=8 Hz, 1H), 6.98–7.03 (m, 1H), 7.32 (s, 1H), 7.55 (d, J=2 Hz, 1H), 7.65 (dd, J=2.8 Hz, 1H). EIMS (m/z): 604 (M⁺).
(b) Title compound
¹H-NMR (CD₃OD) δ: 1.29 (t, J=7 Hz, 6H), 3.20 (t, J=6 Hz, 2H), 3.58 (t, J=6 Hz, 2H), 4.25 (q, J=7 Hz, 2H), 4.26 (q, J=7 Hz, 2H), 4.79 (s, 2H), 4.82 (s, 4H), 7.05 (d, J=8 Hz, 1H), 7.53 (s, 1H), 7.60 (d, J=2 Hz, 1H), 7.74 (dd, J=2.8 Hz, 1H).

Example 35

[[4-[[N-[3-(piperidin-4-yl)propionyl]amino]acetyl]-o-phenylene]dioxy]diacetic acid trifluoroacetate The title compound was prepared from 3-(1-t-butoxycarbonylpiperidin-4-yl)propionic acid and the compound of Referential Example 9.
(a) Di-t-butyl [[4-[[N-[3-(1-t-butoxycarbonylpiperidin-4-yl)propionyl]amino]acetyl]-o-phenylene]dioxy]diacetate
¹H-NMR (CDCl₃) δ: 1.05–1.18 (m, 2H), 1.45 (s, 9H), 1.48 (s, 9H), 1.50 (s, 9H), 1.58–1.70 (m, 5H), 2.30–2.37 (m, 2H), 2.62–2.72 (m, 2H), 4.02–4.17 (m, 2H), 4.66 (s, 2H), 4.69 (s, 4H), 6.53 (brs, 1H), 6.83 (d, J=9 Hz, 1H), 7.48 (s, 1H), 7.60 (d, J=9 Hz, 1H). FDMS (m/z): 634 (M⁺).
(b) Title compound
¹H-NMR (D₂O) δ: 1.32–1.44 (m, 2H), 1.53–1.67 (m, 3H), 1.88–1.98 (m, 2H), 2.34–2.45 (m, 2H), 2.90–3.02 (m, 2H), 3.34–3.47 (m, 2H), 4.65 (s, 2H), 4.84 (s, 2H), 4.88 (s, 2H), 7.04 (d, J=9 H), 7.45 (s, 1H), 7.66 (d, J=9 Hz, 1H). SIMS (m/z): 423 (M⁺+1).

Example 36

[[4-[[N-[4-(piperidin-4-yl)butyryl]amino]acetyl]-o-phenylene]dioxy]diacetic acid trifluoroacetate The title compound was prepared from 4-(1-t-butoxycarbonylpiperidin-4-yl)butyric acid and the compound of Referential Example 9.
(a) Di-t-butyl [[4-[[N-[4-(1-t-butoxycarbonylpiperidin-4-yl)butyryl]amino]acetyl]-o-phenylene]dioxy]diacetate
¹H-NMR (CDCl₃) δ: 1.04 (m, 2H), 1.28 (m, 2H), 1.45 (s, 9H), 1.48 (s, 9H), 1.50 (s, 9H), 1.60–1.72 (m, 5H), 2.30 (m, 2H), 2.67 (m, 2H), 4.07 (brs, 1H), 4.66 (s, 2H), 4.69 (s, 2H), 4.70 (s, 2H), 6.54 (brs, 1H), 6.83 (d, J=8.5 Hz, 1H), 7.48 (d, J=2.1 Hz, 1H), 7.60 (dd, J=2.1, 8.5 Hz, 1H). FDMS (m/z): 649 (M⁺+1).
(b) Title compound
¹H-NMR (D₂O) δ: 1.25–1.40 (m, 4H), 1.52–1.68 (m, 3H), 1.93 (d, J=11.1 Hz, 2H), 2.38 (m, 2H), 2.96 (t, J=12.5 Hz, 2H), 3.40 (d, J=12.5 Hz, 2H), 4.66 (s, 2H), 4.85 (s, 2H), 4.89 (s, 2H), 7.06 (d, J=8.3 Hz, 1H), 7.48 (d, J=1.9 Hz, 1H), 7.70 (dd, J=1.9, 8.3 Hz, 1H).

Example 37

[[4-[[N-[2-(piperidin-4-yl)acetyl]-N-methylamino]-acetyl]-o-phenylene]dioxy]diacetic acid trifluoroacetate The title compound was prepared from 2-(1-t-butoxycarbonylpiperidin-4-yl)acetic acid and the compound of Referential Example 11.
(a) Di-t-butyl [[4-[[N-[2-(1-t-butoxycarbonylpiperidin-4-yl)acetyl]-N-methylamino]acetyl]-o-phenylene]dioxy]diacetate FDMS (m/z): 634 (M⁺).
(b) Title compound
¹H-NMR (D₂O) δ: 1.48, 1.51 (m, 2H), 1.92, 2.00 (m, 2H), 2.10 (m, 1H), 2.28, 2.54 (d, J=6.9 Hz, 2H), 2.96, 3.15 (s, 3H), 3.10 (m, 2H), 3.42 (m, 2H), 4.84 (s, 2H), 4.85 (s, 2H), 4.88 (s, 2H), 7.04, 7.12 (d, J=8.6 Hz, 1H), 7.45, 7.49 (s, 1H), 7.67, 7.72 (d, J=8.6 Hz, 1H).

Example 38

3-[4-[N-[3-(piperidin-4-yl)propionyl]amino]acetyl]-phenylpropionic acid trifluoroacetate The title compound was prepared form 3-(1-t-butoxycarbonylpiperidin-4-yl)propionic acid and the compound of Referential Example 12.
(a) Diphenylmethyl 3-[4-[N-[3-(1-t-butoxycarbonylpiperidin-4-yl)propionyl]amino]-acetyl]phenylpropionate
¹H-NMR (CDCl₃) δ: 1.06–1.18 (m, 2H), 1.15 (s, 9H), 1.60–1.73 (m, 4H), 2.34 (t, J=8 Hz, 2H), 2.61–2.73 (m, 2H), 2.78 (t, J=8 Hz, 2H), 3.05 (t, J=8 Hz, 2H), 4.02–4.15 (m, 1H), 4.71 (d, J=4 Hz, 2H), 6.52–6.56 (m, 1H), 6.87 (s, 1H), 7.24–7.34 (m, 12H), 7.85 (d, J=8 Hz, 1H). SIMS (m/z): 613 (M⁺+1).
(b) Title compound
¹H-NMR (CDCl₃) δ: 1.34–1.46 (m, 2H), 1.60–1.70 (m, 2H), 1.98 (d, J=14 Hz, 2H), 2.44 (d, J=7 Hz, 2H), 2.73–2.81 (m, 2H), 2.93–3.08 (m, 4H), 3.43 (d, J=13 Hz, 2H), 4.75 (s, 2H), 7.47 (d, J=8 Hz, 2H), 7.95 (d, J=8 Hz, 2H). SIMS (m/z): 347 (M⁺+1).

Example 39

4-[2-[[(4,5,6,7-tetrahydrothieno[3,2-c]pyridin-2-yl)-carbonyl]amino]ethyl]phenoxyacetic acid trifluoroacetate The title compound was prepared from the compounds of Referential Examples 1 and 14.
(a) Ethyl 4-[2-[[(5-t-butoxycarbonyl-4,5,6,7-tetrahydrothieno[3,2-c]pyridin-2-yl)carbonyl]amino]ethyl]phenoxyacetate This compound was prepared according to the method described in Example 1 (a).
¹H-NMR (D₂O) δ: 1.30 (t, J=7.2 Hz, 3H), 1.48 (s, 9H), 2.84 (t, J=6.8 Hz, 4H), 3.63 (q, J=6.8 Hz, 2H), 3.71 (brs, 2H), 4.28 (q, J=7.2 Hz, 2H), 4.45 (brs, 2H), 4.61 (s, 2H), 6.87 (d, J=8.6 Hz, 2H), 7.11 (s, 1H), 7.14 (d, J=8.6 Hz, 2H). EIMS (m/z): 488 (M⁺).

(b) To the solution of the compound prepared in (a) (250 mg) in ethanol was added 1N sodium hydroxide (2.6 ml), and the mixture was stirred under ice-cooling for 3 hours. After the reaction mixture was concentrated under reduced pressure, ethyl acetate and water were added. The mixture was acidified with 1N hydrochloric acid. The organic layer was washed with water, dried over anhydrous magnesium sulfate and concentrated under reduced pressure to give 214 mg of 4-[2-[[(5-t-butoxycarbonyl-4,5,6,7-tetrahydrothieno [3,2-c]pyridin-2-yl)carbonyl]amino]ethyl]phenoxyacetic acid (yield, 91%).
¹H-NMR (CDCl₃) δ: 1.49 (s, 9H), 2.92 (m, 4H), 3.45 (brs, 2H), 3.73 (m, 2H), 4.53 (brs, 2H), 4.68 (s, 2H), 6.87 (brs, 2H), 7.10 (brs, 2H), 7.27 (s, 1H). FDMS (m/z): 461 (M⁺+1).

(c) The title compound was prepared according to the method described in Example 1 (b).
¹H-NMR (CD₃OD) δ: 2.92 (t, J=7.2 Hz, 2H), 3.26 (t, J=6.1 Hz, 2H), 3.60 (t, J=7.2 Hz, 2H), 3.64 (t, J=6.1 Hz, 2H), 4.37 (s, 2H), 4.70 (s, 2H), 4.97 (s, 2H), 6.95 (d, J=8.3 Hz, 2H), 7.24 (d, J=8.3 Hz, 2H), 7.47 (s, 1H). FDMS (m/z): 361 (M$^+$+1).

Example 40

[[4-[2-[N-[(4,5,6,7-tetrahydrothieno[3,2-c]pyridin-2-yl)methyl]amino]ethyl]-o-phenylene]dioxy]diacetic acid trifluoroacetate (a) To the solution of the compound prepared in Referential Example 7 (500 mg) in methanol (20 ml) were added the compound prepared in Referential Example 20 (822 mg) and sodium cyanoborohydride (235 mg), and the mixture was stirred at room temperature for 16 hours. After the reaction mixture was concentrated under reduced pressure, the residue was purified by column chromatography on silica gel. Elution with chloroform: methanol=10:1 gave 530 mg of diethyl [[4-[2-[N-[(5-t-butoxycarbonyl- 4,5,6,7-tetrahydrothieno[3,2-c]pyridin-2yl)methyl])methyl]amino]ethyl]-o-phenylene]dioxy]diacetate (yield, 49.1%).

$^1$H-NMR (CDCl$_3$) δ: 1.28 (m, 6H), 1.48 (s, 9H), 2.80 (m, 6H), 3.78 (brs, 2H), 3.89 (s, 2H), 4.24 (m, 4H), 4.41 (brs, 2H), 4.69 (m, 4H), 6.57 (s, 1H), 6.75–6.85 (m, 3H).

(b) To the solution of the compound prepared in (a) (78 mg) in methanol (1 ml) was added 1N sodium hydroxide (5 ml), and the mixture was stirred at room temperature for 1 hour and then concentrated under reduced pressure. After anisole (1 ml) and trifluoroacetic acid (5 ml) were added to the residue, the mixture was stirred for 3 hours. The reaction mixture was taken into isopropyl ether. Deposits were collected by filtration, dissolved in water, adsorbed on HP-20, washed with water, and eluted with water: acetone=10:1 to give 50 mg of the title compound (yield, 87.9%).

$^1$H-NMR (D$_2$O+DCl) δ: 2.81 (m, 2H), 3.01 (m, 2H), 3.16 (m, 2H), 3.42 (m, 2H), 4.13 (s, 2H), 4.24 (s, 2H), 4.67 (s, 4H), 6.82 (m, 4H).

Example 41

[[4-[2-[N-[(4,5,6,7-tetrahydrothieno[3,2-c]pyridin-2-yl)methyl]-N-acetylamino]ethyl]-o-phenylene]dioxy]diacetic acid trifluoroacetate (a) To the solution of the compound prepared in Example 23 (a) (309 mg) in pyridine (2 ml) was added acetic anhydride (1 ml), and the mixture was stirred at room temperature for 3 hours. The reaction mixture was dissolved in ethyl acetate, washed with water, dried over anhydrous magnesium sulfate. After the solvents were evaporated, the residue was purified by column chromatography on silica gel, and the fraction eluted with ethyl acetate: n-hexane=3:1 gave 163 mg of diethyl [[4-[2-[N-[(5-t-butoxycarbonyl-4,5,6,7-tetrahydrothieno[3,2-c]pyridin-2-yl)methyl]-N-acetylamino]ethyl]-o-phenylene]dioxy]diacetate (yield, 49.2%).

$^1$H-NMR (CDCl$_3$) δ: 1.28 (t, J=7.2 Hz, 3H), 1.29 (t, J=7.2 Hz, 3H), 1.48 (s, 9H), 1.92, 2.17 (double s, 3H), 2.76 (m, 4H), 3.49 (m, 2H), 3.69 (brs, 2H), 4.25 (q, J=7.2 Hz, 2H), 4.26 (q, J=7.2 Hz, 2H), 4.34, 4.57 (double s, 2H), 4.41 (brs, 2H), 4.69 (s, 2H), 4.70 (s, 2H), 6.53 (s, 1H), 6.64–6.84 (m, 3H).

(b) Reaction was performed according to the method described in Example 23 (b) to give the title compound.

$^1$H-NMR (D$_2$O+DCl) δ: 1.46, 1.90 (double s, 3H), 2.54 (m, 2H), 2.81 (brs, 2H), 3.27 (m, 2H), 3.37 (m, 2H), 3.96 (m, 2H), 4.27 (m, 2H), 4.46 (s, 2H), 4.49 (s, 2H), 6.41–6.63 (m, 4H).

Example 42

Di-(5-methyl-2-oxodioxol-4-yl)methyl [[4-[[(4,5,6,7-tetrahydrothieno[3,2-c]pyridin-2-yl)-carbonyl]amino]acetyl]-o-phenylene]dioxy]diacetic acid trifluoroacetate (a) To the solution of the compound prepared in Example 17 (a) (2 g) in THF (50 ml) was added an aqueous solution (50 ml) of sodium hydroxide (240 mg), and the mixture was stirred at room temperature for 20 minutes. After THF was evaporated under reduced pressure, the concentrated reaction mixture was acidified to pH 3.5 with 5N hydrochloric acid. Crystals deposited were collected by filtration and dried to give 1.21 g of [[4-[[[(5-t-butoxycarbonyl-4,5,6,7-tetrahydrothieno[3,2-c]pyridin-2-yl)carbonyl]amino]acetyl]-o-phenylene]dioxy]diacetic acid.

$^1$H-NMR (D$_2$O) δ: 1.52 (s, 9H), 2.90 (brs, 2H), 3.74 (brs, 2H), 4.50 (brs, 2H), 4.61 (s, 2H), 4.66 (s, 2H), 4.86 (s, 2H), 7.01 (d, J=9 Hz, 1H), 7.44 (d, J=2 Hz, 1H), 7.48 (s, 1H), 7.74 (dd, J=2 Hz, 9 Hz, 1H).

(b) To the solution of the compound prepared in (a) (100 mg) in DMF (3 ml) were added 4-bromomethyl-5-methyl-2-oxodioxole (104 mg) and cesium fluoride (82 mg), and the mixture was stirred at room temperature for 19 hours. Water (10 ml) was added to the reaction mixture. The resulting mixture was extracted with ethyl acetate, washed with water and dried over anhydrous magnesium sulfate. After the solvents were evaporated, the residue was purified by column chromatography on silica gel, and the fraction eluted with chloroform: methanol=20:1 gave 122 mg of di-(5-methyl-2-oxodioxol-4-yl)methyl [[4-[[[(5-t-butoxycarbonyl-4,5,6,7-tetrahydrothieno[3,2-c]pyridin-2-yl)carbonyl]amino]acetyl]-o-phenylene]dioxy]diacetate.

$^1$H-NMR (CDCl$_3$) δ: 1.50 (s, 9H), 2.19 (s, 6H), 2.88 (brs, 2H), 3.74 (brs, 2H), 4.51 (brs, 2H), 4.83 (s, 2H), 4.85 (d, J=4 Hz, 2H), 4.86 (s, 2H), 5.02 (s, 2H), 6.90 (d, J=8 Hz, 1H), 6.97–7.01 (brs, 1H), 7.35 (s, 1H), 7.51 (d, J=2 Hz, 1H), 7.66 (dd, J=2 Hz, 8 Hz, 1H). SIMS (m/z): 773 (M$^+$+1).

(c) The compound prepared in (b) was subjected to reaction according to the method described in Example 1 (b) to give the title compound.

$^1$H-NMR (D$_2$O)δ: 2.13 (s, 3H), 2.15 (s, 3H), 3.25 (brs, 2H), 3.60–3.64 (m, 2H), 4.37 (brs, 2H), 4.97 (s, 2H), 5.02 (s, 2H), 5.11 (s, 4H), 7.07 (d, J=8 Hz, 1H), 7.48 (d, J=2 Hz, 1H), 7.55 (s, 1H), 7.74 (dd, J=2 Hz, 8 Hz, 1H). FDMS (m/z): 673 (M$^+$+1).

Example 43

[[4-[2-[2-(piperidin-4-yl)ethyl]oxazol-5-yl]-o-phenylene]dioxy]diacetic acid 1/2 sulfate The compound prepared in Example 18 (200 mg) was dissolved in concentrated sulfuric acid (1 ml). The solution was stirred at room temperature for 2 hours. Crystals deposited were collected by filtration, washed with water and dried to give 76 mg of the title compound (yield, 50%).

$^1$H-NMR (D$_2$O) δ: 1.28–1.45 (m, 2H), 1.46–1.68 (m, 3H), 1.82–1.95 (m, 2H), 2.58–2.70 (m, 2H), 2.85–2.88 (m, 2H), 3.33–3.47 (m, 2H), 4.55 (s, 2H), 4.58 (s, 2H), 6.74 (d, J=9 Hz, 1H), 6.79 (s, 1H), 6.91 (d, J=9 Hz, 1H), 6.99 (s, 1H). FDMS (m/z): 405 (M$^+$+1).

Example 44

2-[[4,5,6,7-tetrahydrothieno[3,2-c]pyridin-2-yl)-
carbonylamino]acetyl]pyridin-5-yloxyacetic acid
trifluoroacetate (a) To the solution of oxalyl chloride (10 μl) in dichloromethane (0.5 ml) was added the solution of dimethylsulfoxide (17 μl ) in dichloromethane (0.5 ml) at −78° C., and the mixture was stirred for 4 minutes. The solution of the compound prepared in Example 21 (a) (58 mg) in dichloromethane (1 ml) was added to this solution. The mixture was stirred for 15 minutes. Triethylamine (76 μl) was further added to the mixture to continue the reaction at −78° C. for 15 minutes and at 0° C. for 30 minutes. A saturated aqueous ammonium chloride solution was added to the mixture to terminate the reaction. The mixture was extracted with ethyl acetate, washed with water and brine and dried over anhydrous magnesium sulfate. After the solvents were evaporated under reduced pressure, the residue was purified by column chromatography on silica gel. A fraction eluted with ethyl acetate: n-hexane (1:2) gave 12 mg of t-butyl 2-[[(5-t-butoxycarbonyl-4,5,6,7-tetrahydrothieno[3,2-c]pyridin-2-yl)carbonylamino]acetyl]pyridin-5-yloxyacetate.

$^1$H-NMR (CDCl$_3$) δ: 1.49 (s, 9H), 1.50 (s, 9H), 2.87 (m, 2H), 3.73 (m, 2H), 4.50 (s, 2H), 4.66 (s, 2H), 5.09 (d, J=4.7 Hz, 2H), 6.90 (t, J=4.7 Hz, 1H), 7.27 (dd, J=2.8, 8.9 Hz, 1H), 7.32 (s, 1H), 8.07 (d, J=8.9 Hz, 1H), 8.36 (d, J=2.8 Hz, 1H).

(b) The compound prepared in (a) was treated in the same manner as in Example 1 (b) to give 10 mg of the title compound (yield, 73%).

$^1$H-NMR (CD$_3$OD) δ: 3.20 (t, J=5.8 Hz, 2H), 3.31 (s, 2H), 3.58 (t, J=5.8 Hz, 2H), 4.32 (s, 2H), 4.98 (s, 2H), 6.61 (s, 1H), 7.48 (dd, J=2.8, 8.9 Hz, 1H), 8.05 (d, J=8.9 Hz, 1H), 8.40 (d, J=2.8 Hz, 1H). SIMS (m/z): 376 (M$^+$+1).

Example 45

[[4-[[2-[(4,5,6,7-tetrahydrothieno[3,2-c]pyridin-2-yl)-
carbonyl]amino]-1-hydroxyethyl]-o-phenylene]dioxy]-
diacetic acid trifluoroacetate (a) To the solution of the compound prepared in Example 18 (a) (634 mg) in ethanol (6 ml) was added sodium borohydride (52 mg), and the mixture was stirred at room temperature for 3 hours. The reaction mixture was extracted with ethyl acetate, washed with water and dried over anhydrous magnesium sulfate. After the solvents were evaporated, the residue was purified by column chromatography on silica gel, and the fraction eluted with ethyl acetate: n-hexane (2:1) gave 370 mg of di-t-butyl [[4-[[2-[(5-t-butoxycarbonyl-4,5,6,7-tetrahydrothieno[3,2-c]pyridin-2-yl)carbonyl]amino]-1-hydroxyethyl]-o-phenylene]dioxy]diacetate (yield, 58.2%).

$^1$H-NMR (CDCl$_3$ ) δ: 1.47 (27H), 2.85 (brs, 2H), 3.18 (brs, 1H), 3.43 (m, 1H), 3.72 (brs, 2H), 3.82 (m, 1H), 4.45 (s, 2H), 4.59 (s, 2H), 4.60 (s, 2H), 4.86 (m, 1H), 6.35 (brs, 1H), 6.82 (d, J=8.0 Hz, 1H), 6.92 (m, 2H), 7.20 (s, 1H).

(b) The compound prepared in (a) was treated in the same manner as in Example 1 (b) to give the title compound.

$^1$H-NMR (DMSO-D6) δ: 3.05 (m, 2H), 3.74 (m, 1H), 4.18 (m, 2H), 4.60–4.75 (m, 4H), 6.77–6.91 (m, 4H); peaks corresponding to 4H overlap with the peaks of the solvent.

Example 46

4-[[2-(4,5,6,7-tetrahydrothieno[3,2-c]pyridin-2-yl)-
carbonyl]thiazol-4-yl]phenoxyacetic acid
trifluoroacetate (a) 4'-(4-methoxybenzyl)oxyacetophenone was subjected to reaction according to the method described in Referential Example 15 (b) to give 4'-(p-methoxybenzyl)oxy-2-bromoacetophenone.

$^1$H-NMR (CDCl$_3$) δ: 3.82 (s, 3H), 4.40 (s, 2H), 5.07 (s, 2H), 6.93 (d, J=8.9 Hz, 2H), 7.02 (d, J=8.9 Hz, 2H), 7.35 (d, J=8.9 Hz, 2H), 7.97 (d, J=8.9 Hz, 2H). SIMS (m/z ): 335 (M$^+$+1).

(b) Phosphorus pentasulfide (198 mg ) and formamide (2 ml) were mixed and stirred at room temperature overnight. The solution of the compound prepared in (a) (1.34 g) in THF (5 ml) was added to this mixture. The resulting mixture was stirred for 1 hour. After saturated sodium hydrogen carbonate and water were added, the mixture was extracted with ethyl acetate, washed with water and dried over anhydrous magnesium sulfate. The solvents were evaporated. Crystals thus obtained were washed with ether and dried to give 689 mg of 4-[4-(p-methoxybenzyl)oxyphenyl]thiazole (yield, 58%).

$^1$H-NMR (CDCl$_3$) δ: 3.82 (s, 3H), 5.04 (s, 2H), 6.92 (d, J=8.6 Hz, 2H), 7.03 (d, J=8.6 Hz, 2H), 7.38 (d, J=8.6 Hz, 2H), 7.40 (d, J=1.9 Hz, 1H), 7.86 (d, J=8.6 Hz, 2H), 8.85 (d, J=1.9 Hz, 1H). EIMS (m/z): 297 (M$^+$).

(c) The solution of the compound prepared in (b) (150 mg) in THF (3 ml) was cooled to −78° C., and n-butyl lithium (1.5M, n-hexane solution, 0.33 ml) was added dropwise. The mixture was stirred at the same temperature for 10 minutes. To this solution was added dropwise the solution of the compound prepared in Referential Example 7 (133 mg) in THF (2 ml), and the mixture was stirred at −78° C. for 30 minutes. The reaction mixture was diluted with ether, washed with water, and dried over anhydrous magnesium sulfate. After the solvents were evaporated, the residue was purified by column chromatography on silica gel with an eluent system (n-hexane: ethyl acetate=2:1) to give 125 mg of 2-[1(5-t-butoxycarbonyl-4,5,6,7-tetrahydrothieno[3,2-c]pyridin-2-yl)-1-hydroxymethyl]-4-[4-(p-methoxybenzyl)oxyphenyl]thiazole (yield, 44%).

$^1$H-NMR (CDCl$_3$) δ: 1.47 (s, 9H), 2.81 (brs, 2H), 3.63 (brs, 1H, disappeared by D$_2$O), 3.69 (brs, 2H), 3.81 (s, 3H), 4.43 (brs, 2H), 5.03 (s, 2H), 6.23 (d, J=4.0 Hz, 1H), 6.82 (s, 1H), 6.92 (d, J=8.5 Hz, 2H), 7.01 (d, J=8.5 Hz, 2H), 7.34 (s, 1H), 7.37 (d, J=8.5 Hz, 2H), 7.82 (d, J=8.5 Hz, 2H). EIMS (m/z): 564 (M$^+$).

(d) To the solution of the compound prepared in (c) (290 in dichloromethane (6 ml) was added under ice-cooling pyridinium chlorochromate (220 mg), and the mixture was stirred under ice-cooling for 2 hours and at room temperature for 1 hour. The reaction mixture was diluted with ethyl acetate. Insolubles were removed by filtration through celite. The filtrate was washed with saturated sodium hydrogen carbonate and water and dried over anhydrous magnesium sulfate. After the solvents were evaporated, the residue was purified by column chromatography on silica gel with the eluent system of n-hexane: ethyl acetate=2:1 to give 174 mg of 2-[(5-t-butoxycarbonyl-4,5,6,7-tetrahydrothieno[3,2-c]pyridin-2-yl)carbonyl]-4-[4-(p-methoxybenzyl)oxyphenyl]thiazole (yield, 60.2%).

$^1$H-NMR (CDCl$_3$) δ: 1.51 (s, 9H), 2.97 (brs, 2H), 3.77 (brs, 2H), 3.83 (s, 3H), 4.59 (brs, 2H), 5.07 (s, 2H), 6.94 (d, J=8.6 Hz, 2H), 7.09 (d, J=8.6 Hz, 2H), 7.39 (d, J=8.6 Hz, 2H), 7.71 (s, 1H), 7.92 (d, J=8.6 Hz, 2H), 8.34 (brs, 1H). SIMS (m/z): 563 (M⁺+1).

(e) The compound prepared in (d) (170 mg), anisole (0.2 ml) and trifluoroacetic acid (2 ml) were reacted at room temperature for 30 minutes. Diisopropyl ether (10 ml) was added to the reaction mixture, and precipitates was collected by filtration. Precipitates thus obtained (137 mg) was dissolved in dichloromethane (2 ml). Di-t-butyl dicarbonate (72 mg), triethylamine (0.15 ml) and DMF (0.5 ml) were added to the solution. The mixture was stirred at room temperature for 2 hours. The reaction mixture was diluted with ethyl acetate, washed with water and dried over anhydrous magnesium sulfate. After the solvents were evaporated, the residue was purified by column chromatography on silica gel with an eluent system of n-hexane: ethyl acetate=3:1 to give 125 mg of 2-[(5-t-butoxycarbonyl-4,5,6,7-tetrahydrothieno[3,2-c]pyridin-2-yl)carbonyl]-4-(p-hydroxyphenyl]thiazole (yield, 94%).

¹H-NMR (CDCl₃) δ: 1.51 (s, 9H), 2.98 (brs, 2H), 3.78 (brs, 2H), 4.59 (brs, 2H), 6.96 (d, J=8.5 Hz, 2H), 7.69 (s, 1H), 7.86 (d, J=8.5 Hz, 2H), 8.34 (brs, 1H). EIMS (m/z): 442 (M⁺).

(f) To the solution of the compound prepared in (e) (119 mg) in DMF (2 ml) were added potassium carbonate (74 mg) and t-butyl bromoacetate (0.047 ml), and the mixture was stirred at 60°–70° C. for 1.5 hours. The reaction mixture was diluted with ethyl acetate, washed with water, and dried over anhydrous magnesium sulfate. After the solvents were evaporated, the residue was purified by column chromatography on silica gel with an eluent system of n-hexane: ethyl acetate=3:1 to give 129 mg of t-butyl 4-[[2-(5-t-butyloxycarbonyl-4,5,6,7-tetrahydrothieno[3,2-c]pyridin-2-yl)carbonyl]thiazol-4-yl]phenoxyacetate (yield, 86%).

¹H-NMR (CDCl₃) δ: 1.50 (s, 9H), 1.51 (s, 9H), 2.98 (brs, 2H), 3.78 (brs, 2H), 4.59 (s, 4H), 7.02 (d, J=8.6 Hz, 2H), 7.72 (s, 1H), 7.92 (d, J=8.6 Hz, 2H), 8.35 (brs, 1H). EIMS (m/z): 556 (M⁺).

(g) The compound prepared in (f) was treated in the same manner as described in Example 1 (b) to give the title compound.

¹H-NMR (DMSO-d₆+D₂O) δ: 3.25 (m, 2H), 3.51 (m, 2H), 4.35 (brs, 2H), 4.76 (s, 2H), 7.08 (d, J=8.7 Hz, 2H), 8.05 (d, J=8.7 Hz, 2H), 8.41 (s,1H). 8.43 (s, 1H). FDMS (m/z): 400 (M⁺).

Example 47

4-[[4-(4,5,6,7-tetrahydrothieno[3,2-c]pyridin-2-yl)-carbonyl]thiazol-2- yl]phenoxyacetic acid trifluoroacetate.

(a) To the solution of 4-(p-methoxybenzyl)oxybenzonitrile (7.18 g) in pyridine (100 ml) was added triethylamine (20 ml), and hydrogen sulfide gas was streamed 30 minutes. The mixture was stirred at room temperature for 3 hours followed by 50° C. overnight. After the solvent was evaporated under reduced pressure, the residue was taken into ether, and crystals were collected by filtration and dried to give 8.05 g of 4-(p-methoxybenzyl)oxythiobenzamide (yield, 98%). EIMS (m/z): 273 (M⁺).

(b) To the solution of the compound prepared in (a) (273 mg) in DMF (3 ml) was added chloroacetoaldehyde (40% aqueous solution, 0.3 ml), and the mixture was stirred at 60° C. for 3 hours. The reaction mixture was diluted with ethyl acetate, washed with water and dried over anhydrous magnesium sulfate. After the solvent was evaporated, the residue was taken into ether, and crystals were collected by filtration and dried to give 203 mg of 2-[4-(p-methoxybenzyl)oxyphenyl]thiazole (yield, 70%).

¹H-NMR (CDCl₃) δ: 3.82 (s, 3H), 5.04 (s, 2H), 6.93 (d, J=8.7 Hz, 2H), 7.03 (d, J=8.7 Hz, 2H), 7.25 (d, J=3.3 Hz, 1H), 7.37 (d, J=8.7 Hz, 2H), 7.80 (d, J=3.3 Hz, 1H), 7.91 (d, J=8.7 Hz, 2H). EIMS (m/z): 297 (M⁺).

(c) The compound prepared in (b) was subjected to reaction according to the method described in Example 29 (c)–(g) to give the title compound.

¹H-NMR (DMSO-d₆) δ: 3.18 (m, 2H), 3.50 (m, 2H), 4.29 (brs, 2H), 4.80 (brs, 2H), 7.09 (d, J=8.8 Hz, 2H), 8.02 (d, J=8.8 Hz, 2H), 8.06 (s, 1H), 8.68 (s, 1H).

Referential Example 22

6-t-butoxycarbonyl-4,5,6,7-tetrahydrothiazolo[5,4-c]-pyridin-2-carboxylic acid (a) 6-ethoxycarbonyl-4,5,6,7-tetrahydrothiazolo[5,4-c]pyridine The suspension of phosphorus pentasulfide (6.668 g, 30 mmole) in formamide (25 ml) was stirred overnight at room temperature. The reaction solution was taken into water, extracted with ether and dried over anhydrous magnesium sulfate. The solvents were evaporated to give thioformamide (3.964 g).

To the thioformamide this obtained was added 3-chloro-1-ethoxycarbonylpiperidin-4-one (5.141 g, 25 mmole) in ethanol (100 ml) prepared according to the method described in Tetrahedron, 39, 3767 (1983) and heated at reflux in the presence of Molecular Sieves 4A for 15 hours. The reaction mixture was cooled to room temperature. After a saturated aqueous sodium hydrogen carbonate solution was added to the mixture under ice-cooling, ethanol was evaporated under reduced pressure. The reaction mixture was extracted with chloroform, washed with brine and dried over anhydrous magnesium sulfate. The solvent was evaporated under reduced pressure to give 6.175 g of a crude product. The product was purified by column chromatography on silica gel (C-200=150 g, eluent:CHCl₃) to give 3.213 g of the title compound as a clear pale yellow oily product (yield, 60.5%).

¹H-NMR (CDCl₃) δ: 1.30 (t, J=7.03 Hz, 3H), 2.88–3.00 (m, 2H), 3.74–3.87 (s, 2H), 4.20 (q, J=7.03 Hz, 2H), 4.73 (s, 2H), 8.68 (s, 1H).

(b) 4,5,6,7-tetrahydrothiazolo[5,4-c]pyridine

To the compound prepared in Referential Example 20 (a) (3.20 g, 15.6 mmole) was added 3.5N KOH (50 ml), and the mixture was heated at reflux 1 hour. The reaction mixture was cooled to room temperature, and concentrated hydrochloric acid was added under ice-cooling to adjust pH to 8–9. The reaction mixture was saturated by the addition of sodium chloride, then extracted with chloroform and dried over anhydrous magnesium sulfate. The solvent was evaporated under reduced pressure to give 1.488 g of the title compound as a clear pale yellow oily product (yield, 68.0%), which was used for the next reaction without purification.

(c) 6-t-butoxycarbonyl-4,5,6,7-tetrahydrothiazolo[5,4-c]pyridine

To the solution of the compound prepared in Referential Example 20 (b) (1.458 g, 10.4 mmole) in DMF (50 ml) were added triethylamine (2.2 ml, 15.8 mmole) and di-t-butyl dicarbonate (2.5 ml, 10.9 mmole) at room temperature. After the mixture was stirred at room temperature for 5 hours, 1N HCl was added under ice-cooling. The mixture was extracted with ethyl acetate, washed with saturated sodium hydrogen carbonate and brine in this sequence, dried over anhydrous magnesium sulfate. The solvent was evaporated under reduced pressure to give 2.585 g of a crude product. The product was purified by column chromatography on silica gel (C-200=100 g, hexane:ethyl acetate=10:1–5:1) to give 1.493 g of the title compound as a pale yellow crystal (yield, 59.7%).

$^1$H-NMR (CDCl$_3$) δ: 1.49 (s, 9H), 2.84–3.03 (m, 2H), 3.66–3.85 (m, 2H), 4.68 (s, 2H), 8.68 (s, 1H). EIMS (m/z): 240 (M$^+$).

(d) 6-t-butoxycarbonyl-4,5,6,7-tetrahydrothiazolo[5,4-c]pyridin-2-carboxylic acid To the solution of the compound prepared in Referential Example 20 (c) (721.0 mg, 3.0 mmole) in THF (50 ml) was added dropwise a 1.6M solution of n-butyl lithium in hexane (2.44 ml, 3.9 mmole) at −78° C. under argon. After stirring the mixture for 5 minutes, carbon dioxide was blown into the reaction mixture at −78° C. After water and ether were added and the mixture was extracted with 5N sodium hydroxide, the mixture was acidified with concentrated hydrochloric acid to pH 4. The mixture was further extracted with chloroform, washed with brine and dried over anhydrous magnesium sulfate. The solvents were evaporated under reduced pressure to give 434.3 mg of the title compound as a brown crystal (yield, 50.9%).

$^1$H-NMR (CDCl$_3$) δ: 1.50 (s, 9H), 2.90–3.05 (m, 2H), 3.69–3.87 (m, 2H), 4.75 (s, 2H).

Example 48

[[4-[[[(4,5,6,7-tetrahydrothiazolo[5,4-c]pyridin-2-yl)-carbonyl]amino]-1-hydroxyethyl]-o-phenylene]dioxy]diacetic acid trifluoroacetate (a) Di-t-butyl [[4-[[[(6-t-butoxycarbonyl-4,5,6,7-tetrahydrothiazolo[5,4-c]pyridin-2-yl)carbonyl]amino]-1-hydroxyethyl]-o-phenylene]dioxy]diacetate To a flask in which the compound prepared in Referential Example 20 (d) (137.9 mg, 0.485 mmole) and di-t-butyl [4-(2-amino-1-hydroxyethyl)-o-phenylene]dioxy]diacetate (209.5 mg, 0.485 mmole) were placed was added a solution of HOBT (72.2 mg, 0.534 mmole) in DMF (4.8 ml). Triethylamine (75 ml, 0.538 mmole) and 1-ethyl-3-(3'-dimethylaminopropyl)carbodiimide (WSCI) (102.4 mg, 0.534 mmole) were added under ice-cooling to the flask. The mixture was stirred for 10 minutes and then heated up to room temperature. After stirring for 4.5 hours, HOBT (72.2 mg, 0.534 mmole) and WSCI (102.4 mg, 0.534 mmole) were added. The mixture was then stirred at room temperature for 20.5 hours. After water was added to the reaction mixture, the resulting mixture was extracted with ethyl acetate, washed with brine and dried over anhydrous magnesium sulfate. The solvent was evaporated under reduced pressure to give 398.2 mg of a crude product, which was purified thrice by column chromatography on silica gel with an eluent system of CHCl$_3$: MeOH=50:1–150:1 to give 152.6 mg of the title compound as a pale yellow crystal (yield, 47.4%).

$^1$H-NMR (CDCl$_3$) δ: 1.44–1.54 (m, 27H), 2.82–2.92 (m, 2H), 3.41–3.52 (m, 2H), 3.68–3.86 (m, 3H), 4.59 (s, 2H), 4.60 (s, 2H), 4.69 (s, 2H), 4.83–4.89 (m, 1H), 6.83 (d, J=8.72 Hz, 1H), 6.91–6.97 (m, 2H). EIMS (m/z): 663 (M$^+$).

(b) To the solution of the compound prepared in (a) (115.3 mg, 0.174 mmole) in anisole (0.5 ml) was added trifluoroacetic acid (2.0 ml) at 0° C. Crystals were deposited by the addition of isopropyl ether at 0° C., collected by filtration, and lyophilized to give 82.1 mg of a crude product, which was purified on a LH column (50% methanol) to give 76.6 mg of the title compound as a colorless crystal (yield, 77.8%).

$^1$H-NMR (DMSO-d$_6$) δ: 2.86–3.06 (m, 2H), 3.40–3.89 (m, 5H), 4.25–4.50 (m, 2H), 4.55–4.70 (m, 4H), 6.68–6.98 (m, 3H).

Referential Example 23 t-Butyl [4-(aminoacetyl)-2-propyoxy]phenoxyacetate hydrochloride (a) t-Buty[4-(azidoacetyl)-2-allyloxy]phenoxyacetate To the solution of the compound prepared in Referential Example 19 (b) (500 mg, 1.63 mmole) in acetone (7 ml) were added potassium carbonate (270 mg) and allyl iodide (0.5 ml), and the mixture was stirred at room temperature for 25 hours. The reaction mixture was diluted with ethyl acetate, washed with water and dried over anhydrous magnesium sulfate. After the inorganic salt was removed by filtration, the filtrate was concentrated under reduced pressure. The oily product thus obtained was purified by column chromatography on silica gel with an eluent system of chloroform:ethyl acetate=20:1 to give 500 mg of the title compound as a pale yellow crystal (yield, 88%).

$^1$H-NMR (CDCl$_3$) δ: 1.48 (s, 9H), 4.50 (s, 2H), 4.67 (s, 2H), 4.68–4.70 (m, 2H), 5.30–5.35 (m, 1H), 5.42–5.50 (m, 1H), 6.04–6.13 (m, 1H), 6.49 (d, J=8.21 Hz, 1H), 7.47 (dd, J=2.06, 8.21 Hz, 1H), 7.53 (d, J=2.06 Hz, 1H). EIMS (m/z): 347 (M$^+$).

(b) Starting from 485 mg (1.40 mmole) of the compound prepared in (a), the title compound was prepared as a pale yellow oily product (474 mg; yield, 94%) according to the method described in Referential Example 9 (b).

$^1$H-NMR (CD$_3$OD) δ: 1.08 (t, J=7.49 Hz, 3H), 1.49 (s, 9H), 1.86 (m, J=7.49 Hz, 2H), 4.06 (t, J=7.49 Hz, 2H), 4.52 (s, 2H), 4.74 (s, 2H), 6.97 (d, J=8.32 Hz, 1H), 7.58 (d, J=2.22 Hz, 1H), 7.62 (dd, J=2.22 Hz, 8.32 Hz, 1H). EIMS (m/z): 323 (M$^+$).

Example 49

4-[[(4,5,6,7-tetrahydrothieno[3,2-c]pyridin-2-yl)-carbonyl]aminoacetyl]-2-propyloxyphenoxyacetic acid trifluoroacetate (a) t-Butyl 4-[[5-t-butoxycarbonyl-4,5,6,7-tetrahydrothieno[3,2-c]pyridin-2-yl)carbonyl]-aminoacetyl]-2-propyloxyphenoxyacetate Starting from 355 mg (1.25 mmole) of the compound prepared in Referential Example 1 and 450mg of the compound prepared in Referential Example 26, the title compound was prepared as a yellow foam product (580 mg; yield, 79%) according to the method described in Example 9 (a).

$^1$H-NMR (CDCl$_3$) δ: 1.08 (t, J=7.49 Hz, 3H), 1.48 (s, 9H), 1.50 (s, 9H), 1.90 (m, J=7.49 Hz, 2H), 2.88 (brs, 2H), 3.74 (brs, 2H), 4.06 (t, J=7.49 Hz, 2H), 4.51 (brs, 2H), 4.67 (s, 2H), 6.82 (d, J=8.60 Hz, 1H), 7.04 (brs, 1H), 7.33 (s, 1H), 7.55 (d, J=2.22 Hz, 1H), 7.60 (dd, J=2.22 Hz, 8.60 Hz, 1H). EIMS (m/z): 588 (M$^+$)

(b) Starting from 500 mg (0.849 mmole) of the compound prepared in (a), the title compound was prepared as a pale yellow foam product (389 mg; yield, 84%) according to the method described in Example 9 (b).

$^1$H-NMR (CD$_3$OD) δ: 1.09 (t, J=7.21 Hz, 3H), 1.87 (m, J=7.21 Hz, 2H), 3.21 (t, J=6.10 Hz, 2H), 3.58 (t, J=6.10 Hz, 2H), 4.06 (t, J=7.21 Hz, 2H), 4.32 (brs, 2H), 4.80 (s, 2H), 4.82 (s, 2H), 7.00 (d, J=8.60 Hz, 1H), 7.54 (s, 1H), 7.59 (s, 1H), 7.68 (d, J=8.60 Hz, 1H). FDMS (m/z): 433 (M$^+$+1).

Referential Example 24 t-Butyl [4-(aminoacetyl)-2-hydroxy]phenoxyacetate hydrochloride

Starting from 500 mg (1.63 mmole) of the compound prepared in Referential Example 19 (b), the title compound was prepared as a pale yellow powder (456 mg; yield, 88%) according to the method described in Example 9 (b).

$^1$H-NMR (CD$_3$OD) δ: 1.51 (s, 9H), 4.88 (s, 2H), 4.76 (s, 2H), 6.97 (d, J=8.60 Hz, 1H), 7.48 (d, J=2.22 Hz, 1H), 7.52 (dd, J=2.22 Hz, 8.60 Hz, 1H). SIMS (m/z): 282 (M$^+$+1).

Example 50

4-[[(4,5,6,7-tetrahydrothieno[3,2-c]pyridin-2-yl)-carbonyl]aminoacetyl]-2-benzyloxyphenoxyacetic acid trifluoroacetate (a) t-butyl 4-[[(5-t-butoxycarbonyl-4,5,6,7-tetrahydrothieno[3,2-c]pyridin-2-yl)carbonyl]aminoacetyl]-2-hydroxyphenoxyacetate Starting from 1.6 g (5.66 mmole) of the compound prepared in Referential Example 1 and 1.8 g of compound prepared in Referential Example 28, the title compound was prepared as a yellow oily product (2.8 g; yield, 93%) according to the method described in Example 9 (a).

$^1$H-NMR (CDCl$_3$) δ: 1.50 (s, 9H), 1.51 (s, 9H), 2.88 (brs, 2H), 3.74 (brs, 2H), 4.50 (brs, 2H), 4.63 (s, 2H), 4.84 (d, J=4.17 Hz, 2H), 6.91 (d, J=8.60 Hz, 1H), 7.02 (brs, 1H), 7.33 (s, 1H), 7.54 (dd, J=2.22 Hz, 8.60 Hz, 1H), 7.62 (d, J=2.22 Hz, 1H).

(b) t-butyl 4-[[(5-t-butoxycarbonyl-4,5,6,7-tetrahydrothieno[3,2-c]pyridin-2-yl) carbonyl]aminoacetyl]-2-benzyloxy phenoxyacetate To the solution of the compound prepared in (a) (100 mg, 0.183 mmole) in DMF (3 ml) were added potassium carbonate (30 mg ) and benzyl bromide (50 μl ), and the mixture was stirred at room temperature for 2 hours. The reaction mixture was diluted with ethyl acetate, washed with water and dried over anhydrous magnesium sulfate. After the inorganic salt was removed by filtration, the filtrate was concentrated under reduced pressure. The oily product thus obtained was purified by column chromatography on silica gel with an eluent system of chloroform:ethyl acetate=10:1 to give 54 mg of the title compound as a pale yellow oily product (yield, 46%).

$^1$H-NMR (CDCl$_3$) δ: 1.49 (s, 9H), 1.50 (s, 9H), 2.87 (brs, 2H), 3.74 (brs, 2H), 4.50 (s, 2H), 4.69 (s, 2H), 4.81 (d, J=4.10 Hz, 2H), 5.23 (s, 2H), 6.84 (d, J=8.97 Hz, 1H), 7.00 (brs, 1H), 7.30–7.63 (m, 8H). FDMS (m/z ): 637 (M$^+$+1).

(c) Starting from 54 mg of the compound prepared in (b), the title compound was prepared as a pale yellow powder (30 mg; yield, 60%) according to the method described in Example 9 (b).

$^1$H-NMR (CD$_3$OD) δ: 3.29 (brs, 2H), 3.68 (brs, 2H), 4.40 (brs, 2H), 4.86 (s, 2H), 4.91 (s, 2H), 5.30 (s, 2H), 7.11 (d, J=8.46 Hz, 1H), 7.40–7.62 (m, 6H), 7.74 (d, J=2.05 Hz, 1H), 7.78 (dd, J=2.05 Hz, 8.46 Hz, 1H). EDMS (m/z): 481 (M$^+$+1).

Referential Example 25 t-butyl [4-(aminoacetyl)-2-(ethoxycarbonylmethyloxy)]-phenoxyacetate hydrochloride (a) t-butyl [4-(azidoacetyl)-2-(ethoxycarbonylmethyloxy)]phenoxyacetate To the solution of the compound prepared in Referential Example 19 (b) (500 mg, 1.63 mmole) in acetone (5 ml) were added potassium carbonate (270 mg) and ethyl bromoacetate (0.2 ml), and the mixture was stirred at room temperature for 6 hours. The reaction mixture was diluted with ethyl acetate, washed with water and dried over anhydrous magnesium sulfate. After the inorganic salt was removed by filtration, the filtrate was concentrated under reduced pressure. The oily product thus obtained was purified by column chromatography on silica gel with an eluent system of chloroform:ethyl acetate=20:1 to give the title compound as a pale yellow crystal (552 mg, yield, 86%).

$^1$H-NMR (CDCl$_3$) δ: 1.31 (t, J=7.21 Hz, 3H), 1.48 (s, 9H), 4.27 (q, J=7.21 Hz, 2H), 4.49 (s, 2H), 4.68 (s, 2H), 4.77 (s, 2H), 6.83 (d, J=9.15 Hz, 1H), 7.49–7.51 (m, 2H). FDMS (m/z): 393 (M$^+$).

(b) Starting from 200 mg (0.508 mmole) of the compound prepared in (a), the title compound was prepared as a pale yellow powder (183 mg; yield, 89%) according to the method described in Example 9 (b).

$^1$H-NMR (CD$_3$OD) δ: 1.38 (t, J=7.21 Hz, 3H), 4.34 (q, J=7.21 Hz, 2H), 4.62 (s, 2H), 4.89 (s, 2H), 4.93 (s, 2H), 7.14 (d, J=8.60 Hz, 1H), 7.70 (d, J=2.22 Hz, 1H), 7.80 (dd, J=2.22 Hz, 8.60 Hz, 1H). SIMS (m/z): 368 (M$^+$+1).

Example 51

4-[[(4,5,6,7-tetrahydrothieno[3,2-c]pyridin-2-yl)-carbonyl]aminoacetyl]-2-(ethoxycarbonylmethyloxy)-phenoxyacetic acid trifluoroacetate (a) t-butyl 4-[[(5-t-butoxycarbonyl-4,5,6,7-tetrahydrothieno[3,2-c]pyridine-2-yl)-carbonyl]aminoacetyl]-2-(ethoxycarbonylmethyloxy)phenoxyacetate Starting from 130 mg (0.448 mmole) of the compound prepared in Referential Example 1 and 180 mg of the compound prepared in Referential Example 25 (b), the title compound was prepared as a pale yellow foam product (145 mg; yield, 51%) according to the method described in Example 9 (a).

$^1$H-NMR (CDCl$_3$) δ: 1.32 (t, J=7.21 Hz, 3H), 2.86 (brs, 2H), 3.73 (brs, 2H), 4.28 (q, J=7.21 Hz, 2H), 4.50 (brs, 2H), 4.70 (s, 2H), 4.78 (s, 2H), 4.84 (d, J=4.16 Hz, 2H), 6.85 (d, J=8.60 Hz, 1H), 7.32 (s, 1H), 7.55 (d, J=1.94 Hz, 1H), 7.65 (dd, J=1.94 Hz, 8.60 Hz, 1H).

(b) Starting from 140 mg (0.221 mmole) of the compound prepared in (a), the title compound was prepared as a colorless solid product (78 mg; yield, 60%) according to the method described in Example 9 (b).

$^1$H-NMR (CD$_3$OD) δ: 1.38 (t, J=7.21 Hz, 3H), 3.30 (brs, 2H), 3.67 (brs, 2H), 4.34 (q, J=7.21 Hz, 2H), 4.41 (s, 2H), 4.89 (s, 2H), 4.94 (s, 2H), 7.15 (d, J=8.60 Hz, 1H), 7.63 (s, 1H), 7.69 (d, J=2.22 Hz, 1H), 7.84 (dd, J=2.22 Hz, 8.60 Hz, 1H).

Example 52

4-[(4,5,6,7-tetrahydrothieno[3,2-c]pyridin-2-yl)-carbonylamino]phenoxyacetic acid The title compound was prepared according to the method described in Example 9.

$^1$H-NMR (DMSO-d$_6$) δ: 3.10 (s, 2H), 3.47 (s, 2H), 4.25 (s, 2H), 4.64 (s, 2H), 6.90 (d, J=8.8 Hz, 2H), 7.60 (d, J=8.8 Hz, 2H).

Example 53

4-[[(4,5,6,7-tetrahydrothieno[3,2-c]pyridin-2-yl)-carbonyl]aminoacetyl]-2-hydroxyphenoxyacetic acid trifluoroacetate Starting from the compound prepared in Example 50 (a) (100 mg, 0.183 mmole), the title compound (55 mg, yield 60%) was prepared as a pale orange solid product according to the method described in Example 9 (b).

$^1$H-NMR (CD$_3$OD) δ: 3.30 (t, J=6.10 Hz, 2H), 3.67 (t, J=6.10 Hz, 2H), 4.42 (brs, 2H), 4.90 (d, J=5.00 Hz, 2H), 4.99 (s, 2H), 7.29 (d, J=8.60 Hz, 1H), 7.66 (s, 1H), 7.89 (d, J=1.94 Hz, 1H), 7.95 (dd, J=1.94 Hz, 8.60 Hz, 1H).

Example 54

4-[[(4,5,6,7-tetrahydrothieno[3,2-c]pyridin-2-yl)-carbonyl]aminoacetyl]-2-(N-ethyl-carbamoyloxy)-phenoxyacetic acid trifluoroacetate (a) t-butyl 4-[[(5-t-butoxycarbonyl-4,5,6,7-tetrahydrothieno[3,2-c]pyridin-2-yl)-carbonyl]aminoacetyl]-2-(N-ethylcarbamoyloxy)phenoxyacetate To the solution of the compound prepared in Example 50 (a) (280 mg, 0.512 mmole) in DMF were added triethylamine (0.1 ml) and ethyl isocyanate (50 μl), and the mixture was stirred at room temperature for 4 hours. To the reaction solution was added water, and the mixture was acidified with 1N hydrochloric acid. The solution was extracted with ethyl acetate and dried over anhydrous magnesium sulfate. After the inorganic salt was removed by filtration, the filtrate was concentrated under reduced pressure. The oily product thus obtained was purified by column chromatography on silica gel with an eluent system of chloroform:methanol=100:1 to give 175 mg of the title compound as a pale yellow foam product (yield, 55%).

$^1$H-NMR (CDCl$_3$) δ: 1.24 (t, J=7.1 Hz, 3H), 1.48 (s, 9H), 1.49 (s, 9H), 2.88 (brs, 2H), 3.33 (m, 2H), 3.73 (brs, 2H), 4.50 (brs, 2H), 4.62 (s, 2H), 4.84 (d, J=4.11 Hz, 2H), 5.27 (brs, 1H), 6.89 (d, J=8.72 Hz, 1H), 7.04 (brs, 1H), 7.33 (s, 1H), 7.81 (s, 1H), 7.85 (d, J=8.72 Hz, 1H). FDMS (m/z): 617 (M$^+$).

(b) Starting from 50 mg (0.0809 mmole) of the compound prepared in (a), the title compound was prepared as a colorless solid product (10 mg, yield, 21%) according to the method described in Example 9 (b).

$^1$H-NMR (CD$_3$OD) δ: 1.28 (t, J=7.21 Hz, 3H), 3.27–3.34 (m, 4H), 3.67 (t, J=6.38 Hz, 2H), 4.41 (brs, 2H), 4.88 (s, 2H), 4.89 (s, 2H), 7.21 (d, J=8.88 Hz, 1H), 7.63 (s, 1H), 7.87 (d, J=1.94 Hz, 1H), 8.02 (dd, J=1.94 Hz, 8.88 Hz, 1H).

Referential Example 26

2-aminoacetyl-4,5-di(t-butoxycarbonylmethyl)oxypyridine bishydrochloride (a) 5-benzyloxy-2-hydroxymethyl-4-oxo-4H-pyran To the solution of kojic acid (28 g) in DMF (200 ml) was added potassium carbonate (32 g), and the mixture was stirred at room temperature for 30 minutes. After benzyl chloride (25 g) was added, the mixture was further stirred for 60 minutes. The solvent was evaporated. The residue was then extracted with ethyl acetate, washed with water and dried. After the solvent was evaporated, the residue was crystallized from ethyl acetate to give 5-benzyloxy-2-hydroxymethyl-4-oxo-4H-pyran (34.6 g).

$^1$H-NMR (CD$_3$OD) δ: 4.40 (s, 2H), 5.02 (s, 2H), 6.51 (s, 1H), 7.32–7.44 (m, 5H), 8.00 (s, 1H).

(b) 5-benzyloxy-4-hydroxy-2-hydroxymethylpyridine

To the solution of the compound prepared in Referential Example 26 (a) (11 g) in methanol (20 ml) was added 25% aqueous ammonia (100 ml), and the mixture was stirred in a sealed tube at 100° C. for 16 hours. The solvent was evaporated, and the residue was crystallized from warmed methanol to give 5-benzyloxy-4-hydroxy-2-hydroxymethylpyridine (10 g).

$^1$H-NMR (CD$_3$OD) δ: 4.51 (s, 2H), 5.09 (s, 2H), 6.43 (s, 1H), 7.29–7.45 (m, 6H).

(c) 5-benzyloxy-4-(t-butoxycarbonylmethyl)oxy-2-hydroxymethylpyridine

To the solution of the compound prepared in Referential Example 26 (b) (5 g) in DMF (500 ml) were added potassium carbonate (3 g) and t-butyl bromoacetate (3.5 ml), and the mixture was stirred at room temperature for 4 hours. The reaction mixture was extracted with ethyl acetate, washed with water and dried. After the solvent was evaporated, the residue was placed on a silica gel column and eluted with ethyl acetate:n-hexane=1:1 to give 5-benzyloxy-4-(t-butoxycarbonylmethyl)oxy-2-hydroxymethylpyridine (4.2 g).

$^1$H-NMR (CDCl$_3$) δ: 1.47 (s, 9H), 4.61 (s, 2H), 4.65 (s, 2H), 5.17 (s, 2H), 6.75 (s, 1H), 7.30–7.45 (m, 5H), 8.06 (s, 1H).

(d) 4-(t-butoxycarbonylmethyl)oxy-5-hydroxy-2-hydroxymethylpyridine

To the solution of the compound prepared in Referential Example 26 (c) (20 g) in methanol (200 ml) was added 10% palladium-carbon (1 g) to carry out catalytic hydrogenation (75 minutes). After the reaction mixture was filtered, the filtrate was concentrated to give 4-(t-butoxycarbonylmethyl)oxy-5-hydroxy-2-hydroxymethylpyridine (12.4 g).

$^1$H-NMR (CDCl$_3$) δ: 1.50 (s, 9H), 4.58 (s, 2H), 4.63 (s, 2H), 6.75 (s, 1H), 8.10 (s, 1H).

(e) 4,5-di-(t-butoxycarbonylmethyl)oxy-2-hydroxymethylpyridine

To the solution of the compound prepared in Referential Example 26 (d)(3 g) in DMF (30 ml) was added 60% NaH (0.47 g), and the mixture was stirred at room temperature for 1 hour. Then, reaction mixture was added dropwise the solution of t-butyl bromoacetate (1.73 ml) in DMF (30 ml) over a period of 5 hours. The mixture was further stirred for 2 hours. After the solvent was evaporated, the residue was extracted with ethyl acetate, washed with water and dried, and the solvent was evaporated. The residue was placed on a silica gel column and eluted with ethyl acetate:n-hexane=3:1 to give 4,5-di(t-butoxycarbonylmethyloxy)-2-hydroxymethylpyridine (3.1 g).

¹H-NMR (CDCl₃) δ: 1.48 (s, 9H), 1.49 (s, 9H), 4.63 (s, 2H), 4.64 (s, 2H), 4.65 (s, 2H), 6.67 (s, 1H), 8.11 (s, 1H).

(f) 4,5-di(t-butoxycarbonylmethyl)oxy-2-formylpyridine

To the solution of the compound prepared in Referential Example 26 (e) (6 g) in dichloromethane (80 ml) was added manganese dioxide (10 g), and the mixture was stirred at room temperature for 16 hours. The reaction mixture was filtered, and the filtrate was concentrated by evaporation. The residue was placed on a silica gel column and eluted with ethyl acetate:n-hexane=1:1 to give 4,5-di(t-butoxycarbonylmethyl)oxy-2-formylpyridine (4.6 g).

¹H-NMR (CDCl₃) δ: 1.49 (s, 18H), 4.71 (s, 2H), 7.38 (s, 1H), 8.24 (s, 1H), 9.91 (s, 1H).

(g) 4,5-di-(t-butoxycarbonylmethyloxy)-2-(1-hydroxy)ethylpyridine

To the solution of the compound prepared in Referential Example 26 (f) (4.6 g) in THF (50 ml) was added methyl magnesium bromide (1.02 mole/liter in THF, 17.9 ml) at −40° C., and the mixture was stirred for 30 minutes. Water was added to the reaction mixture. The resulting mixture was extracted with ethyl acetate, washed with water and dried. After the solvent was removed by evaporation, the residue was placed on a silica gel column and eluted with ethyl acetate:n-hexane=2:1 to give 4,5-di(t-butoxycarbonylmethyloxy)-2-(1-hydroxy)ethylpyridine (2.82 g).

¹H-NMR (CDCl₃) δ: 1.48 (m, 21H), 4.63 (s, 2H), 4.66 (m, 2H), 4.78 (m, 1H), 6.68 (s, 1H), 8.08 (s, 1H).

(h) 2-acetyl-4,5-di-(t-butoxycarbonylmethyloxy)pyridine

To the solution of the compound prepared in Referential Example 26 (g) (2.8 g) in dichloromethane (30 ml) was added manganese dioxide (6.3 g), and the mixture was stirred at room temperature for 16 hours. The reaction mixture was filtered, and the filtrate was concentrated to give 2-acetyl-4,5-di-(t-butoxycarbonylmethyloxy)pyridine (2.58

¹H-NMR (CDCl₃) δ: 1.49 (m, 18H), 2.66 (s, 3H), 4.70 (s, 2H), 4.74 (s, 2H), 7.50 (s, 1H), 8.14 (s, 1H).

(i) 2-bromoacetyl-4,5-di(t-butoxycarbonylmethyl)oxypyridine

To the solution of the compound prepared in Referential Example 26 (h) (1.0 g) in dichloroethane (10 ml) were added triethylamine (0.9 ml) and trimethylsilyltrifluoromethane sulfonate (0.54 ml), and the mixture was stirred at −40° C. for 30 minutes. After N-bromosuccinimide (0.49 g) was added, the mixture was stirred at −35° C. for 30 minutes. The reaction mixture was concentrated, extracted with ether, washed with aqueous sodium hydrogen carbonate and water and dried. The solvent was removed by evaporation. The residue was placed on a silica gel column and eluted with ethyl acetate:n-hexane=1:3 to give 2-bromoacetyl-4,5-di-(t-butoxycarbonylmethyloxy)pyridine (561 mg).

¹H-NMR (CDCl₃) δ: 1.49 (s, 18H), 4.70 (s, 2H), 4.75 (s, 2H), 4.81 (s, 2H), 7.52 (s, 1H), 8.13 (s, 1H).

(j) 2-azidoacetyl-4,5-di(t-butoxycarbonylmethyloxy)pyridine

To the solution of the compound prepared in Referential Example 26 (i) (550 mg) in DMF (15 ml) was added sodium azide (85 mg), and the mixture was stirred at room temperature for 30 minutes. The reaction mixture was concentrated. The residue was extracted with ethyl acetate, washed with water, dried, and the solvent was removed by evaporation. The residue was placed on a silica gel column and eluted with ethyl acetate:n-hexane=1:3 to give 2-azidoacetyl-4,5-di-(t-butoxycarbonylmethyloxy) pyridine (442 mg).

¹H-NMR (CDCl₃) δ: 1.49 (s, 9H), 1.50 (s, 9H), 4.70 (s, 2H), 4.74 (s, 2H), 4.80 (s, 2H), 7.50 (s, 1H), 8.10 (s, 1H).

(k) 2-aminoacetyl-4,5-di(t-butoxycarbonylmethyloxy)pyridine bishydrochloride

To the solution of the compound prepared in Referential Example 26 (j) (100 mg) in methanol (8 ml)—CHCl₃ (2 ml) were added 10% palladium-carbon (10 mg) and 1N hydrochloric acid (0.5 ml), and catalytic hydrogenation was conducted for 3 hours. The reaction mixture was filtered. After the filtrate was concentrated, water was added to the concentrate. The mixture was lyophilized to give 2-aminoacetyl-4,5-di-(t-butoxycarbonylmethyloxy)pyridine bishydrochloride (104 mg).

¹H-NMR (CD₃OD) δ: 1.49 (s, 9H), 1.49 (s, 9H), 7.63 (s, 1H), 8.27 (s, 1H).

Example 55

2-[2-[(4,5,6,7-tetrahydrothieno[3,2-c]pyridin-2-yl)-carbonyl]aminoacetyl]pyridinyl-4,5-dioxydiacetic acid bistrichloroacetate (a) To the solution of the compound prepared in Referential Example 40 (42 mg) in DMF (1 ml) were added BOP (66 mg) and N-methylmorpholine (0.05 ml), and the mixture was stirred at room temperature for 1 hour. Then, 5-t-butoxycarbonyl-4,5,6,7-tetrahydrothieno[3,2-c]pyridin-2-ylcarboxylic acid (70 mg) was added. The mixture was further stirred for 4 hours. The reaction mixture was extracted with ethyl acetate, washed with water, dried. After the solvent was removed by evaporation, the residue was placed on a silica gel column and eluted with ethyl acetate:n-hexane=1:2 to give di-t-butyl-2-[2-[(5-t-butoxycarbonyl-4,5,6,7-tetrahydrothieno[3,2-c]pyridin-2-yl)carbonyl]aminoacetyl]pyridinyl-4,5-dioxydiacetate (46 mg). ¹H-NMR (CDCl₃) δ: 1.49 (s, 9H), 1.50 (s, 9H), 2.87 (brs, 2H), 3.73 (brs, 2H), 4.50 (s, 2H), 4.71 (s, 2H), 4.76 (s, 2H), 5.07 (d, 2H), 6.82 (brs, 1H), 7.31 (s, 1H), 7.50 (s, 1H), 8.15 (s, 1H).

(b) To the solution of the compound prepared in (a) (44 mg) in anisole (0.06 ml) was added trifluoroacetic acid (0.3 ml), and the mixture was stirred at room temperature for 30 minutes. After diisopropyl ether was added to the mixture, crystals deposited were collected by filtration and washed with diethyl ether to give the title compound (30 mg).

¹H-NMR (DMSO-d₆) δ: 3.04 (s, 2H), 4.19 (s, 2H), 4.82–4.93 (m, 6H), 7.41 (s, 1H), 7.59 (s, 1H), 8.23 (s, 1H).

Example 56

Di-n-butyl [[4-[[[(4,5,6,7-tetrahydrothieno[3,2-c]pyridin-2-yl)carbonyl]amino]acetyl]-o-phenylene]dioxy]diacetate trifluoroacetate (a) To the solution of the compound prepared in Referential Example 1 (392 mg, 1.64 mmole) in DMF (10 ml) were added BOP (800 mg, 1.81 mmole), N-methylmorpholine (0.40 ml, 3.62 mmole) and di-n-butyl[[4-(aminoacetyl)-o-phenylene]dioxy]diacetate (710 mg, 164 mmole), and the mixture was stirred at room temperature for 1.5 hours. The reaction mixture was poured onto ice-water, extracted with ethyl acetate and then washed with water. After the ethyl acetate layer was dried over anhydrous magnesium sulfate, the ethyl acetate was removed by evaporation. The residue was purified by column chromatography on silica gel with an eluent system of hexane:ethyl acetate=3:1→1:1 to give 500 mg of di-n-butyl [[4-[[2-[(5-t-butoxycarbonyl-4,5,6,7-tetrahydrothieno[3,2-c]pyridin-2-yl)carbonyl]amino]acetyl]-o-phenylene]dioxy]diacetate (yield, 45%).

¹H-NMR (CDCl₃) δ: 0.92 (t, J=7 Hz, 3H), 0.92 (t, J=7 Hz, 3H), 1.36 (m, 4H), 1.50 (s, 9H), 1.63 (m, 4H), 2.87 (s, 2H), 3.74 (s, 2H), 4.22 (t, J=7 Hz, 2H), 4.22 (t, J=7 Hz, 2H), 4.50

(s, 2H), 4.79 (s, 2H), 4.81 (s, 2H), 4.84 (d, J=4 Hz, 2H), 6.89 (d, J=8 Hz, 1H), 7.00 (m, 1H), 7.33 (s, 1H), 7.55 (d, J=2 Hz, 1H), 7.65 (dd, J=2.8 Hz, 1H). EIMS (m/z): 660 (M$^+$).

(b) To the compound prepared in (a) (470 mg, 0.711 mmole) were added anisole (0.7 ml) and trifluoroacetic acid (2.4 ml), and the mixture was stirred at room temperature for 1 hour. After the solvent was removed by evaporation, the residue was extracted with water and washed with ether. The aqueous layer was combined and lyophilized to give 344 mg of the title compound as a colorless crystal (yield, 72%).

$^1$H-NMR (CD$_3$D) δ: 0.92 (t, J=7 Hz, 3H), 0.93 (t, J=7 Hz, 3H), 1.37 (m, 4H), 1.63 (m, 4H), 3.20 (t, J=6 Hz, 2H), 3.58 (t, J=6 Hz, 2H), 4.20 (t, J=6 Hz, 2H), 4.21 (t, J=6 Hz, 2H), 4.32 (s, 2H), 4.79 (s, 2H), 4.83 (s, 2H), 4.89 (s, 2H), 7.05 (d, J=8 Hz, 1H), 7.54 (s, 1H), 7.60 (d, J=2 Hz, 1H), 7.74 (dd, J=2, 8 Hz, 1H). EIMS (m/z ): 560 (M$^+$).

Example 57

Dicyclohexyl [[4-[[[(4,5,6,7-tetrahydrothieno[3,2-c]pyridin-2-yl)-carbonyl]amino]acetyl]-o-phenylene]dioxy]diacetate Free derivative of the compound prepared in Example 34 (700 mg, 1.39 mmole) was stirred in the mixture of cyclohexanol (14 ml) and chloroform (7 ml) saturated with hydrochloric acid at room temperature overnight. After chloroform was added to the reaction mixture, the resulting mixture was neutralized with a sodium hydrogen carbonate aqueous. The chloroform layer was separated and dried with anhydrous magnesium sulfate. The solvent was removed by evaporation. Purification by column chromatography on silica gel (CHCl$_3$: MeOH=10:1→4:1) gave the title compound (531 mg, yield, 57%).

$^1$H-NMR (CDCl$_3$) δ: 1.20–1.95 (m, 20H), 2.84 (s, 2H), 3.17 (t, J=5 Hz, 2H), 3.93 (s, 2H), 4.76 (s, 2H), 4.79 (s, 2H), 4.84 (d, J=4 Hz, 2H), 4,90 (m, 2H), 6.88 (d, J=8 Hz, 1H), 6.98 (s, 1H), 7.29 (s, 1H), 7.54 (d, J=2 Hz, 1H), 7.63 (dd, J=2, 8 Hz, 1H). EIMS (m/z): 612 (M$^+$).

Referential Example 27

4-Cyanocyclohexylcarboxylic acid

To the solution of methyl 4-cyanocyclohexylcarboxylate (470 mg, 2.81 mmole) prepared according to the method described in J. Am. Chem. Soc., 82, 2547 (1960) in methanol (5 ml) was added 1N sodium hydroxide (2.8 ml) under ice-cooling, and the mixture was stirred overnight during which the temperature of the mixture was left rising up to room temperature. After the reaction mixture was concentrated, water was added. The resulting mixture was washed with ether and acidified with 5N hydrochloric acid. After extracted thrice with chloroform, the mixture was dried with anhydrous magnesium sulfate. After the inorganic salt was removed by filtration, the filtrate was concentrated under reduced pressure to give 362 mg of the title compound as a colorless crystal (yield, 84%).

$^1$H-NMR (CDCl$_3$) δ: 1.50–1.70 (m, 4H), 2.07–2.18 (m, 4H), 2.38–2.54 (m, 2H).

Example 58

[[4-[[[trans-4-amidinocyclohexyl]carbonyl-N-methylamino]acetyl]-o-phenylene]dioxy]diacetic acid trifluoroacetate (a) Di-t-butyl [[4-[[[trans-4-cyanocyclohexyl]carbonyl-N-methylamino] acetyl]-o-phenylene]dioxy]diacetate Starting from the compound prepared in Referential Example 1 (153 mg, 1 mmole) and 90 (410 mg), the title compound (325 mg, yield, 65%) was obtained according to the method described in Example 9 (a).

$^1$H-NMR (CDCl$_3$) δ: 1.47 (s, 9H), 1.48 (s, 9H), 1.58–1.68 (m, 4H), 1.90–2.00 (m, 2H), 2.20–2.26 (m, 2H), 2.45–2.55 (m, 1H), 2.65–2.72 (m, 1H), 3.11 (s, 3H), 4.63 (s, 2H), 4.67 (s, 2H), 4.74 (s, 2H), 6.80 (d, J=8.33 Hz, 1H), 7.46 (d, J=1.94 Hz, 1H), 7.55 (dd, J=1.94 Hz, 8.33 Hz, 1H). EIMS (m/z ): 544 (M$^+$).

(b) [[4-[[[trans-4-thiocarbamoylcyclohexyl]carbonyl-N-methylamino]acetyl]-o-phenylene]dioxy]diacetic acid Into the solution of the compound prepared in (a) (655 mg, 1.2 mmole) in the mixture of pyridine (15 ml) and triethylamine (1 ml) was streamed a hydrogen sulfide gas for 1 hour, and the mixture was stirred in a sealed tube at 50° C. for 5 hours. After the reaction mixture was cooled to room temperature, it was diluted with ethyl acetate, and washed twice with each of a 5% aqueous sodium hydrogen carbonate and a 1M potassium hydrogen sulfate solution. After the organic layer was dried over anhydrous magnesium sulfate, the inorganic salt was removed by filtration. The filtrate was concentrated under reduced pressure, and the oily product thus obtained was purified by column chromatography on silica gel with an eluent system of chloroform:methanol =50:1 to give 71 mg of the thioamide derivative as a yellow oily product (yield, 10%).

$^1$H-NMR (CDCl$_3$) δ: 1.48 (s, 9H), 1.49 (s, 9H), 1.58–1.65 (m, 4H), 1.72–1.82 (m, 2H), 1.92–2.00 (m, H), 2.54–2.61 (m, 1H), 2.69–2.78 (m, 1H), 3.13 (s, 3H), 4.64 (s, 2H), 4.68 (s, 2H), 4.75 (s, 2H), 6.83 (d, J=8.46 Hz, 1H), 7.47 (d, J=1.79 Hz, 1H), 7.58 (dd, J=1.79 Hz, 8.46 Hz, 1H). SIMS (m/z): 579 (M$^+$+1).

(c) [[4-[[[trans-4-(imino(methylthio)methyl) cyclohexyl] carbonyl-N-methylamino]acetyl]-o-phenylene]dioxy]diacetic acid To the solution of the compound prepared in (b) (70 mg, 0.121 mmole) in acetone (7 ml) was added methyl iodide (0.7 ml), and the mixture was heated at reflux temperature for 1 hour. After the reaction mixture was concentrated under reduced pressure, the oily product thus obtained was purified by column chromatography on silica gel with an eluent system of chloroform methanol=100:1 to give 69 mg of the iminothiomethyl derivative as a yellow oily product (yield, 97%).

$^1$H-NMR (CDCl$_3$) δ: 1.47 (s, 9H), 1.48 (s, 9H), 1.55–1.69 (m, 4H), 1.92–1.98 (m, 2H), 2.02–2.09 (m, 2H), 2.25 (s, 3H), 2.30–2.43 (m, 1H), 2.60–2.68 (m, 1H), 3.11 (s, 3H), 4.63 (s, 2H), 4.67 (s, 2H), 4.74 (s, 2H), 6.80 (d, J=8.32 Hz, 1H), 7.47 (d, J=1.94 Hz, 1H), 7.57 (dd, J=1.94 Hz, 8.32 Hz, 1H). SIMS (m/z): 593 (M$^+$+1).

(d) Di-t-butyl [[4-[[[trans-4-amidinocyclohexyl]carbonyl-N-methylamino]acetyl]-o-phenylene]dioxy]diacetate To the solution of the compound prepared in (c) (62 mg, 0,107 mmole) in methanol (3 ml) was added ammonium acetate, and the mixture was stirred at reflux temperature for 1.5 hours. The reaction mixture was concentrated under reduced pressure to give 56 mg of the amidine derivative as a pale yellow oily product (yield, 93%).

$^1$H-NMR (CD$_3$OD) δ: 1.48 (s, 9H), 1.49 (s, 9H), 1.53–1.72 (m, 4H), 1.90–1.98 (m, 2H), 2.00–2.06 (m, 2H), 2.45–2.53 (m, 1H), 2.82–2.88 (m, 1H), 2.94, 3.18 (2s, 3H), 4.69, 4,71 (s, 2H), 4.76, 4.78 (2s, 2H), 4.83, 4.91 (2s, 2H), 6.99, 7.10 (2d, J=8.46 Hz, 1H), 7.54, 7.58 (2d, J=2.05 Hz, 1H), 7.68, 7.70 (2dd, J=2.05 Hz, 8.46 Hz, 1H).

(e) To the solution of the compound prepared in (d) (50 mg, 0.089 mmole) in anisole was added trifluoroacetic acid under ice-cooling. The mixture was stirred for 5 hours, during which the temperature of the mixture was left rising up to room temperature. After isopropyl ether was added to the reaction mixture, solids deposited were collected to give 31 mg of the title compound as the colorless solid (yield, 62%).

$^1$H-NMR (CD$_3$OD) δ: 1.48–1.72 (m, 4H), 1.87–2.03 (m, 4H), 2.45–2.55 (m, 1H), 2.80–2.88 (m, 1H), 2.95, 3.18 (2s, 3H), 4.77, 4.80 (2s, 2H), 4.83 (s, 2H), 4.84 (s, 2H), 7.04, 7.08 (2d, J =8.72 Hz, 1H), 7.57, 7.62 (2d, J=1.80 Hz, 1H), 7.68, 7.74 (2dd, J=1.80 Hz, 8.72 Hz, 1H). FDMS(m/z): 450 (M$^+$+1)

TABLE 1

Structure: A—B—Y—[phenyl ring with X, R^±1, R^±2, R^±3, R^±4]

| Example | A— | —B—Y— | X | $R^{\pm 1}$ | $R^{\pm 2}$ | $R^{\pm 3}$ | $R^{\pm 4}$ |
|---|---|---|---|---|---|---|---|
| 1 | H$_2$NCH$_2$—(cyclohexyl)— | —CONHCH$_2$CO— | CH | —OCH$_2$COOH | —OCH$_2$COOH | H | H |
| 2 | CH$_3$NHCH$_2$—(cyclohexyl)— | ← | ← | ← | ← | ← | ← |
| 3 | H$_2$NCNHCH$_2$—(cyclohexyl)— (NH) | ← | ← | ← | ← | ← | ← |
| 4 | H$_2$NCH$_2$—(cyclohexyl)— | (oxazole ring N=C–O–C) | ← | ← | ← | ← | ← |
| 5 | CH$_3$CONHCH$_2$—(cyclohexyl)— | —CONHCH$_2$CO— | ← | —OCH$_2$COONa | —OCH$_2$COONa | ← | ← |
| 6 | HN=C(NH$_2$)—(phenyl)—CONHCH$_2$—(cyclohexyl)— | ← | ← | —OCH$_2$COOH | —OCH$_2$COOH | ← | ← |
| 7 | H$_2$NCH$_2$—(cyclohexyl)— | —CONHCH$_2$CH$_2$— | ← | —OCH$_2$COOH | —OCH$_2$COOH | ← | ← |

TABLE 1-continued
| Example | A— | —B—Y— | X | R#1 | R#2 | R#3 | R#4 |
|---|---|---|---|---|---|---|---|
| 8 | 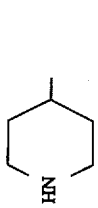 | —CONHCH₂CO— | CH | —OCH₂COOH | —OCH₂COOH | H | H |
| 9 |  | —CH₂CH₂CONCH₂CO—<br>       CH₃ | ↑ | ↑ | ↑ | ↑ | ↑ |
| 10 | ↑ | —CH₂CH₂CONHCH₂CO— | ↑ | ↑ | ↑ | ↑ | ↑ |
| 11 | ↑ | —CH₂CONCH₂CO— | ↑ | ↑ | ↑ | ↑ | ↑ |
| 12 | ↑ | —CH₂CH₂CH₂CONHCH₂CO— | ↑ | ↑ | ↑ | ↑ | ↑ |
| 13 |  | —CONHCH₂CO— | ↑ | ↑ | ↑ | ↑ | ↑ |
| 14 | 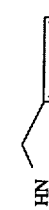 | —CONHCH₂CO— | ↑ | ↑ | ↑ | ↑ | ↑ |
| 15 | ↑ | —CH₂CH₂CONHCH₂CH₂— | ↑ | ↑ | ↑ | ↑ | ↑ |
| 16 | 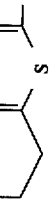 | —CONHCH₂— | ↑ | ↑ | ↑ | ↑ | ↑ |
| 17 |  | —CONHCH₂CO— | CH | —OCH₂COOH | —OCH₂COOH | H | H |

TABLE 1-continued

| Example | A— | —B—Y— | X | R^{t1} | R^{t2} | R^{t3} | R^{t4} |
|---|---|---|---|---|---|---|---|
| 18 | (thieno-piperidine) | —CONHCH₂CO— | ↑ | ↑ | ↑ | ↑ | ↑ |
| 19 | ↑ | —CONHCH₂CO—<br>\|<br>CH₃ | ↑ | ↑ | ↑ | ↑ | ↑ |
| 20 | ↑ | —CONHCH₂CO— | ↑ | —CH₂CH₂COOH | H | ↑ | ↑ |
| 21 | ↑ | —CONHCH₂CH—<br>\|<br>OH | N | —OCH₂COOH | ↑ | ↑ | ↑ |
| 22 | ↑ | —CONHCH₂CO— | CH | ↑ | ↑ | ↑ | ↑ |
| 23 | ↑ | ↑ | ↑ | H | —OCH₂COOH | ↑ | ↑ |
| 24 | ↑ | ↑ | ↑ | —OCH₂COOH | ↑ | ↑ | ↑ |
| 25 | ↑ | —CONHCH₂CO— | CH | ↑ | H | —OCH₂COOH | —OCH₂COOH |
| 26 | ↑ | ↑ | ↑ | ↑ | —OCH₂COOH | —OCH₃ | H |
| 27 | (methyl-thieno-piperidine) | ↑ | ↑ | ↑ | ↑ | H | ↑ |

TABLE 1-continued

| Example | A— | —B—Y— | X | R#1 | R#2 | R#3 | R#4 |
|---|---|---|---|---|---|---|---|
| 28 | [thiophene-fused azepine with CH₂—Ph] | ↑ | ↑ | ↑ | ↑ | ↑ | ↑ |
| 29 | [thiophene-fused azepine] | ↑ | ↑ | ↑ | ↑ | ↑ | ↑ |
| 30 | [thiophene-fused azepine] | ↑ | ↑ | ↑ | ↑ | ↑ | ↑ |
| 31 | [thiophene-fused azepine] | ↑ | ↑ | ↑ | ↑ | ↑ | ↑ |
| 32 | [thiophene-fused azepine] | —CO—CH₂NHCO— | CH | —OCH₂COOH | —OCH₂COOH | H | H |
| 33 | ↑ | —CONHCH₂CH₂— | ↑ | —OCH₂COOC₂H₅ | —OCH₂COOC₂H₅ | ↑ | ↑ |
| 34 | ↑ | —CONHCH₂CO— | ↑ | —OCH₂COOH | ↑ | ↑ | ↑ |
| 35 | [4-methylpiperidine, HN] | —CH₂CH₂CONHCH₂CO— | ↑ | —OCH₂COOH | —OCH₂COOH | ↑ | ↑ |

TABLE 1-continued

Structure: A—B—Y—[phenyl with R#1, R#2, R#3, R#4 and X]

| Example | A— | —B—Y— | X | R#1 | R#2 | R#3 | R#4 |
|---|---|---|---|---|---|---|---|
| 36 | 4-piperidinyl (HN-piperidine) | —CH₂CH₂CH₂CONHCH₂CO— | ← | ← | ← | ← | ← |
| 37 | ← | —CH₂CONHCH₂CO— with CH₃ branch | ← | ← | ← | ← | ← |
| 38 | ← | —CH₂CH₂CONHCH₂CO— | ← | —CH₂CH₂COOH | H | ← | ← |
| 39 | ← | —CONHCH₂CH₂— | ← | —OCH₂COOH | ← | ← | ← |
| 40 | tetrahydrothienopyridinyl | —CH₂NHCH₂CH₂— | CH | —OCH₂COOH | —OCH₂COOH | ← | ← |
| 41 | ← | —CH₂NCH₂CH₂— with COCH₃ branch | ← | —OCH₂COOCH₂—[cyclic anhydride with CH₃, O, O] | —OCH₂COOH | H | H |
| 42 | tetrahydrothienopyridinyl | —CONHCH₂CO | ← | ← | —OCH₂COOCH₂—[cyclic anhydride with CH₃, O, O] | ← | ← |

TABLE 1-continued

Structure:
$$A-B-Y-\text{(phenyl ring with } R^{z1}, R^{z2}, R^{z3}, R^{z4}, X\text{)}$$

| Example | A– | –B–Y– | X | $R^{z1}$ | $R^{z2}$ | $R^{z3}$ | $R^{z4}$ |
|---|---|---|---|---|---|---|---|
| 43 | 4-piperidinyl (HN-) | –CH$_2$CH$_2$–(isoxazolyl) | ↑ | –OCH$_2$COOH | –OCH$_2$COOH | ↑ | ↑ |
| 44 | ↑ | –CONHCH$_2$CO– | N | –OCH$_2$COOH | H | ↑ | ↑ |
| 45 | ↑ | –CONHCH$_2$CH(OH)– | CH | –OCH$_2$COOH | –OCH$_2$COOH | ↑ | ↑ |
| 46 | ↑ | (thiazolyl)–CO– | ↑ | –OCH$_2$COOH | H | ↑ | ↑ |
| 47 | ↑ | –CO–(thiazolyl) | ↑ | ↑ | ↑ | ↑ | ↑ |
| 48 | tetrahydrothiazolo-pyridinyl | –CONHCH$_2$CH(OH)– | CH | –OCH$_2$COOH | –OCH$_2$COOH | H | H |
| 49 | tetrahydrothieno-pyridinyl | –CONHCH$_2$CO– | ↑ | ↑ | –O–CH$_2$CH$_2$CH$_3$ | ↑ | ↑ |

TABLE 1-continued

![Structure: benzene ring with substituents A-B-Y at one position, R#1, R#2, R#3, R#4 at others, X in ring]

| Example | A— | —B—Y— | X | R#1 | R#2 | R#3 | R#4 |
|---|---|---|---|---|---|---|---|
| 50 | ↑ | ↑ | ↑ | ↑ | —O—CH₂—Ph | ↑ | ↑ |
| 51 | ↑ | —CONH— | ↑ | ↑ | —OCH₂COOEt | ↑ | ↑ |
| 52 | ↑ | —CONHCH₂CO— | ↑ | ↑ | H | ↑ | ↑ |
| 53 | ↑ | ↑ | ↑ | ↑ | —OH | ↑ | ↑ |
| 54 | ↑ | ↑ | N | ↑ | —O—CO—NH—Et | ↑ | ↑ |
| 55 | ↑ | ↑ | ↑ | —OCH₂COO-n-Bu | —OCH₂COOH | ↑ | ↑ |
| 56 | ↑ | ↑ | CH | —OCH₂COO—⟨C₆H₁₁⟩ | —OCH₂COO-n-Bu | ↑ | ↑ |
| 57 | ↑ | —CONCH₂CO—<br>    \|<br>    CH₃ | ↑ | —OCH₂COOH | —OCH₂COO—⟨C₆H₁₁⟩ | ↑ | ↑ |
| 58 | HN=C(NH₂)—C₆H₄— | ↑ | ↑ | ↑ | —OCH₂COOH | ↑ | ↑ |

Pharmacological test 1 Inhibition of platelet aggregation

The effect of the compound according to the present invention on inhibiting the platelet aggregation was examined with human PRP (platelet rich plasma).

Nine volumes of a blood sample was taken out of the vein of a normal male human with a syringe in which one volume of a 3.8% sodium citrate solution was charged. The blood sample was centrifuged at 170×g at room temperature for 10 minutes. The supernatant thus obtained was isolated as PRP. The residual blood sample that PRP had been taken out was centrifuged at 2,700×g for 15 minutes. The supernatant was then taken as platelet poor plasma (PPP).

Platelet aggregation test was conducted with an aggligometer (PAM-8C; manufactured by MEBANICKS Co., Ltd.). Compounds to be tested were dissolved in a 50% DMSO saline, a 50% methanol saline or physiological saline. The compound and PRP were preincubated for 2 minutes. The ADP (CHRONO-PAR REAGENTS 384 ADP, CHRONO-LOG Corp.) was used as an inducer in the form of a dilution with saline so that the final concentration is 5 μM.

Anti-platelet aggregation activity was obtained as an inhibition rate to platelet aggregation effect of ADP in the absence of a compound to be tested as follows:

$$\text{Anti-platelet aggregation activity} = \left(1 - \frac{\text{Aggregation rate by } ADP \text{ with test compound}}{\text{Aggregation rate by } ADP \text{ without test compound}}\right) \times 100$$

Physiological test 2 Inhibition of fibrinogen bonding to platelet GPIIb/IIIa

Inhibiting effect of the compound according to the present invention on the binding of platelet GPIIb/IIIa and fibrinogen was examined with a solid phase human platelet GPIIb/IIIa bonding assay using biotinylated fibrinogen as a ligand.

Human platelet GPIIb/IIIa was purified according to the method described by Pytela, R. et al. (Science, 231, 1559-1561 (1986)).

Briefly, platelets collected from healthy adults was washed with TBS (0.15M NaCl/50 mM Tris-HCl buffer, pH 7.5) containing 0.2% (w/v) glucose. The same amount of TBS containing 50 mM octylglucoside and 2 mM PMSF was added to the pellet obtained in order to solubilize the membrane protein at 4° C. for 20 minutes. The extract was centrifuged at 3,500×g at 4° C. for 20 minutes, 1 mM CaCl$_2$ and 1 mM MgCl$_2$ were added to the supernatant to give a sample for affinity chromatography. The solubilized protein solution was adsorbed on a GRGDSPK-Sepharose column which had been equilibrated with TBS (Buffer A) containing 50 mM Octylglucoside, 1 mM CaCl$_2$ and MgCl$_2$. After the column was washed with Buffer A, the adsorbed GPIIb/IIIa was eluted with Buffer A containing 2 mM GRGDSP peptide.

GRGDSPK-Sepharose was prepared by coupling GRGDSPK peptide and CNBr-activated Sepharose 4B (Pharmacia) according to the instruction of the manufacturer.

Then, solid phase human platelet GPIIb/IIIa bonding assay was carried out according to the method of Mori et al. (NIPPON KESSEN SHIKETSU GAKKAISHI, 2 (4), 323-329 (1991)).

Purified human platelet GPIIb/IIIa was adjusted in an amount of 2 μg/ml and adsorbed in an amount of 50 μl on a 96 well-microtiter plate at 4° C. overnight. After washing with TBS containing 1 mM CaCl$_2$ and 1 mM MgCl$_2$, 100 μl of 1% bovine serum albumin was added, blocking was conducted at 4° C. overnight. After washing with TBS containing 0.01% Tween 20 (TBS-Tween 20), reaction was conducted at room temperature for 4 hours by adding 50 μl of biotinylated fibrinogen of which the concentration had been adjusted to 1 μg/ml and 50 μl of the test compound which had been adjusted to appropriate concentrations. After washing with TBS-Tween 20, 50 μl of peroxidase labelled avidin which had been diluted with TBS to 4,000 times was added. The reaction was continued for 20 minutes. After washing with TBS-Tween 20, reaction was conducted for 5 minutes by adding 50 μl of a solution of a 10 time diluted peroxidase substrate buffer in which 1 ml/ml of ABTS (2,2'-Azino-bis(3-ethylbenzthiazoline-6-sulfonic acid) was dissolved. A 50 μl portion of a 0.1M citrate buffer containing 0.05% NaN$_3$ was added to stop the reaction, and absorbance at 415 nm was measured.

The rate of Bonding inhibition was calculated from the following formula:

$$\text{Binding Inhibition Rate (\%)} = \left(1 - \frac{\text{Absorbance with test compound}}{\text{Absorbance without test compound}}\right) \times 100$$

Anti-platelet aggregation activities and effects of the compound according to the present invention on bonding inhibition between platelet GPIIb/IIIa and fibrinogen are shown in the following tables.

TABLE 2

| Compound of Example | Pharmacological Test 1 | Pharmacological Test 2 |
|---|---|---|
| 1 | 68%*[1] | 51%*[2] |
| 4 | 85%*[1] | 73%*[2] |
| 7 | 48%*[1] | 27%*[2] |
| 9 | 79%*[1] | 73%*[3] |
| 10 | 85%*[1] | 82%*[3] |

*[1]: inhibition rate at $10^{-6}$M
*[2]: inhibition rate at $10^{-5}$M
*[3]: inhibition rate at $10^{-7}$M

TABLE 3

| Compound of Example | Pharmacological Test 1 (IC$_{50}$, μM) | Pharmacological Test 2 (IC$_{50}$, μM) |
|---|---|---|
| 18 | 0.14 | 1.7 |
| 19 | 0.55 | 3.6 |
| 20 | — | 34 |
| 21 | 0.5 | 10 |
| 22 | 1.2 | >10 |
| 25 | 1.5 | — |
| 26 | 1.0 | — |
| 27 | 2.5 | 9.5 |
| 28 | >10 | 27 |
| 29 | 0.23 | 1.4 |
| 30 | 1.9 | 8.7 |
| 31 | 0.15 | 6.0 |
| 32 | 0.48 | — |
| 33 | 1.7 | 14 |
| 34 | 0.93 | 26 |
| 35 | 0.35 | 42 |
| 36 | 9.0 | >100 |
| 37 | 4.9 | >100 |
| 38 | 8.0 | >100 |
| 39 | 0.26 | 2.7 |
| 40 | 4.0 | >10 |
| 41 | 3.3 | — |
| 42 | 0.34 | — |
| 43 | 2.8 | 100 |
| 44 | 0.72 | 100 |
| 45 | 0.46 | 2.2 |
| 47 | 6.4 | 5.7 |
| 56 | 1.1 | — |
| 57 | 3.2 | — |
| 58 | 0.14 | 26 |

What is claimed is:

1. A compound represented by the formula (I) or a pharmaceutically acceptable salt and solvate thereof:

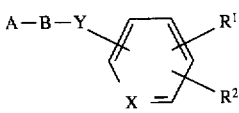

wherein

R¹ represents a group —W—(CH₂)ᵢ-COOR³, where W represents —O— or a bond, R³ represents hydrogen, lower alkyl, C₅₋₇ cycloalkyl or an ester moiety which may be removed under a physiological condition, and i is an integer from 1 to 4, R² represents hydrogen or a group —W—(CH₂)ᵢ-COOR³, where W, R³ and i have the same meanings as defined above, or a group —OR⁴, where R⁴ represents hydrogen, lower alkyl, mono lower alkylaminocarbonyl or phenyl-lower alkyl, X represents CH or N, Y represents
(i) a group —(CO)ₖ—N(R⁵)—Z—,
where k represents 0 or 1, R⁵ represents hydrogen; lower alkyl; or acyl, Z represents a bond, or a group —(CH₂)ₘ—CO— or a group —(CH₂)ₘ—CHR⁶—, where m is an integer from 1 to 3 and R⁶ represents hydrogen or hydroxyl, (ii) a group —CO—(CH₂)ₘ—N(R⁵)—(CO)ₖ—
where k, m and R⁵ have the same meanings as defined above, or (iii) a group —(CO)ₖ-Het
where Het represents a five-membered heterocyclic ring containing 1 to 4 nitrogen atoms, or a six-membered ring which has 1 or 2 nitrogen atoms, which may optionally contain an oxygen atom or a sulfur atom when the ring contains 1 or 2 nitrogen atoms, and
where k has the same meaning as defined above, A represents
(i) the following group (III):

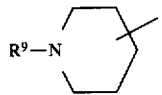

wherein

R⁹ represents hydrogen; lower alkyl in which one or more hydrogen atoms may be substituted by hydroxyl, halogen, amino or lower alkyl amino; or amidino, or (ii) the following group (IV):

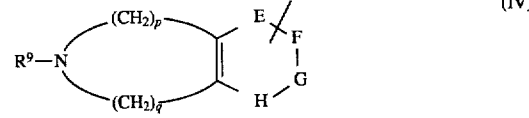

wherein

R⁹ has the same meanings as defined above, one of E or H represents —NR¹⁰—, —O— or —S— and the other represents a bond, F and G represent —CR¹⁰—, where R¹⁰ represents hydrogen, lower alkyl or phenyl-lower alkyl, p and q independently are 1 or 2 provided that p+q is 3, and B represents a bond, C₁₋₆ alkylene or C₂₋₆ alkenylene.

2. A compound according to claim 1, wherein Y represents the group —(CO)ₖ—N(R⁵)—Z—, where k is 1, or the group —(CO)ₖ—Het—, A represents the group (III), and B represents a bond or C₁₋₆alkylene.

3. A compound according to claim 2, wherein Z represents the group —(CH₂)ₘ—CO— or the group —(CH₂)ₘ—CHR⁶— where R⁶ represents hydrogen, and B represents a bond or C₁₋₆alkylene.

4. A compound according to claim 1, wherein Y represents the group —(CO)ₖ—N(R⁵)—Z— where k is 1, or the group —(CO)ₖ—Het—, A represents the group (IV), and B represents a bond or C₁₋₆alkylene.

5. A compound according to claim 4, wherein either of p or q is 1, and the other is 2.

6. A compound according to claim 4, wherein either of F or G represents —CR¹⁰= where R¹⁰ represents hydrogen, and the other represents —CR¹⁰= where R¹⁰ do not represent hydrogen.

7. A compound according to claim 4, wherein A represents the group (IV) where one of E or H represents —NR¹⁰—, —O— or —S—, and the other represents a bond.

8. A compound according to claim 4, wherein Y represents the group —(CO)ₖ—Het—.

9. The compound according to claim 1, which is [[4-[[ [4,5,6,7-tetrahydrothieno[3,2-c]pyridin-2-yl)carbonylamino]acetyl]-o-phenylene]dioxy]diacetic acid trifluoroacetate.

10. The compound according to claim 1, which is [[4-[2-[(4,5,6,7-tetrahydrothieno[3,2-c]pyridin-2-yl)carbonyl]aminoethyl]-o-phenylene]dioxy]diacetic acid trifluoroacetate.

11. The compound according to claim 1, which is [[4-[[ [(4,5,6,7-tetrahydrothieno[3,2-c]pyridin-2-yl]carbonyl]-N-methylamino]acetyl]-o-phenylene]dioxy]diacetic acid trifluoroacetate.

12. The compound according to claim 1, which is [[4-[N-[(4,5,6,7-tetrahydrothieno[3,2-c]pyridin-2-yl]carbonyl]methyl]carbamoyl]-o-phenylene]dioxy]diacetic acid trifluoroacetate.

13. The compound according to claim 1, which is Diethyl [[4-[[[4,5,6,7-tetrahydrothieno[3,2-c]pyridin-2-yl)carbonyl]amino]acetyl]-o-phenylene]dioxy]diacetate trifluoroacetate.

14. The compound according to claim 1, which is Di-n-butyl [[4-[[[(4,5,6,7-tetrahydrothieno[3,2-c]pyridin-2-yl)carbonyl]amino]acetyl]-o-phenylene]dioxy]diacetate trifluoroacetate.

15. The compound according to claim 1, which is Dicyclohexyl [[4-[[[(4,5,6,7-tetrahydrothieno[3,2-c]pyridin-2-yl)carbonyl]amino]acetyl]-o-phenylene]dioxy]diacetate trifluoroacetate.

16. A pharmaceutical composition comprising an effective amount of the compound according to claim 1 or a pharmacologically acceptable salt or solvate thereof together with a pharmacologically acceptable carrier.

17. A pharmaceutical composition according to claim 16 used a platelet aggregation inhibitor.

18. A pharmaceutical composition according to claim 16 used for the treatment or prophylaxis of thrombotic diseases which can be treated or prevented by inhibiting platelet aggregation.

19. A pharmaceutical composition according to claim 18, wherein said thrombotic diseases are cerebral infarction, infarction, angina pectoris or peripheral arterial atresia.

20. A method for treatment or prophylaxis of thrombotic diseases which can be treated or prevented by inhibiting platelet aggregation comprising the step of administering to mammals an effective amount of the compound according to claim 1.

21. A method for treatment or prophylaxis of thrombotic diseases according to claim 20 wherein thrombotic diseases are cerebral infarction, cardiac infarction, angina pectoris or peripheral arterial atresia.

* * * * *